US011326193B1

(12) United States Patent
Davis et al.

(10) Patent No.: US 11,326,193 B1
(45) Date of Patent: May 10, 2022

(54) ENRICHMENT OF AMINO ACIDS FROM BIOMASS RESIDUUM

(71) Applicant: National Technology & Engineering Solutions of Sandia, LLC, Albuquerque, NM (US)

(72) Inventors: Ryan Wesley Davis, San Jose, CA (US); Fang Liu, Pleasanton, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 62 days.

(21) Appl. No.: 16/388,385

(22) Filed: Apr. 18, 2019

Related U.S. Application Data

(63) Continuation-in-part of application No. 15/447,567, filed on Mar. 2, 2017, now Pat. No. 10,683,519.

(60) Provisional application No. 62/303,282, filed on Mar. 3, 2016.

(51) Int. Cl.
| | | |
|---|---|---|
| C12P 13/08 | (2006.01) | |
| C12P 13/20 | (2006.01) | |
| C12P 13/24 | (2006.01) | |
| C12P 13/06 | (2006.01) | |
| C12N 15/81 | (2006.01) | |
| C12P 13/22 | (2006.01) | |

(52) U.S. Cl.
CPC ............ *C12P 13/08* (2013.01); *C12N 15/81* (2013.01); *C12P 13/06* (2013.01); *C12P 13/20* (2013.01); *C12P 13/225* (2013.01); *C12P 13/24* (2013.01); *C12Y 101/01001* (2013.01); *C12Y 101/01086* (2013.01); *C12Y 202/01006* (2013.01)

(58) Field of Classification Search
None
See application file for complete search history.

(56) References Cited

U.S. PATENT DOCUMENTS

| | | | |
|---|---|---|---|
| 6,030,587 A | 2/2000 | Haroldsen et al. | |
| 6,869,015 B2 | 3/2005 | Cummings et al. | |
| 7,022,861 B1 | 4/2006 | McElhanon et al. | |
| 7,253,008 B2 | 8/2007 | Rucker et al. | |
| 7,264,962 B1 | 9/2007 | Simmons et al. | |
| 7,351,380 B2 | 4/2008 | Simmons et al. | |
| 7,351,837 B1 | 4/2008 | McElhanon et al. | |
| 7,358,221 B1 | 4/2008 | Jamison et al. | |
| 7,378,533 B1 | 5/2008 | McElhanon et al. | |
| 7,390,377 B1 | 6/2008 | Wallow et al. | |
| 7,419,574 B2 | 9/2008 | Cummings et al. | |
| 7,556,945 B1 | 7/2009 | Simmons et al. | |
| 7,559,961 B2 | 7/2009 | Jimeson et al. | |
| 7,560,028 B1 | 7/2009 | Simmons et al. | |
| 7,595,349 B1 | 9/2009 | McElhanon et al. | |
| 7,608,461 B1 | 10/2009 | Simmons et al. | |
| 7,622,596 B1 | 11/2009 | McElhanon et al. | |
| 7,666,289 B2 | 2/2010 | Simmons et al. | |
| 7,678,256 B2 | 3/2010 | Davalos et al. | |
| 7,811,439 B1 | 10/2010 | Simmons et al. | |
| 7,985,868 B1 | 7/2011 | Bauer et al. | |
| 8,047,978 B1 | 11/2011 | Haroldsen et al. | |
| 8,257,568 B1 | 9/2012 | Simmons et al. | |
| 8,257,571 B1 | 9/2012 | Cummings et al. | |
| 8,481,974 B1 | 7/2013 | Davis et al. | |
| 8,808,588 B1 | 8/2014 | Simmons et al. | |
| 9,157,130 B2 | 10/2015 | Brennan et al. | |
| 9,322,042 B2 | 4/2016 | Sapra et al. | |
| 9,376,728 B2 | 6/2016 | Zhang et al. | |
| 9,624,482 B2 | 4/2017 | Simmons et al. | |
| 9,725,749 B2 | 8/2017 | Chen et al. | |
| 9,765,044 B2 | 9/2017 | Socha et al. | |
| 9,803,182 B2 | 10/2017 | Gladden et al. | |
| 9,862,982 B2 | 1/2018 | Zhang et al. | |
| 10,077,454 B1 | 9/2018 | Davis et al. | |
| 10,112,916 B2 | 10/2018 | Sathitsuksanoh et al. | |
| 10,155,735 B2 | 12/2018 | Socha et al. | |
| 10,208,076 B2 | 2/2019 | Singh et al. | |
| 10,233,292 B2 | 3/2019 | Singh et al. | |
| 2008/0261230 A1* | 10/2008 | Liao ............... | C12N 9/0006 435/6.18 |
| 2008/0274526 A1* | 11/2008 | Bramucci ............ | C12P 7/16 435/160 |
| 2010/0143997 A1* | 6/2010 | Buelter ............. | C12N 9/0008 435/160 |
| 2013/0288325 A1* | 10/2013 | Liao ............... | C12P 7/04 435/161 |

FOREIGN PATENT DOCUMENTS

| | | | | |
|---|---|---|---|---|
| WO | WO-2012173660 A2 * | 12/2012 | ............... | C12P 7/16 |

OTHER PUBLICATIONS

Martinez-Amezcua C et al. Nutritional Characteristics of Corn Distillers Dried Grains with Solubles as Affected by the Amounts of Grains Versus Solubles and Different Processing Techniques. 2007. Poultry Science. 86:2624-2630. (Year: 2007).*
U.S. Appl. No. 14/750,993, filed Jun. 25, 2015, Hewson et al.
U.S. Appl. No. 15/066,651, filed Mar. 10, 2016, Wu et al..
U.S. Appl. No. 15/447,567, filed Mar. 2, 2017, Davis et al..
Alterthum F et al., "Efficient ethanol production from glucose, lactose, and xylose by Yecombinant *Escherichia coli,*" *Appl. Environ. Microbiol.* 1989;55:1943-8.

(Continued)

*Primary Examiner* — Paul J Holland
(74) *Attorney, Agent, or Firm* — Medley, Behrens & Lewis, LLC; Helen S. Baca; Madelynne J. Farber

(57) ABSTRACT

The present invention relates to methods of providing a biomass residuum and compositions thereof. In particular examples, the biomass residuum includes one or more high value amino acids, even after removal of mixed alcohol components. In particular, the methods include implementing pre-treatment conditions and employing fermentation conditions including modified organisms.

20 Claims, 40 Drawing Sheets

Specification includes a Sequence Listing.

(56) References Cited

OTHER PUBLICATIONS

Atsumi S et al., "Engineering the isobutanol biosynthetic pathway in *Escherichia coli* by comparison of three aldehyde reductase/alcohol dehydrogenase genes," *Appl. Microbiol. Biotechnol.* 2010;85:651-7.
Atsumi S et al., "Non-fermentative pathways for synthesis of branched-chain higher alcohols as biofuels," *Nature* 2008;451:86-9.
Bastian S et al., "Engineered ketol-acid reductoisomerase and alcohol dehydrogenase enable anaerobic 2-methylpropan-1-ol production at theoretical yield in *Escherichia coli*," *Metab. Eng.* 2011;13(3):345-52.
Bizukojc M et al., "Metabolic modelling of syntrophic-like growth of a 1,3-propanediol producer, *Clostridium butyricum*, and a methanogenic archeon, *Methanosarcina mazei*, under anaerobic conditions," *Bioprocess Biosyst. Eng.* 2010;33:507-23.
Bothast RJ et al., "Biotechnological processes for conversion of corn into ethanol," *Appl. Microbiol. Biotechnol.* 2005;67:19-25.
Brinkkötter A et al., "Pathways for the utilization of N-acetyl-galactosamine and galactosamine in *Escherichia coli*," *Mol. Microbiol.* 2000;37:125-35.
Brinkmann-Chen S et al., "General approach to reversing ketol-acid reductoisomerase cofactor dependence from NADPH to NADH," *Proc. Acad. Nat'l Sci. USA* 2013;110:10946-51.
Chubukov V et al., "Synthetic and systems biology for microbial production of commodity chemicals," *npj Syst. Biol. Appl.* 2016;2:16009 (11 pp.).
Datsenko KA et al., "One-step inactivation of chromosomal genes in *Escherichia coli* K-12 using PCR products," *Proc. Nat'l Acad. Sci. USA* 2000;97:6640-5.
De La Plaza M et al., "Biochemical and molecular characterization of α-ketoisovalerate decarboxylase, an enzyme involved in the formation of aldehydes from amino acids by *Lactococcus lactis*," *FEMS Microbiol. Lett.* 2004;238:367-74.
Dueber JE et al., "Synthetic protein scaffolds provide modular control over metabolic flux," *Nat. Biotechnol.* 2009;27:753-9.
Friedman M, "Applications of the ninhydrin reaction for analysis of amino acids, peptides, and proteins to agricultural and biomedical sciences," *J. Agric. Food Chem.* 2004;52:385-406.
Garcia-Moscoso JL et al., "Flash hydrolysis of microalgae (*Scenedesmus* sp.) for protein extraction and production of biofuels intermediates," *J. Supercrit. Fluids* 2013;82:183-90.
Garcia-Moscoso JL et al., "Kinetics of peptides and arginine production from microalgae (*Scenedesmus* sp.) by flash hydrolysis," *Ind. Eng. Chem. Res.* 2015;54(7):2048-58.
Goers L et al., "Co-culture systems and technologies: taking synthetic biology to the next level," *J. R. Soc. Interface* 2014;11:20140065 (13 pp.).
Hernández D et al., "Biofuels from microalgae: lipid extraction and methane production from the residual biomass in a biorefinery approach," *Bioresour. Technol.* 2014;170:370-8.
Huang R et al., "PCR-based multiple species cell counting for in vitro mixed culture," *PLoS One* 2015;10:e0126628 (13 pp.).
Huo YX et al., "Conversion of proteins into biofuels by engineering nitrogen flux," *Nat. Biotechnol.* 2011;29:346-51.
Keasling D, "Sustainable production of advanced biofuels," *241st ACS National Meeting & Exposition*, held on Mar. 27-31, 2011 in Anaheim, CA, Abstract 202 (1 p.).
Kim JH et al., "Simultaneous consumption of pentose and hexose sugars: an optimal microbial phenotype for efficient fermentation of lignocellulosic biomass," *Appl. Microbiol. Biotechnol.* 2010;88:1077-85.
Kim Y et al., "Enzyme hydrolysis and ethanol fermentation of liquid hot water and AFEX pretreated distillers' grains at high-solids loadings," *Bioresour. Technol.* 2008;99:5206-15.
Kurokawa M et al., "Correlation between genome reduction and bacterial growth," *DNA Res.* 2016;23:517-25.
Kyrpides NC et al., "Genomic encyclopedia of bacteria and archaea: sequencing a myriad of type strains," *PLoS Biol.* 2014;12:e1001920 (7 pp.).

Lan EI et al., "Microbial synthesis of n-butanol, isobutanol, and other higher alcohols from diverse resources," *Bioresour. Technol.* 2013;135:339-49.
Li K et al., "An overview of algae bioethanol production," *Int. J. Energy Res.* 2014;38(8):965-77.
Liao JC et al., "Fuelling the future: microbial engineering for the production of sustainable biofuels," *Nat. Rev. Microbiol.* 2016;14:288-304.
Liu F et al., "Bioconversion of distillers' grain hydrolysates to advanced biofuels by an Escherichia coli co-culture," *Microb. Cell Fact.* 2017;16:192 (14 pp.).
Liu F et al., "Engineering microbial consortia for bioconversion of multisubstrate biomass streams to biofuels," Chapter 7 (pp. 101-120) in *Biofuels: Challenges and opportunities* (M. Al Qubeissi, ed.), IntechOpen (London, United Kingdom), 2019.
Liu F et al., "Functional assembly of a multi-enzyme methanol oxidation cascade on a surface-displayed trifunctional scaffold for enhanced NADH production," *Chem. Commun.* 2013;49:3766-8.
Liu KS, "Chemical composition of distillers grains, a review," *J. Agric. Food Chem.* 2011;59:1508-26.
López Barreiro D et al., "Assessing microalgae biorefinery routes for the production of biofuels via hydrothermal liquefaction," *Bioresour. Technol.* 2014;174:256-65.
Luque R, "Algal biofuels: the eternal promise?," *Energy Environ. Sci.* 2010;3:254-7.
Ma F et al., "Biodiesel production: a review," *Bioresourc. Technol.* 1999;70:1-15.
Masuko T et al., "Carbohydrate analysis by a phenol-sulfuric acid method in microplate format," *Anal. Biochem.* 2005;339:69-72.
Melis A et al., "Hydrogen production: green algae as a source of energy," *Plant Physiol.* 2001;127(3):740-8.
Naik SN et al., "Production of first and second generation biofuels: a comprehensive review," *Renew. Sustain. Energy Rev.* 2010;14:578-97.
Noureddini H et al., "Dilute-acid pretreatment of distillers' grains and corn fiber," *Bioresour. Technol.* 2010;101:1060-7.
Palmqvist E et al., "Fermentation of lignocellulosic hydrolysates. II: inhibitors and mechanisms of inhibition," *Bioresour. Technol.* 2000;74:25-33.
Park M et al., "Positional assembly of enzymes on bacterial outer membrane vesicles for cascade reactions," *PLoS One* 2014;9:e97103 (6 pp.).
Peralta-Yahya PP et al., "Microbial engineering for the production of advanced biofuels," *Nature* 2012;488(7411):320-8.
Qu Y et al., "Use of a coculture to enable current production by *Geobacter sulfurreducens*," *Appl. Environ. Microbiol.* 2012;78:3484-7.
Raheem A et al., "Thermochemical conversion of microalgal biomass for biofuel production," *Renew. Sustain. Energy Rev.* 2015;49:990-9.
Razeghifard R, "Algal biofuels," *Photosynth. Res.* 2013;117(1-3):207-19.
Ringer M et al., "Large-scale pyrolysis oil production: a technology assessment and economic analysis," *National Renewable Energy Laboratory Technical Report NREL/TP-510-37779*, Nov. 2006, 93 pp.
Sarathy SM et al., "Alcohol combustion chemistry," *Prog. Energy Combust. Sci.* 2014;44:40-102.
Schneider RCS et al., "Potential production of biofuel from microalgae biomass produced in wastewater," in *Biodiesel—Feedstocks, Production and Applications*, Prof. Zhen Fang (ed.), InTech, 2012, 22 pp.
Scott SA et al., "Biodiesel from algae: challenges and prospects," *Curr. Opin. Biotechnol.* 2010;21(3):277-86.
Sharma KK et al., "High lipid induction in microalgae for biodiesel production," *Energies* 2012;5(5):1532-53.
Shi A et al., "Activating transhydrogenase and NAD kinase in combination for improving isobutanol production," *Metab. Eng.* 2013;16:1-10.
Singh J et al., "Commercialization potential of microalgae for biofuels production," *Renew. Sustain. Energy Rev.* 2010;14(9):2596-610.

(56) References Cited

OTHER PUBLICATIONS

Smith KM et al., "An evolutionary strategy for isobutanol production strain development in *Escherichia coli*," *Metab. Eng.* 2011;13(6):674-81.

Studier FW et al., "Understanding the differences between genome sequences of *Escherichia coli* B strains REL606 and BL21 (DE3) and comparison of the *E. coli* B and K-12 genomes," *J. Mol. Biol.* 2009;394:653-80.

Sulzenbacher G et al., "Crystal structure of *E. coli* alcohol dehydrogenase YqhD: evidence of a covalently modified NADP coenzyme," *J. Mol. Biol.* 2004;342(2):489-502.

Tran NH et al., "Catalytic upgrading of biorefinery oil from microalgae," *Fuel* 2010;89:265-74.

Um BH et al., "Effect of sulfuric and phosphoric acid pretreatments on enzymatic hydrolysis of corn stover," *Appl. Biochem. Biotechnol.* 2003;105-108:115-25.

Wildschut J et al., "Catalyst studies on the hydrotreatment of fast pyrolysis oil," *Appl. Catalysis* B 2010;99:298-306.

Wu W, "Fuel ethanol production using novel carbon sources and fermentation medium optimization with response surface methodology," *Int. J. Agric. Biol. Eng.* 2013;6:42-53.

Wu W et al., "Cofactor engineering of ketol-acid reductoisomerase (IlvC) and alcohol dehydrogenase (YqhD) improves the fusel alcohol yield in algal protein anaerobic fermentation," *Algal Res.* 2016;19:162-7.

Wu W et al., "One-pot bioconversion of algae biomass into terpenes for advanced biofuels and bioproducts," *Algal Res.* 2016;17:316-20.

Wu W et al., "Site-saturation mutagenesis of formate dehydrogenase from *Candida bodinii* creating effective NADP+-dependent FDH enzymes," *J. Molec. Catal.* B 2009;61 (3-4): 157-61.

Zhang H et al., "Engineering *Escherichia coli* coculture systems for the production of biochemical products," *Proc. Nat'l Acad. Sci. USA* 2015;112:8266-71.

Zhou YJ et al., "Production of fatty acid-derived oleochemicals and biofuels by synthetic yeast cell factories," *Nat. Common.* 2016;7:11709 (9 pp.).

Zhu Y et al., "Dilute-acid pretreatment of corn stover using a high-solids percolation reactor," *Appl. Biochem. Biotechnol.* 2004;117:103-14.

* cited by examiner

Redox mutants screening

Escherichia coli alcohol dehydrogenase YqhD (SEQ ID NO:1)

```
         10         20         30         40         50
MNNFNLHTPT RILFGKGAIA GLREQIPHDA RVLITYGGGS VKKTGVLDQV
         60         70         80         90        100
LDALKGMDVL EFGGIEPNPA YETLMNAVKL VREQKVTFLL AVGGGSVLDG
        110        120        130        140        150
TKFIAAAANY PENIDPWHIL QTGGKEIKSA IPMGCVLTLP ATGSESNAGA
        160        170        180        190        200
VISRKTTGDK QAFHSAHVQP VFAVLDPVYT YTLPPRQVAN GVVDAFVHTV
        210        220        230        240        250
EQYVTKPVDA KIQDRFAEGI LLTLIEDGPK ALKEPENYDV RANVMWAATQ
        260        270        280        290        300
ALNGLIGAGV PQDWATHMLG HELTAMHGLD HAQTLAIVLP ALWNEKRDTK
        310        320        330        340        350
RAKLLQYAER VWNITEGSDD ERIDAAIAAT RNFFEQLGVP THLSDYGLDG
        360        370        380
SSIPALLKKL EEHGMTQLGE NHDITLDVSR RIYEAAR
```

FIG. 10C

YqhD mutant 1 (SEQ ID NO:2)

```
         10         20         30         40         50
MNNFNLHTPT RILFGKGAIA GLREQIPHDA RVLITYGGXS VKKTGVLDQV
         60         70         80         90        100
LDALKGMDVL EFGGIEPNPA YETLMNAVKL VREQKVTFLL AVGGGSVLDG
        110        120        130        140        150
TKFIAAAANY PENIDPWHIL QTGGKEIKSA IPMGCVLTLP ATGSESNAGA
        160        170        180        190        200
VISRKTTGDK QAFHSAHVQP VFAVLDPVYT YTLPPRQVAN GVVDAFVHTV
        210        220        230        240        250
EQYVTKPVDA KIQDRFAEGI LLTLIEDGPK ALKEPENYDV RANVMWAATQ
        260        270        280        290        300
ALNGLIGAGV PQDWATHMLG HELTAMHGLD HAQTLAIVLP ALWNEKRDTK
        310        320        330        340        350
RAKLLQYAER VWNITEGSDD ERIDAAIAAT RNFFEQLGVP THLSDYGLDG
        360        370        380
SSIPALLKKL EEHGMTQLGE NHDITLDVSR RIYEAAR
```

FIG. 10D

YqhD mutant 2 (SEQ ID NO:3)

```
         10         20         30         40         50
MNNFNLHTPT RILFGKGAIA GLREQIPHDA RVLITYGGGX VKKTGVLDQV
         60         70         80         90        100
LDALKGMDVL EFGGIEPNPA YETLMNAVKL VREQKVTFLL AVGGGSVLDG
        110        120        130        140        150
TKFIAAAANY PENIDPWHIL QTGGKEIKSA IPMGCVLTLP ATGSESNAGA
        160        170        180        190        200
VISRKTTGDK QAFHSAHVQP VFAVLDPVYT YTLPPRQVAN GVVDAFVHTV
        210        220        230        240        250
EQYVTKPVDA KIQDRFAEGI LLTLIEDGPK ALKEPENYDV RANVMWAATQ
        260        270        280        290        300
ALNGLIGAGV PQDWATHMLG HELTAMHGLD HAQTLAIVLP ALWNEKRDTK
        310        320        330        340        350
RAKLLQYAER VWNITEGSDD ERIDAAIAAT RNFFEQLGVP THLSDYGLDG
        360        370        380
SSIPALLKKL EEHGMTQLGE NHDITLDVSR RIYEAAR
```

FIG. 10E

YqhD mutant 3 (SEQ ID NO:4)

```
         10         20         30         40         50
MNNFNLHTPT RILFGKGAIA GLREQIPHDA RVLITYGGXX VKKTGVLDQV
         60         70         80         90        100
LDALKGMDVL EFGGIEPNPA YETLMNAVKL VREQKVTFLL AVGGGSVLDG
        110        120        130        140        150
TKFIAAAANY PENIDPWHIL QTGGKEIKSA IPMGCVLTLP ATGSESNAGA
        160        170        180        190        200
VISRKTTGDK QAFHSAHVQP VFAVLDPVYT YTLPPRQVAN GVVDAFVHTV
        210        220        230        240        250
EQYVTKPVDA KIQDRFAEGI LLTLIEDGPK ALKEPENYDV RANVMWAATQ
        260        270        280        290        300
ALNGLIGAGV PQDWATHMLG HELTAMHGLD HAQTLAIVLP ALWNEKRDTK
        310        320        330        340        350
RAKLLQYAER VWNITEGSDD ERIDAAIAAT RNFFEQLGVP THLSDYGLDG
        360        370        380
SSIPALLKKL EEHGMTQLGE NHDITLDVSR RIYEAAR
```

FIG. 10F

YqhD mutant 4 (SEQ ID NO:5)

```
          10         20         30         40         50
  MNNFNLHTPT RILFGKGAIA GLREQIPHDA RVLITYXXXX VKKTGVLDQV
          60         70         80         90        100
  LDALKGMDVL EFGGIEPNPA YETLMNAVKL VREQKVTFLL AVGGGSVLDG
         110        120        130        140        150
  TKFIAAAANY PENIDPWHIL QTGGKEIKSA IPMGCVLTLP ATGSESNAGA
         160        170        180        190        200
  VISRKTTGDK QAFHSAHVQP VFAVLDPVYT YTLPPRQVAN GVVDAFVHTV
         210        220        230        240        250
  EQYVTKPVDA KIQDRFAEGI LLTLIEDGPK ALKEPENYDV RANVMWAATQ
         260        270        280        290        300
  ALNGLIGAGV PQDWATHMLG HELTAMHGLD HAQTLAIVLP ALWNEKRDTK
         310        320        330        340        350
  RAKLLQYAER VWNITEGSDD ERIDAAIAAT RNFFEQLGVP THLSDYGLDG
         360        370        380
  SSIPALLKKL EEHGMTQLGE NHDITLDVSR RIYEAAR
```

FIG. 10G

*Escherichia coli* ketol-acid reductoisomerase IlvC (SEQ ID NO:6)

```
         10         20         30         40         50
MANYFNTLNL RQQLAQLGKC RFMGRDEFAD GASYLQGKKV VIVGCGAQGL
         60         70         80         90        100
NQGLNMRDSG LDISYALRKE AIAEKRASWR KATENGFKVG TYEELIPQAD
        110        120        130        140        150
LVINLTPDKQ HSDVVRTVQP LMKDGAALGY SHGFNIVEVG EQIRKDITVV
        160        170        180        190        200
MVAPKCPGTE VREEYKRGFG VPTLIAVHPE NDPKGEGMAI AKAWAAATGG
        210        220        230        240        250
HRAGVLESSF VAEVKSDLMG EQTILCGMLQ AGSLLCFDKL VEEGTDPAYA
        260        270        280        290        300
EKLIQFGWET ITEALKQGGI TLMMDRLSNP AKLRAYALSE QLKEIMAPLF
        310        320        330        340        350
QKHMDDIISG EFSSGMMADW ANDDKKLLTW REETGKTAFE TAPQYEGKIG
        360        370        380        390        400
EQEYFDKGVL MIAMVKAGVE LAFETMVDSG IIEESAYYES LHELPLIANT
        410        420        430        440        450
IARKRLYEMN VVISDTAEYG NYLFSYACVP LLXPFMAELQ PGDLGKAIPE
        460        470        480        490
GAVDNGQLRD VNEAIRSHAI EQVGKKLRGY MTDMKRIAVA G
```

FIG. 11A

IlvC mutant (SEQ ID NO:7)

```
         10         20         30         40         50
MANYFNTLNL RQQLAQLGKC RFMGRDEFAD GASYLQGKKV VIVGCGAQGL
         60         70         80         90        100
NQGLNMRDSG LDISYALRKE XIAEKXAXWR KATENGFKVG TYEELIPQAD
        110        120        130        140        150
LVINLTPDKX HSDVVRTVQP LMKDGAALGY SHGFNIVEVG EQIRKXITVV
        160        170        180        190        200
MVAPKCPGTE VREEYKRGFG VPTLIAVHPE NDPKXEGMAI AKAWAAATGG
        210        220        230        240        250
HRAGVLESSF VAEVKSDLMG EQTILCGMLQ AGSLLCFDKL VEEGTDPAYA
        260        270        280        290        300
EKLIQFGWET ITEALKQGGI TLMMDRLSNP AKLRAYALSE QLKEIMAPLF
        310        320        330        340        350
QKHMDDIISG EFSSGMMADW ANDDKKLLTW REETGKTAFE TAPQYEGKIG
        360        370        380        390        400
EQEYFDKGVL MIAMVKAGVE LAFETMVDSG IIEESAYYES LHELPLIANT
        410        420        430        440        450
IARKRLYEMN VVISDTAEYG NYLFSYACVP LLXPFMAELQ PGDLGKAIPE
        460        470        480        490
GAVDNGQLRD VNEAIRSHAI EQVGKKLRGY MTDMKRIAVA G
```

FIG. 11B

Bacillus subtilis acetolactate synthase AlsS (SEQ ID NO:50)

```
         10         20         30         40         50
MTKATKEQKS LVKSRGAELV VDCLVEQGVT HVFGIPGAKI DAVFDALQDK
         60         70         80         90        100
GPEIIVARHE QNAAFMAQAV GRLTGKPGVV LVTSGPGASN LATGLLTANT
        110        120        130        140        150
EGDPVVALAG NVIRADRLKR THQSLDNAAL FQPITKYSVE VQDVKNIPEA
        160        170        180        190        200
VTNAFRIASA GQAGAAFVSF PQDVVNEVTN TKNVRAVAAP KLGPAADDAI
        210        220        230        240        250
SAAIAKIQTA KLPVVLVGMK GGRPEAIKAV RKLLKKVQLP FVETYQAAGT
        260        270        280        290        300
LSRDLEDQYF GRIGLFRNQP GDLLLEQADV VLTIGYDPIE YDPKFWNVNG
        310        320        330        340        350
DRTIIHLDEI LADIDHAYQP ELELIGDIPS TINHIEHDAV KVDFAEREQK
        360        370        380        390        400
ILSDLKQYMH EGEQVPADWK SDRVHPLEIV KELRNAVDDH VTVTCDIGSH
        410        420        430        440        450
AIWMSRYFRS YEPLTLMISN GMQTLGVALP WAIGASLVKP GEKVVSVSGD
        460        470        480        490        500
GGFLFSAMEL ETAVRLKAPI VHIVWNDSTY DMVAFQQLKK YNRTSAVDFG
        510        520        530        540        550
NIDIVKYAES FGATGLRVES PDQLADVLRQ GMNAEGPVII DVPVDYSDNM
        560        570
NLASDKLPKE FGELMKTKAL
```

FIG. 24A

Bacillus subtilis (strain 168) acetolactate synthase AlsS (SEQ ID NO:51)

```
         10         20         30         40         50
MTKATKEQKS LVKSRGAELV VDCLVEQGVT HVFGIPGAKI DAVFDALQDK
         60         70         80         90        100
GPEIIVARHE QNAAFMAQAV GRLTGKPGVV LVTSGPGASN LATGLLTANT
        110        120        130        140        150
EGDPVVALAG NVIRADRLKR THQSLDNAAL FQPITKYSVE VQDVKNIPEA
        160        170        180        190        200
VTNAFRIASA GQAGAAFVSF PQDVVNEVTN TKNVRAVAAP KLGPAADDAI
        210        220        230        240        250
SAAIAKIQTA KLPVVLVGMK GGRPEAIKAV RKLLKKVQLP FVETYQAAGT
        260        270        280        290        300
LSRDLEDQYF GRIGLFRNQP GDLLLEQADV VLTIGYDPIE YDPKFWNVNG
        310        320        330        340        350
DRTIIHLDEI LADIDHAYQP ELELIGDIPS TINHIEHDAV KVDFAEREQK
        360        370        380        390        400
ILSDLKQYMH EGEQVPADWK SDRVHPLEIV KELRNAVDDH VTVTCDIGSH
        410        420        430        440        450
AIWMSRYFRS YEPLTLMISN GMQTLGVALP WAIGASLVKP GEKVVSVSGD
        460        470        480        490        500
GGFLFSAMEL ETAVRLKAPI VHIVWNDSTY DMVAFQQLKK YNRTSAVDFG
        510        520        530        540        550
NIDIVKYAES FGATGLRVES PDQLADVLRQ GMNAEGPVII DVPVDYSDNM
        560        570
NLASDKLPKE FGELMKTKAL
```

FIG. 24B

***Klebsiella pneumoniae* acetolactate synthase BudB (SEQ ID NO:52)**

```
         10         20         30         40         50
MDKQYPVRQW AHGADLVVSQ LEAQGVRQVF GIPGAKIDKV FDSLLDSSIR
         60         70         80         90        100
IIPVRHEANA AFMAAAVGRI TGKAGVALVT SGPGCSNLIT GMATANSEGD
        110        120        130        140        150
PVVALGGAVK RADKAKQVHQ SMDTVAMFSP VTKYAIEVTA PDALAEVVSN
        160        170        180        190        200
AFRAAEQGRP GSAFVSLPQD VVDGPVSGKV LPASGAPQMG AAPDDAIDQV
        210        220        230        240        250
AKLIAQAKNP IFLLGLMASQ PENSKALRRL LETSHIPVTS TYQAAGAVNQ
        260        270        280        290        300
DNFSRFAGRV GLFNNQAGDR LLQLADLVIC IGYSPVEYEP AMWNSGNATL
        310        320        330        340        350
VHIDVLPAYE ERNYTPDVEL VGDIAGTLNK LAQNIDHRLV LSPQAAEILR
        360        370        380        390        400
DRQHQRELLD RRGAQLNQFA LHPLRIVRAM QDIVNSDVTL TVDMGSFHIW
        410        420        430        440        450
IARYLYTFRA RQVMISNGQQ TMGVALPWAI GAWLVNPERK VVSVSGDGGF
        460        470        480        490        500
LQSSMELETA VRLKANVLHL IWVDNGYNMV AIQEEKKYQR LSGVEFGPMD
        510        520        530        540        550
FKAYAESFGA KGFAVESAEA LEPTLRAAMD VDGPAVVAIP VDYRDNPLLM

GQLHLSQIL
```

FIG. 24C

***Lactococcus lactis* alpha-acetolactate synthase Als (SEQ ID NO:53)**

```
         10         20         30         40         50
MSEKQFGANL VVDSLINHKV KYVFGIPGAK IDRVFDLLEN EEGPQMVVTR
         60         70         80         90        100
HEQGAAFMAQ AVGRLTGEPG VVVVTSGPGV SNLATPLLTA TSEGDAILAI
        110        120        130        140        150
GGQVKRSDRL KRAHQSMDNA GMMQSATKYS AEVLDPNTLS ESIANAYRIA
        160        170        180        190        200
KSGHPGATFL SIPQDVTDAE VSIKAIQPLS DPKMGNASID DINYLAQAIK
        210        220        230        240        250
NAVLPVILVG AGASDAKVAS SLRNLLTHVN IPVVETFQGA GVISHDLEHT
        260        270        280        290        300
FYGRIGLFRN QPGDMLLKRS DLVIAVGYDP IEYEARNWNA EIDSRIIVID
        310        320        330        340        350
NAIAEIDTYY QPERELIGDI AATLDNLLPA VRGYKIPKGT KDYLDGLHEV
        360        370        380        390        400
AEQHEFDTEN TEEGRMHPLD LVSTFQEIVK DDETVTVDVG SLYIWMARHF
        410        420        430        440        450
KSYEPRHLLF SNGMQTLGVA LPWAITAALL RPGKKVYSHS GDGGFLFTGQ
        460        470        480        490        500
ELETAVRLNL PIVQIIWNDG HYDMVKFQEE MKYGRSAAVD FGYVDYVKYA
        510        520        530        540        550
EAMRAKGYRA HSKEELAEIL KSIPDTTGPV VIDVPLDYSD NIKLAEKLLP

EEFY
```

FIG. 24D

*E. coli* MG1655 dihydroxyacid dehydratase IlvD (SEQ ID NO:54)

```
         10         20         30         40         50
MPKYRSATTT HGRNMAGARA LWRATGMTDA DFGKPIIAVV NSFTQFVPGH
         60         70         80         90        100
VHLRDLGKLV AEQIEAAGGV AKEFNTIAVD DGIAMGHGGM LYSLPSRELI
        110        120        130        140        150
ADSVEYMVNA HCADAMVCIS NCDKITPGML MASLRLNIPV IFVSGGPMEA
        160        170        180        190        200
GKTKLSDQII KLDLVDAMIQ GADPKVSDSQ SDQVERSACP TCGSCSGMFT
        210        220        230        240        250
ANSMNCLTEA LGLSQPGNGS LLATHADRKQ LFLNAGKRIV ELTKRYYEQN
        260        270        280        290        300
DESALPRNIA SKAAFENAMT LDIAMGGSTN TVLHLLAAAQ EAEIDFTMSD
        310        320        330        340        350
IDKLSRKVPQ LCKVAPSTQK YHMEDVHRAG GVIGILGELD RAGLLNRDVK
        360        370        380        390        400
NVLGLTLPQT LEQYDVMLTQ DDAVKNMFRA GPAGIRTTQA FSQDCRWDTL
        410        420        430        440        450
DDDRANGCIR SLEHAYSKDG GLAVLYGNFA ENGCIVKTAG VDDSILKFTG
        460        470        480        490        500
PAKVYESQDD AVEAILGGKV VAGDVVVIRY EGPKGGPGMQ EMLYPTSFLK
        510        520        530        540        550
SMGLGKACAL ITDGRFSGGT SGLSIGHVSP EAASGGSIGL IEDGDLIAID
        560        570        580        590        600
IPNRGIQLQV SDAELAARRE AQDARGDKAW TPKNRERQVS FALRAYASLA
        610
TSADKGAVRD KSKLGG
```

FIG. 24E

*Lactococcus lactis* 2-ketoacid decarboxylase Kdc (SEQ ID NO:55)

```
         10         20         30         40         50
MYTVGDYLLD RLHELGIEEI FGVPGDYNLQ FLDQIISHKD MKWVGNANEL
         60         70         80         90        100
NASYMADGYA RTKKAAAFLT TFGVGELSAV NGLAGSYAEN LPVVEIVGSP
        110        120        130        140        150
TSKVQNEGKF VHHTLADGDF KHFMKMHEPV TAARTLLTAE NATVEIDRVL
        160        170        180        190        200
SALLKERKPV YINLPVDVAA AKAEKPSLPL KKENSTSNTS DQEILNKIQE
        210        220        230        240        250
SLKNAKKPIV ITGHEIISFG LEKTVTQFIS KTKLPITTLN FGKSSVDEAL
        260        270        280        290        300
PSFLGIYNGT LSEPNLKEFV ESADFILMLG VKLTDSSTGA FTHHLNENKM
        310        320        330        340        350
ISLNIDEGKI FNERIQNFDF ESLISSLLDL SEIEYKGKYI DKKQEDFVPS
        360        370        380        390        400
NALLSQDRLW QAVENLTQSN ETIVAEQGTS FFGASSIFLK SKSHFIGQPL
        410        420        430        440        450
WGSIGYTFPA ALGSQIADKE SRHLLFIGDG SLQLTVQELG LAIREKINPI
        460        470        480        490        500
CFIINNDGYT VEREIHGPNQ SYNDIPMWNY SKLPESFGAT EDRVVSKIVR
        510        520        530        540
TENEFVSVMK EAQADPNRMY WIELILAKEG APKVLKKMGK LFAEQNKS
```

FIG. 24F

*Lactococcus lactis* branched-chain alpha-ketoacid decarboxylase KdcA (SEQ ID NO:56)

```
            10         20         30         40         50
    MYTVGDYLLD RLHELGIEEI FGVPGDYNLQ FLDQIISRED MKWIGNANEL
            60         70         80         90        100
    NASYMADGYA RTKKAAAFLT TFGVGELSAI NGLAGSYAEN LPVVEIVGSP
           110        120        130        140        150
    TSKVQNDGKF VHHTLADGDF KHFMKMHEPV TAARTLLTAE NATYEIDRVL
           160        170        180        190        200
    SQLLKERKPV YINLPVDVAA AKAEKPALSL EKESSTTNTT EQVILSKIEE
           210        220        230        240        250
    SLKNAQKPVV IAGHEVISFG LEKTVTQFVS ETKLPITTLN FGKSAVDESL
           260        270        280        290        300
    PSFLGIYNGK LSEISLKNFV ESADFILMLG VKLTDSSTGA FTHHLDENKM
           310        320        330        340        350
    ISLNIDEGII FNKVVEDFDF RAVVSSLSEL KGIEYEGQYI DKQYEEFIPS
           360        370        380        390        400
    SAPLSQDRLW QAVESLTQSN ETIVAEQGTS FFGASTIFLK SNSRFIGQPL
           410        420        430        440        450
    WGSIGYTFPA ALGSQIADKE SRHLLFIGDG SLQLTVQELG LSIREKLNPI
           460        470        480        490        500
    CFIINNDGYT VEREIHGPTQ SYNDIPMWNY SKLPETFGAT EDRVVSKIVR
           510        520        530        540
    TENEFVSVMK EAQADVNRMY WIELVLEKED APKLLKKMGK LFAEQNK
```

FIG. 24G

*Salmonella typhimurium* (strain LT2/SGSC1412/ATCC 700720) indolepyruvate decarboxylase (SEQ ID NO:57)

```
            10         20         30         40         50
    MQNPYTVADY LLDRLAGCGI GHLFGVPGDY NLQFLDHVID HPTLRWVGCA
            60         70         80         90        100
    NELNAAYAAD GYARMSGAGA LLTTFGVGEL SAINGIAGSY AEYVPVLHIV
           110        120        130        140        150
    GAPCSAAQQR GELMHHTLGD GDFRHFYRMS QAISAASAIL DEQNACFEID
           160        170        180        190        200
    RVLGEMLAAR RPGYIMLPAD VAKKTAIPPT QALALPVHEA QSGVETAFRY
           210        220        230        240        250
    HARQCLMNSR RIALLADFLA GRFGLRPLLQ RWMAETPIAH ATLLMGKGLF
           260        270        280        290        300
    DEQHPNFVGT YSAGASSKEV RQAIEDADRV ICVGTRFVDT LTAGFTQQLP
           310        320        330        340        350
    AERTLEIQPY ASRIGETWFN LPMAQAVSTL RELCLECAFA PPPTRSAGQP
           360        370        380        390        400
    VRIDKGELTQ ESFWQTLQQY LKPGDIILVD QGTAAFGAAA LSLPDGAEVV
           410        420        430        440        450
    LQPLWGSIGY SLPAAFGAQT ACPDRRVILI IGDGAAQLTI QEMGSMLRDG
           460        470        480        490        500
    QAPVILLLNN DGYTVERAIH GAAQRYNDIA SWNWTQIPPA LNAAQQAECW
           510        520        530        540        550
    RVTQAIQLAE VLERLARPQR LSFIEVMLPK ADLPELLRTV TRALEARNGG
```

FIG. 24H

***Clostridium acetobutylicum* pyruvate decarboxylase (SEQ ID NO:58)**

```
         10         20         30         40         50
MKSEYTIGRY LLDRLSELGI RHIFGVPGDY NLSFLDYIME YKGIDWVGNC
         60         70         80         90        100
NELNAGYAAD GYARINGIGA ILTTFGVGEL SAINAIAGAY AEQVPVVKIT
        110        120        130        140        150
GIPTAKVRDN GLYVHHTLGD GRFDHFFEMF REVTVAEALL SEENAAQEID
        160        170        180        190        200
RVLISCWRQK RPVLINLPID VYDKPINKPL KPLLDYTISS NKEAACEFVT
        210        220        230        240        250
EIVPIINRAK KPVILADYGV YRYQVQHVLK NLAEKTGFPV ATLSMGKGVF
        260        270        280        290        300
NEAHPQFIGV YNGDVSSPYL RQRVDEADCI ISVGVKLTDS TTGGFSHGFS
        310        320        330        340        350
KRNVIHIDPF SIKAKGKKYA PITMKDALTE LTSKIEHRNF EDLDIKPYKS
        360        370        380        390        400
DNQKYFAKEK PITQKRFFER IAHFIKEKDV LLAEQGTCFF GASTIQLPKD
        410        420        430        440        450
ATFIGQPLWG SIGYTLPALL GSQLADQKRR NILLIGDGAF QMTAQEISTM
        460        470        480        490        500
LRLQIKPIIF LINNDGYTIE RAIHGREQVY NNIQMWRYHN VPKVLGPKEC
        510        520        530        540        550
SLTFKVQSET ELEKALLVAD KDCEHLIFIE VVMDRYDKPE PLERLSKRFA
NQNN
```

FIG. 24I

ENRICHMENT OF AMINO ACIDS FROM BIOMASS RESIDUUM

CROSS-REFERENCE TO RELATED APPLICATIONS

This application is a continuation-in-part of U.S. patent application Ser. No. 15/447,567, filed Mar. 2, 2017, which in turn claims the benefit of U.S. Provisional Application No. 62/303,282, filed Mar. 3, 2016, each of which is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to methods of providing a biomass residuum and compositions thereof. In particular examples, the biomass residuum includes one or more high value amino acids, even after removal of mixed alcohol components. In particular, the methods include implementing pre-treatment conditions and employing fermentation conditions including modified organisms.

BACKGROUND OF THE INVENTION

Production of distillers' dried grains (DDGs), the primary co-product of residue from corn ethanol production, has dramatically increased since about 2002. Despite potential utility for this product for animal feed blending, market adoption of the feedstock has been limited due to inconsistent composition and potential toxicity to livestock. Such co-products, as well as other biomass products, can contain high value components that are difficult to recover and isolate. Accordingly, there is a need for methods and tools to facilitate such isolation in an effective and/or efficient manner.

SUMMARY OF THE INVENTION

The present invention relates to compositions derived from processed biomass, in which the compositions include higher value amino acids, even after removing mixed alcohol components useful for making biofuels. In particular, the compositions are derived from a fermented biomass, in which one or more genetically engineered organisms are employed as a fermentation agent to preferentially degrade lower value amino acids within a biomass into alcohol, thereby leaving residual higher value amino acids (e.g., valine, glutamic acid, proline, etc.). Such higher value amino acids can be present within the fermentation broth, which is obtained by fermenting the biomass.

Fermentation can be inhibited by, e.g., substrate depletion, the presence of several chemical constituents, by-product competition, etc. For instance, a biomass can include multiple substrates that can be difficult for a single organism to process. Accordingly, in one aspect, the present invention features use of a co-culture including a plurality of organism, e.g., a first organism to degrade one or more carbohydrates in a biomass and a second organism to degrade amino acids, proteins, and peptides in the biomass. In particular embodiments, the second organism, alone or in a co-culture, preferentially degrades low value amino acids. In another non-limiting instance, cofactor imbalance can limit fermentation, e.g., in which the lack of a particular cofactor can result in limited yield of desired fermentation products. Thus, in some non-limiting methods herein, the first organism is modified to cofactor specificity in order to achieve cofactor balance in one or more biosynthetic pathways (e.g., by providing a genetically modified organism suited for employing a cofactor that does not limit fermentation, such as an organism that is selected by direct evolution to have a non-native cofactor specificity).

The methods herein can be optimized to recover any useful component (e.g., biocomponent, intermediate, etc.). In one non-limiting example, the fermentation liquor was extracted with ethyl acetate to recover the mixed alcohols at about 90% yield, and the extraction solvent was recovered by distillation. Further lyophilization of the extracted fermentation liquor yielded a crystalline powder enriched with high value amino acids.

Accordingly, in a first aspect, the present invention features a composition including a fermented broth derived from a fermented biomass. In particular embodiments, the broth includes of from about 10% total to about 25% total of valine, about 10% total to about 20% total of glutamic acid, about 5% total to about 15% total of proline, about 5% total to about 15% total of alanine, about 5% total to about 15% total of aspartic acid, about 3% total to about 10% total of tyrosine, about 3% total to about 10% total of glycine, and/or about 3% total to about 10% total of histidine, as well as salts thereof.

In other embodiments, the fermented biomass includes a distillers' grain fermented with a first genetically engineered organism (e.g., any described herein) and a second genetically engineered organism (e.g., any described herein). In some embodiments, the first genetically engineered organism degrades one or more carbohydrates in the distillers' grain, and/or the second genetically engineered organism degrades the one or more amino acids, proteins, or peptides in the distillers' grain.

In some embodiments, the fermented biomass includes the distillers' grain pretreated with one or more acids (e.g., any described herein, including a dilute acid, such as of from about 3% (v/v) to about 10% (v/v) of an acid) and/or enzymes (e.g., any described herein, including a protease). In other embodiments, the fermented biomass includes the distillers' grain pretreated with an acid and with a protease. In yet other embodiments, the fermented biomass includes the distillers' grain pretreated with an acid to a pH of from about 5 to about 7 (e.g., about 6).

In some embodiments, the composition (e.g., the fermented broth) includes of about 20% total of valine, about 15% total of glutamic acid, about 10% total of proline, about 10% total of alanine, about 10% total of aspartic acid, about 35% total of tyrosine, about 5% total of glycine, and/or about 5% total of histidine, as well as salts thereof.

In some embodiment, the composition (e.g., the fermented broth) includes of from about 50% total to about 85% total of amino acids on a dry weight basis.

In a second aspect, the present invention features a method of providing a biomass residuum, the method including pre-treating a biomass with one or more acids and/or enzymes, thereby providing one or more biocomponents (e.g., including one or more carbohydrates, amino acids, proteins, and peptides); fermenting the biocomponents with a first genetically engineered organism and a second genetically engineered organism, thereby providing a first fermentation product; and separating the first fermentation product, thereby providing a mixed alcohol portion and the biomass residuum comprising of from about 50% total to about 80% total of amino acids on a dry weight basis.

In some embodiments, the first genetically engineered organism degrades the one or more carbohydrates, and the second genetically engineered organism degrades the one or more amino acids, proteins, and peptides.

In some embodiments, the biomass residuum includes of from about 10% total to about 25% total of valine, about 10% total to about 20% total of glutamic acid, about 5% total to about 15% total of proline, about 5% total to about 15% total of alanine, about 5% total to about 15% total of aspartic acid, about 3% total to about 10% total of tyrosine, about 3% total to about 10% total of glycine, and/or about 3% total to about 10% total of histidine, as well as salts thereof.

In other embodiments, the biomass residuum includes about 20% total of valine, about 15% total of glutamic acid, about 10% total of proline, about 10% total of alanine, about 10% total of aspartic acid, about 35% total of tyrosine, about 5% total of glycine, and/or and about 5% total of histidine, as well as salts thereof.

In some embodiments, the separating step further includes separating one or more lipids from the first fermentation product, thereby extracting the one or more lipids from the biomass residuum.

In a third aspect, the present invention features a method of providing a biomass residuum, the method including: pre-treating the biomass with one or more acids and/or one or more enzymes, thereby providing one or more biocomponents (e.g., including one or more carbohydrates, amino acids, proteins, and peptides); fermenting the one or more biocomponents with a first genetically engineered organism and a second genetically engineered organism, thereby providing a first fermentation product (e.g., wherein the first genetically engineered organism degrades the one or more carbohydrates and the second genetically engineered organism degrades the one or more amino acids, proteins, and peptides); separating one or more alcohols from the fermentation product, thereby resulting in a separated fermentation portion; and lyophilizing the separated fermentation portion, thereby providing the biomass residuum comprising of from about 50% total to about 80% total of amino acids on a dry weight basis.

In some embodiments, the pre-treating step includes pre-treating the biomass with an acid and with an enzyme.

In some embodiments, the biomass residuum includes of from about 10% total to about 25% total of valine, about 10% total to about 20% total of glutamic acid, about 5% total to about 15% total of proline, about 5% total to about 15% total of alanine, about 5% total to about 15% total of aspartic acid, about 3% total to about 10% total of tyrosine, about 3% total to about 10% total of glycine, and/or about 3% total to about 10% total of histidine, as well as salts thereof.

In any embodiment herein, a composition (e.g., a fermented broth, a fermented biomass, a lyophilized component, a biomass residuum, etc.) derived from a biomass (e.g., a fermented biomass, a fermented and lyophilized biomass, a fermented and separated and lyophilized biomass, a fermented biomass with removed alcohol portions, a fermented and lyophilized biomass with removed alcohol portions, as well as any biomass described herein) can include of from about 10% total to about 30% total (e.g., from about 10% total to 15% total, 10% total to 20% total, 10% total to 25% total, 13% total to 15% total, 13% total to 20% total, 13% total to 25% total, 13% total to 30% total, 15% total to 20% total, 15% total to 25% total, 15% total to 30% total, 17% total to 20% total, 17% total to 23% total, 17% total to 25% total, 17% total to 27% total, 17% total to 30% total, 20% total to 25% total, 20% total to 30% total, 23% total to 25% total, 23% total to 30% total, or 25% total to 30% total) of valine, about 7% total to about 25% total (e.g., from about 7% total to 10% total, 7% total to 13% total, 7% total to 15% total, 7% total to 17% total, 7% total to 20% total, 7% total to 23% total, 10% total to 13% total, 10% total to 15% total, 10% total to 17% total, 10% total to 20% total, 10% total to 23% total, 10% total to 25% total, 13% total to 15% total, 13% total to 17% total, 13% total to 20% total, 13% total to 23% total, 13% total to 25% total, 15% total to 17% total, 15% total to 20% total, 15% total to 23% total, 15% total to 25% total, 17% total to 20% total, 17% total to 23% total, 17% total to 25% total, 20% total to 23% total, 20% total to 25% total, or 23% total to 25% total) of glutamic acid, about 5% total to about 20% total (e.g., from about 5% total to 10% total, 5% total to 13% total, 5% total to 15% total, 5% total to 17% total, 7% total to 10% total, 7% total to 13% total, 7% total to 15% total, 7% total to 17% total, 7% total to 20% total, 10% total to 13% total, 10% total to 15% total, 10% total to 17% total, 10% total to 20% total, 13% total to 15% total, 13% total to 17% total, 13% total to 20% total, 15% total to 17% total, 15% total to 20% total, or 17% total to 20% total) of proline, about 3% total to about 15% total (e.g., from about 3% total to 5% total, 3% total to 7% total, 3% total to 10% total, 3% total to 13% total, 5% total to 7% total, 5% total to 10% total, 5% total to 13% total, 5% total to 15% total, 7% total to 10% total, 7% total to 13% total, 7% total to 15% total, 10% total to 13% total, 10% total to 15% total, or 13% total to 15% total) of alanine, about 3% total to about 15% total (e.g., from about 3% total to 5% total, 3% total to 7% total, 3% total to 10% total, 3% total to 13% total, 5% total to 7% total, 5% total to 10% total, 5% total to 13% total, 5% total to 15% total, 7% total to 10% total, 7% total to 13% total, 7% total to 15% total, 10% total to 13% total, 10% total to 15% total, or 13% total to 15% total) of aspartic acid, about 2% total to about 10% total (e.g., from about 2% total to 3% total, 2% total to 5% total, 2% total to 7% total, 2% total to 10% total, 3% total to 5% total, 3% total to 7% total, 3% total to 10% total, 5% total to 7% total, 5% total to 10% total, or 7% total to 10% total) of tyrosine, about 2% total to about 10% total (e.g., from about 2% total to 3% total, 2% total to 5% total, 2% total to 7% total, 2% total to 10% total, 3% total to 5% total, 3% total to 7% total, 3% total to 10% total, 5% total to 7% total, 5% total to 10% total, or 7% total to 10% total) of glycine, and/or and about 2% total to about 10% total (e.g., from about 2% total to 3% total, 2% total to 5% total, 2% total to 7% total, 2% total to 10% total, 3% total to 5% total, 3% total to 7% total, 3% total to 10% total, 5% total to 7% total, 5% total to 10% total, or 7% total to 10% total) of histidine, as well as salts thereof.

In any embodiment herein, a composition derived from a biomass (e.g., any described herein) can include more than about 3% total (e.g., of from about 3% total to about 25% total, including 3% total to 5% total, 3% total to 7% total, 3% total to 10% total, 3% total to 15% total, 3% total to 17% total, 3% total to 20% total, 3% total to 23% total, 3% total to 25% total, 3% total to 30% total, 5% total to 7% total, 5% total to 10% total, 5% total to 15% total, 5% total to 17% total, 5% total to 20% total, 5% total to 23% total, 5% total to 25% total, 5% total to 30% total, 7% total to 10% total, 7% total to 15% total, 7% total to 17% total, 7% total to 20% total, 7% total to 23% total, 7% total to 25% total, 7% total to 30% total, 10% total to 15% total, 10% total to 17% total, 10% total to 20% total, 10% total to 23% total, 10% total to 25% total, 10% total to 30% total, 13% total to 15% total, 13% total to 17% total, 13% total to 20% total, 13% total to 23% total, 13% total to 25% total, 13% total to 30% total, 15% total to 17% total, 15% total to 20% total, 15% total to 23% total, 15% total to 25% total, 15% total to 30% total, 17% total to 20% total, 17% total to 23% total, 17% total to 25% total, 17% total to 30% total, 20% total to 23% total, 20% total to 25% total, 20% total to 30% total, 23% total to 25% total, 23% total to 30% total, 25% total to 30% total, or 27% total to 30% total) of one or more of the following amino acids: glycine, proline, alanine, aspartic acid, valine, tyrosine, glycine, and/or histidine, as well as salts thereof. In other embodiments, a composition derived from a biomass (e.g., any described herein) can include more than about 3% total (e.g., of from about 3% total to about 25% total, including 3% total to 5% total, 3% total to 7% total, 3% total to 10% total, 3% total to 15% total, 3% total to 17% total, 3% total to 20% total, 3% total to 23% total, 3% total to 25% total, 3% total to 30% total, 5% total to 7% total, 5% total to 10% total, 5% total to 15% total, 5% total to 17% total, 5% total to 20% total, 5% total to 23% total, 5% total to 25% total, 5% total to 30% total, 7% total to 10% total, 7% total to 15% total, 7% total to 17% total, 7% total to 20% total, 7% total to 23% total, 7% total to 25% total, 7% total to 30% total, 10% total to 15% total, 10% total to 17% total, 10% total to 20% total, 10% total to 23% total, 10% total to 25% total, 10% total to 30% total, 13% total to 15% total, 13% total to 17% total, 13% total to 20% total, 13% total to 23% total, 13% total to 25% total, 13% total to 30% total, 15% total to 17% total, 15% total to 20% total, 15% total to 23% total, 15% total to 25% total, 15% total to 30% total, 17% total to 20% total, 17% total to 23% total, 17% total to 25% total, 17% total to 30% total, 20% total to 23% total, 20% total to 25% total, 20% total to 30% total, 23% total to 25% total, 23% total to 30% total, 25% total to 30% total, or 27% total to 30% total), independently, of each of the following amino acids: glycine, proline, alanine, aspartic acid, valine, tyrosine, glycine, and histidine, as well as salts thereof.

In any embodiment herein, a composition derived from a biomass (e.g., any described herein) includes of from about 50% total to about 85% total (e.g., of from about 50% total to 55% total, 50% total to 60% total, 50% total to 65% total, 50% total to 70% total, 50% total to 75% total, 50% total to 80% total, 53% total to 55% total, 53% total to 60% total, 53% total to 65% total, 53% total to 70% total, 53% total to 75% total, 53% total to 80% total, 53% total to 85% total, 55% total to 60% total, 55% total to 65% total, 55% total to 70% total, 55% total to 75% total, 55% total to 80% total, 55% total to 85% total, 57% total to 60% total, 57% total to 65% total, 57% total to 70% total, 57% total to 75% total, 57% total to 80% total, 57% total to 85% total, 60% total to 65% total, 60% total to 70% total, 60% total to 75% total, 60% total to 80% total, 60% total to 85% total, 63% total to 65% total, 63% total to 70% total, 63% total to 75% total, 63% total to 80% total, 63% total to 85% total, 65% total to 70% total, 65% total to 75% total, 65% total to 80% total, 65% total to 85% total, 67% total to 70% total, 67% total to 75% total, 67% total to 80% total, 67% total to 85% total, 70% total to 75% total, 70% total to 80% total, 70% total to 85% total, 73% total to 75% total, 73% total to 80% total, 73% total to 85% total, 75% total to 80% total, 75% total to 85% total, 77% total to 80% total, 77% total to 85% total, 80% total to 85% total, or 83% total to 85% total) of amino acids on a dry weight basis. In some embodiments, the amino acids are selected from the group consisting of valine, glutamic acid, proline, alanine, aspartic acid, tyrosine, glycine, and histidine, as well as salts thereof. In other embodiments, the amino acids are selected from the group consisting of valine, glutamic acid, proline, alanine, aspartic acid, tyrosine, and glycine, as well as salts thereof. In yet other embodiments, the amino acids are selected from the group consisting of valine, glutamic acid, proline, alanine, aspartic acid, and tyrosine, as well as salts thereof. In other embodiments, the amino acids are selected from the group consisting of valine, glutamic acid, proline, alanine, and aspartic acid, as well as salts thereof.

In any embodiment herein, % total can mean (w/w) %, (w/v) %, or (v/v) %. In other embodiments, % total can mean (w/w) % on a dry weight basis.

In any embodiment herein, the biomass includes distillers' grain (e.g., with or without solubles).

In any embodiment herein, the pre-treating step includes pre-treating the biomass with an acid (e.g., a dilute acid) and with an enzyme (e.g., a protease or a mixture thereof).

In any embodiment herein, the genetically engineered organism (e.g., the first genetically engineered organism) includes an exogenous acetolactate synthase or a nucleic acid encoding the exogenous acetolactate synthase; and an exogenous 2-ketoacid decarboxylase or a nucleic acid encoding the exogenous 2-ketoacid decarboxylase. In some embodiments, the exogenous acetolactate synthase includes a polypeptide sequence having at least 85% (e.g., 87%, 88%, 89%, 90%, 91%, 92%, 93%, 94%, 95%, 96%, 97%, 98%, 99%, 99.9%, or 100%, including of from about 85% to 90%, 85% to 95%, 85% to 99%, 85% to 100%, 90% to 95%, 90% to 99%, 90% to 100%, 95% to 99%, or 95% to 100%) sequence identity to any one of SEQ ID NOs:50-53, or a fragment thereof (e.g., including at least about 10%, 20%, 30%, 40%, 50%, 60%, 70%, 80%, or 90% of the entire length of the reference polypeptide). In some embodiments, the exogenous 2-ketoacid decarboxylase comprises a polypeptide sequence having at least 85% (e.g., 87%, 88%, 89%, 90%, 91%, 92%, 93%, 94%, 95%, 96%, 97%, 98%, 99%, 99.9%, or 100%, including of from about 85% to 90%, 85% to 95%, 85% to 99%, 85% to 100%, 90% to 95%, 90% to 99%, 90% to 100%, 95% to 99%, or 95% to 100%) sequence identity to any one of SEQ ID NOs:55-58, or a fragment thereof (e.g., including at least about 10%, 20%, 30%, 40%, 50%, 60%, 70%, 80%, or 90% of the entire length of the reference polypeptide).

In any embodiment herein, the genetically engineered organism (e.g., the second genetically engineered organism) includes a modified alcohol dehydrogenase having increased reactivity with nicotinamide adenine dinucleotide (NADH), as compared to a wild-type alcohol dehydrogenase, or a nucleic acid encoding the modified alcohol dehydrogenase; and a modified ketol-acid reductoisomerase having increased reactivity with NADH, as compared to a wild-type ketol-acid reductoisomerase, or a nucleic acid encoding the modified ketol-acid reductoisomerase. In some embodiments, the modified alcohol dehydrogenase includes a polypeptide sequence having at least 85% (e.g., 87%, 88%, 89%, 90%, 91%, 92%, 93%, 94%, 95%, 96%, 97%, 98%, 99%, 99.9%, or 100%, including of from about 85% to 90%, 85% to 95%, 85% to 99%, 85% to 100%, 90% to 95%, 90% to 99%, 90% to 100%, 95% to 99%, or 95% to 100%) sequence identity to any one of SEQ ID NOs:1-5, or a fragment thereof (e.g., including at least about 10%, 20%, 30%, 40%, 50%, 60%, 70%, 80%, or 90% of the entire length of the reference polypeptide). In some embodiments, the modified ketol-acid reductoisomerase includes a polypeptide sequence having at least 85% (e.g., 87%, 88%, 89%, 90%, 91%, 92%, 93%, 94%, 95%, 96%, 97%, 98%, 99%, 99.9%, or 100%, including of from about 85% to 90%, 85% to 95%, 85% to 99%, 85% to 100%, 90% to 95%, 90% to 99%, 90% to 100%, 95% to 99%, or 95% to 100%) sequence identity to any one of SEQ ID NOs:6-7, or a fragment thereof (e.g., including at least about 10%, 20%, 30%, 40%, 50%, 60%, 70%, 80%, or 90% of the entire length of the reference polypeptide).

In any embodiment herein, the organism is a bacterium (e.g., selected from the *Escherichia* genus).

In any embodiment herein, the alcohol or mixed alcohol (or a portion thereof) is selected from the group consisting of ethanol, propanol, butanol, and alkylated formed thereof.

In any embodiment herein, the one or more acids includes hydrochloric acid or sulfuric acid.

In any embodiment herein, the one or more enzymes comprises one or more proteases, as well as mixtures thereof.

Additional details follow.

Definitions

As used herein, the term "about" means+/−10% of any recited value. As used herein, this term modifies any recited value, range of values, or endpoints of one or more ranges.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology—Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

The term "fragment" is meant a portion of a nucleic acid or a polypeptide that is at least one nucleotide or one amino acid shorter than the reference sequence. This portion contains, preferably, at least about 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 40% (e.g., about 50%, about 60%, about 70%, about 80%, about 90%, about 95%, about 87%, about 98%, about 99%, or about 100%) identical to any of the sequences described herein can be utilized in accordance with the invention. In certain embodiments, a polypeptide to be utilized in accordance with the invention includes 2, 3, 4, 5, 6, 7, 8, 9, 10, or more mutations (e.g., one or more conservative amino acid substitutions, as described herein). In yet another example, any nucleic acid fragment can include a stretch of at least about 5 (e.g., about 7, about 8, about 10, about 12, about 14, about 18, about 20, about 24, about 28, about 30, or more) nucleotides that are at least about 40% (about 50%, about 60%, about 70%, about 80%, about 90%, about 95%, about 87%, about 98%, about 99%, or about 100%) identical to any of the sequences described herein can be utilized in accordance with the invention.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); and a group of amino acids having sulfur containing side chains consists of cysteine (Cys, C) and methionine (Met, M). Exemplary conservative amino acid substitution groups are valine-leucine-isoleucine, phenylalanine-tyrosine, lysine-arginine, alanine-valine, glycine-serine, glutamate-aspartate, and asparagine-glutamine.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith T F et al., *J. Mol. Biol.* 1981; 147:195-7) and BLAST (Basic Local Alignment Search Tool; Altschul S F et al., *J. Mol. Biol.* 1990; 215:403-10). These and other alignment algorithms are accessible using publicly available computer software such as "Best Fit" (Smith T F et al., *Adv. Appl. Math.* 1981; 2(4):482-9) as incorporated into GeneMatcher Plus™ (Schwarz and Dayhof, "Atlas of Protein Sequence and Structure," ed. Dayhoff, M. O., pp. 353-358, 1979), BLAST, BLAST-2, BLAST-P, BLAST-N, BLAST-X, WU-BLAST-2, ALIGN, ALIGN-2, CLUSTAL, T-COFFEE, MUSCLE, MAFFT, or Megalign (DNASTAR). In addition, those skilled in the art can determine appropriate parameters for measuring alignment, including any algorithms needed to achieve optimal alignment over the length of the sequences being compared. In general, for polypeptides, the length of comparison sequences can be at least five amino acids, preferably 10, 20, 30, 40, 50, 60, 70, 80, 90, 100, 125, 150, 175, 200, 250, 300, 400, 500, 600, 700, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, 1000, 1100, 1200, 1300, 1400, 1500, 1600, 1700, 1800, 1900, 2000, 2100, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 50%, 60%, 70%, 75%, 80%, 85%, 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a host (e.g., a cell).

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

A "host" or "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

As used herein, the term "exogenous" in reference to a nucleic acid or a polypeptide refers to a nucleic acid or a polypeptide that is not normally or naturally found in and/or produced by a given bacterium, organism, or cell in nature. As used herein, the term "endogenous" in reference to a nucleic acid or a polypeptide refers to a nucleic acid or a polypeptide that is normally found in and/or produced by a given bacterium, organism, or cell in nature.

By "salt" is meant an ionic form of a compound or structure (e.g., any formulas, compounds, or compositions described herein), which includes a cation or anion compound to form an electrically neutral compound or structure. Salts (e.g., simple salts having binary compounds, double salts, triple salts, etc.) are well known in the art. For example, salts are described in Berge S M et al., "Pharmaceutical salts," *J. Pharm. Sci.* 1977 January; 66(1):1-19; International Union of Pure and Applied Chemistry, "Nomenclature of Inorganic Chemistry," Butterworth & Co. (Publishers) Ltd., London, England, 1971 (2nd ed.); and in "Handbook of Pharmaceutical Salts: Properties, Selection, and Use," Wiley-VCH, April 2011 (2nd rev. ed., eds. P. H. Stahl and C. G. Wermuth). The salts can be prepared in situ during the final isolation and purification of the compounds of the invention or separately by reacting the free base group with a suitable organic acid (thereby producing an anionic salt) or by reacting the acid group with a suitable metal or organic salt (thereby producing a cationic salt). Representative anionic salts include acetate, adipate, alginate, ascorbate, aspartate, benzenesulfonate, benzoate, bicarbonate, bisulfate, bitartrate, borate, bromide, butyrate, camphorate, camphorsulfonate, chloride, citrate, cyclopentanepropionate, digluconate, dihydrochloride, diphosphate, dodecylsulfate, edetate, ethanesulfonate, fumarate, glucoheptonate, glucomate, glutamate, glycerophosphate, hemisulfate, heptonate, hexanoate, hydrobromide, hydrochloride, hydroiodide, hydroxyethanesulfonate, hydroxynaphthoate, iodide, lactate, lactobionate, laurate, lauryl sulfate, malate, maleate, malonate, mandelate, mesylate, methanesulfonate, methylbromide, methylnitrate, methylsulfate, mucate, 2-naphthalenesulfonate, nicotinate, nitrate, oleate, oxalate, palmitate, pamoate, pectinate, persulfate, 3-phenylpropionate, phosphate, picrate, pivalate, polygalacturonate, propionate, salicylate, stearate, subacetate, succinate, sulfate, tannate, tartrate, theophyllinate, thiocyanate, triethiodide, toluenesulfonate, undecanoate, valerate salts, and the like. Representative cationic salts include metal salts, such as alkali or alkaline earth salts, e.g., barium, calcium (e.g., calcium edetate), lithium, magnesium, potassium, sodium, and the like; other metal salts, such as aluminum, bismuth, iron, and zinc; as well as nontoxic ammonium, quaternary ammonium, and amine cations, including, but not limited to ammonium, tetramethylammonium, tetraethylammonium, methylamine, dimethylamine, trimethylamine, triethylamine, ethylamine, pyridinium, and the like. Other cationic salts include organic salts, such as chloroprocaine, choline, dibenzylethylenediamine, diethanolamine, ethylenediamine, methylglucamine, and procaine.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 10A-10G shows the effects of cofactor engineering for E. coli alcohol dehydrogenase (YqhD). Provided are (A) an image showing structural alignment of the NADP-binding pocket for YqhD and (B) a graph showing mutant enzyme activity employing cofactor NADH, as compared to WT YqhD. Also provided are polypeptide sequences for E. coli YqhD, including sequences for (C) wild-type (SEQ ID NO:1) having Gly at positions 37-39 and Ser at position 40; (D) YqhD mutant 1 including a mutation at position 39 (SEQ ID NO:2), in which Xaa at position 39 can be any useful amino acid substitution (e.g., Ile, Tyr, Val, Leu, Phe, or any other conservative amino acid substitution described herein); (E) YqhD mutant 2 including a mutation at position 40 (SEQ ID NO:3), in which Xaa at position 40 can be any useful amino acid substitution (e.g., Pro, Arg, His, Lys, Trp, or any other conservative amino acid substitution described herein); (F) YqhD mutant 3 including a mutation at both positions 39 and 40 (SEQ ID NO:4), in which Xaa at position 39 and 40 can be any useful amino acid substitution (e.g., Ile at position 39 and Arg at position 40; Tyr at position 39 and His at position 40; as well as any other conservative amino acid substitution described herein); and (G) YqhD mutant 3 including a mutation at positions 39 and 40 (SEQ ID NO:5) with an optional substitution at positions 37 and 38, in which Xaa at position 39 and 40 can be any useful amino acid substitution (e.g., Ile at position 39 and Arg at position 40; Tyr at position 39 and His at position 40; as well as any other conservative amino acid substitution described herein). In some instances, the mutant (e.g., of SEQ ID NO:2-5) includes Gly, Ile, Tyr, Val, Leu, Phe, or any other conservative amino acid substitution described herein, for positions 37, 38, and 39; and Ser, Pro, Arg, His, Lys, Trp, or any other conservative amino acid substitution described herein for position 40 (e.g., in which position 39 and/or 40 includes an amino acid substitution as compared to the wild-type sequence, e.g., SEQ ID NO:1).

FIG. 11A-11B provides polypeptide sequences for E. coli ketol-acid reductoisomerase IlvC, including sequences for (A) wild-type (SEQ ID NO:6) having Ala at position 71, Arg at position 76, Ser at position 78, Gln at position 110, Asp at position 146, Gly at position 185, and Lys at position 433; and (B) IlvC mutant including a mutation at positions 71, 76, 78, and/or 110 (SEQ ID NO:7). Exemplary substitutions include Ser or Thr at position 71, Asp or Glu at position 76, Asp or Glu at position 78, and/or Val or Ala or Leu or Ile at position 110, as well as any other conservative amino acid substitution described herein. Optionally, SEQ ID NO:7 can include other substitutions, including Gly or Ala at position 146, Arg or Lys at position 185, and/or Glu or Asp at position 433.

FIG. 24A-24I provides polypeptide sequences for exemplary acetolactate synthases, including (A) B. subtilis acetolactate synthase AlsS (SEQ ID NO:50), (B) B. subtilis (strain 168) acetolactate synthase AlsS (SEQ ID NO:51), (C) Klebsiella pneumoniae acetolactate synthase BudB (SEQ ID NO:52), (D) Lactococcus lactis alpha-acetolactate synthase Als (SEQ ID NO:53); exemplary dehydratase, including (E) *E. coli* MG1655 dihydroxyacid dehydratase IlvD (SEQ ID NO:54); and exemplary 2-ketoacid decarboxylases, including (F) *Lactococcus lactis* 2-ketoacid decarboxylase Kdc (SEQ ID NO:55), (G) *Lactococcus lactis* branched-chain alpha-ketoacid decarboxylase KdcA (SEQ ID NO:56), (H) *Salmonella typhimurium* (strain LT2/SGSC1412/ATCC 700720) indolepyruvate decarboxylase (SEQ ID NO:57), and (I) *Clostridium acetobutylicum* pyruvate decarboxylase (SEQ ID NO:58).

DETAILED DESCRIPTION OF THE INVENTION

The present invention relates to the upgrading biomass (e.g., high-protein biomass) into ethanol and other useful intermediates, such as amino acids, bioresidue, etc. Such intermediates, in turn, can be suitable for any useful industrial process, such as downstream refining, e.g., using known petrochemical facilities and processes. In particular embodiments, an exemplary process of the invention combines pre-treatment of the biomass to solubilize and hydrolyze the carbohydrate and protein fractions; followed by fermentation and optional distillation/extraction to recover useful alcohols, amino acids, etc. In some embodiments, the process employs biochemical steps to effectively solubilize, hydrolyze, and/or degrade components of the biomass (e.g., by employing one or more, including two or more, genetically engineered organisms, such as any herein).

Figure 1A:
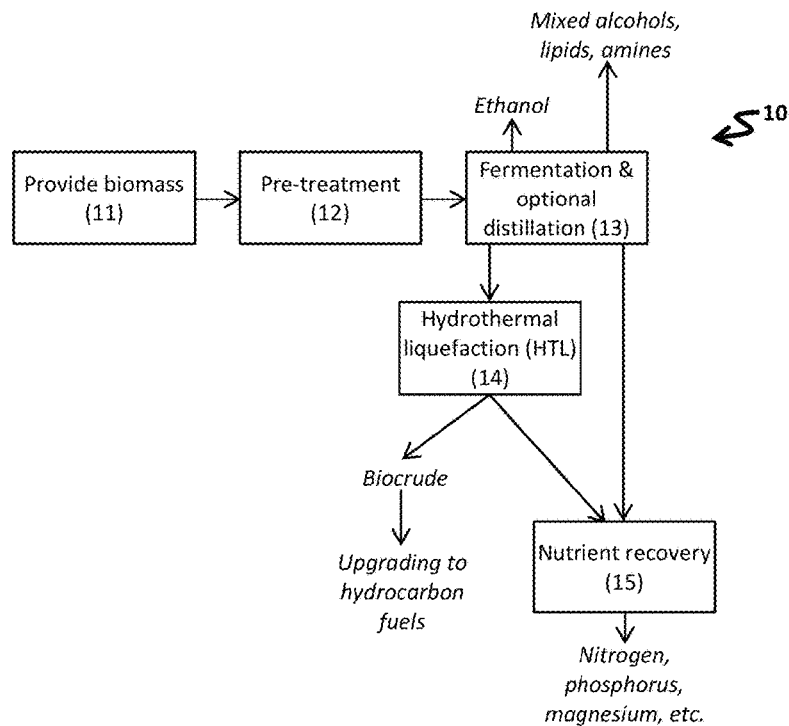
FIG. 1A-1E shows exemplary process flow diagrams for upgrading biomass. Provided are (A) an exemplary process 10 including processing pathways and (B) another exemplary process 100 including a pre-treatment step 121,122 prior to each fermentation step 131,132. The unit operations of the process are depicted as designated boxes, where inputs and outputs are designated by arrows leading either into or away from a box, respectively. Also provided is (C) an exemplary process 1000 with an optional second pre-treatment step 1022. Provided are (D) another exemplary process 1100 with a fermentation step 1131 including fermenting the carbohydrates and proteins within the biomass, as well as (E) yet another exemplary process 1200 with two pre-treatment steps 1221,1222 and a fermentation step 1231 including fermenting the carbohydrates and proteins within the biomass

An exemplary process 10 is shown in FIG. 1A. A biomass 11 is provided, typically including fractions of proteins, carbohydrates, and/or lipids (collectively, biocomponents). Further treatment steps can be employed to breakdown these biocomponents into useful residuals. Exemplary steps include pre-treatment 12 (e.g., employing dilute acid and/or enzymes in sequential or simultaneous steps) to hydrolyze and/or solubilize the biocomponents (e.g., such as to provide one or more sugars, including glucose, xylose, arabinose, etc.); as well as fermentation and optional distillation 13 to degrade the biocomponents into one or more alcohols (e.g., ethanol, 1-propanol, isobutanol, 1-butanol, 2-methyl-1-butanol, 3-methyl-1-butanol, 2-phenylethanol, isopentanol, etc.), amino acids, and amines.

Fermentation is typically employed to degrade sugars, carbohydrates, and proteins into further, smaller chemical components, such as alcohols, amino acids, and amines. In use, fermentation employs one or more organisms, such as bacteria or yeast, to degrade these biocomponents. Exemplary organisms are described herein (e.g., bacteria such as *E. coli*, as well as mutant forms that are selected to degrade sugars, carbohydrates, and/or proteins in a selective, specific, and/or useful manner). Typically, such organisms do not degrade lipids. Thus, conventional fermentation is usually conducted in aqueous, non-lipid samples. In some embodiments of the invention herein, organisms can be genetically modified to convert lipids. In other embodiments of the invention herein, the fermentation step includes use of one or more lipids, lipid vesicles, and/or lipid micelles within the fermentation broth.

After fermentation, one or more by-products (e.g., minerals, nutrients, water, etc.) can be optionally removed from any of the fractions. Nutrients, by-products, and water can be extracted within any point of the processing stream and with any useful mixture obtained within the processing stream. Such extraction steps can include removal of by-products from the fermentation broth or a portion thereof, delivery of nitrogen (N) and/or phosphorous (P) sources (e.g., as a salt, a mineral, etc.), and/or delivery of water. Any fractions obtained from these biocomponents can be processed to recovery nutrients (e.g., N and/or P) in any useful form, such as a protonated form (e.g., ammonia for capturing N), an oxide form (e.g., phosphate for capturing P), a salt form, and/or a mineral (e.g., struvite for capturing N and P).

In other examples, after the fermentation step, the aqueous and non-aqueous (e.g., lipid) fractions are phase-separated and processed in parallel steps. For instance, the non-aqueous fraction, including a bioresidue (e.g., a low nitrogen organic residue) composed of one or more lipids, can be treated by way of hydrothermal liquefaction (HTL) 14 to provide a biocrude oil. Any solid residuals, such as ash or char, can be removed after liquefaction. Any liquid residuals can be further processed to recover 15 any useful nutrients.

In another example, the aqueous fraction (e.g., including water-soluble components) can be distilled to remove alcohols (e.g., along with neutral lipids). Optionally, such fractions or extracted fractions can be further processed to recover any useful nutrients 15 (e.g., for recovering nitrogen and/or phosphorus) or usable water 16 (e.g., for use in multi-pass recycle operations) in the aqueous phase, as well as to extract any lipids present in the aqueous phase.

Any useful thermochemical process can be employed to process a bioresidue into a biocrude oil. Exemplary thermochemical processes include liquefaction, pyrolysis, gasification, and/or combustion in the optional presence of one or more catalysts. Experimental conditions (e.g., temperature, pressure, air composition, reactants, reagents, etc.) can be optimized in any useful manner to achieve the desired biocrude oil with appropriate viscosity, color, oxygen content, nitrogen content, etc. In addition, the biocrude oil can be further upgraded into biofuels, such as by use of hydrotreatment (e.g., as described herein).

Figure 1B:
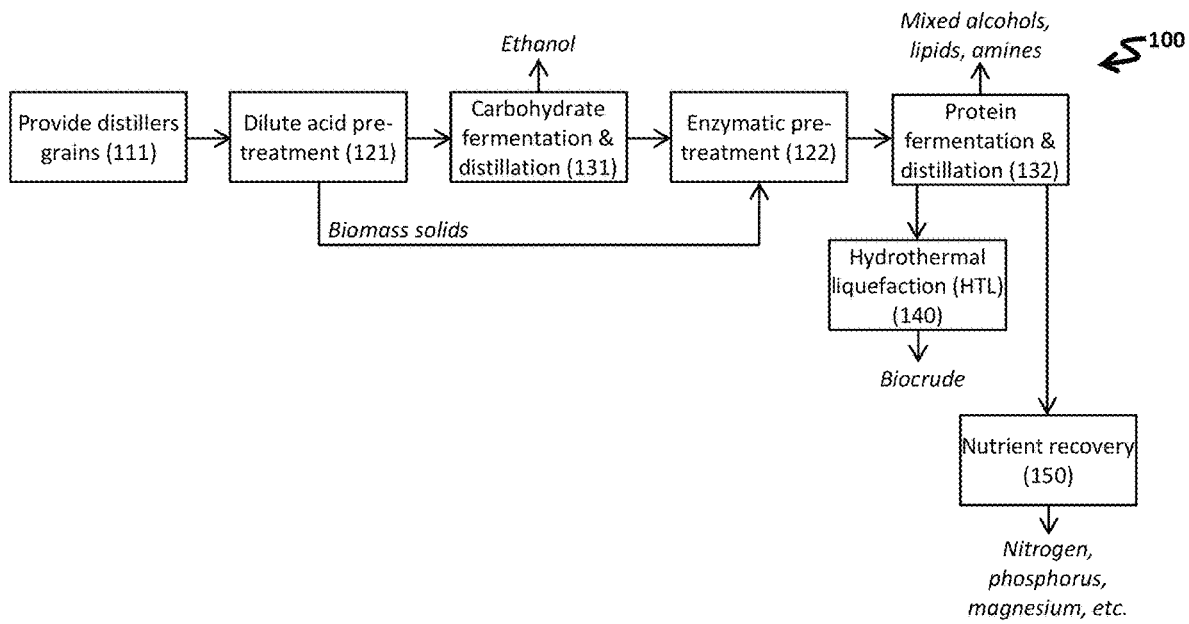

Yet another upgrading process 100 is shown in FIG. 1B, which provides a pre-treatment step 121,122 prior to each fermentation step 131,132. Overall, the exemplary non-limiting process 100 includes providing 111 a biomass (e.g., distillers' grain); pre-treating 121 the biomass (e.g., with a dilute acid pre-treatment) and optionally separating a biomass solid; fermenting 131 the carbohydrate fraction (e.g., including one or more sugars) of the biocomponents with a genetically engineered organism useful for degrading carbohydrates (e.g., thereby producing ethanol) with optional distillation (e.g., of the produced ethanol); pre-treating 122 the biomass (e.g., with one or more enzymes); fermenting 132 the protein fraction (e.g., including one or more proteins, peptides, and/or amino acids) of the biocomponents with a genetically engineered organism useful for degrading amino acids (e.g., thereby producing one or more mixed alcohols, lipids, amino acids, and/or amines) with optional distillation (e.g., of the produced mixed alcohols); liquefying 140 any residual or fraction of a fermentation product (e.g., by way of hydrothermal liquefaction, thereby producing a biocrude); and recovering 150 any residual or fraction of a fermentation product (e.g., thereby producing a nutrient, such as nitrogen, phosphorous, magnesium etc.).

Pre-treatment can be employed to release various biocomponents from biomass that can be difficult to process. In addition, the process can include separated fermentation steps, in which each step can be optimized or selected to degrade a particular type of biocomponent. As seen in FIG. 1B, the process 100 includes a first fermentation step 131 useful for degrading sugar and carbohydrate components, thereby producing ethanol; and a second fermentation step 132 useful for degrading protein and amino acid components, thereby producing mixed alcohols, amines, and released amino acids.

Each pre-treatment step can be optionally followed by a separation step, such as by separating one or more solid components from a liquid portion. The liquid portion can be further processed (e.g., by fermentation), and the separated solid components can be re-introduced into the process at a later step in the processing pathway (e.g., enzymatic pre-treatment).

Figure 1C:
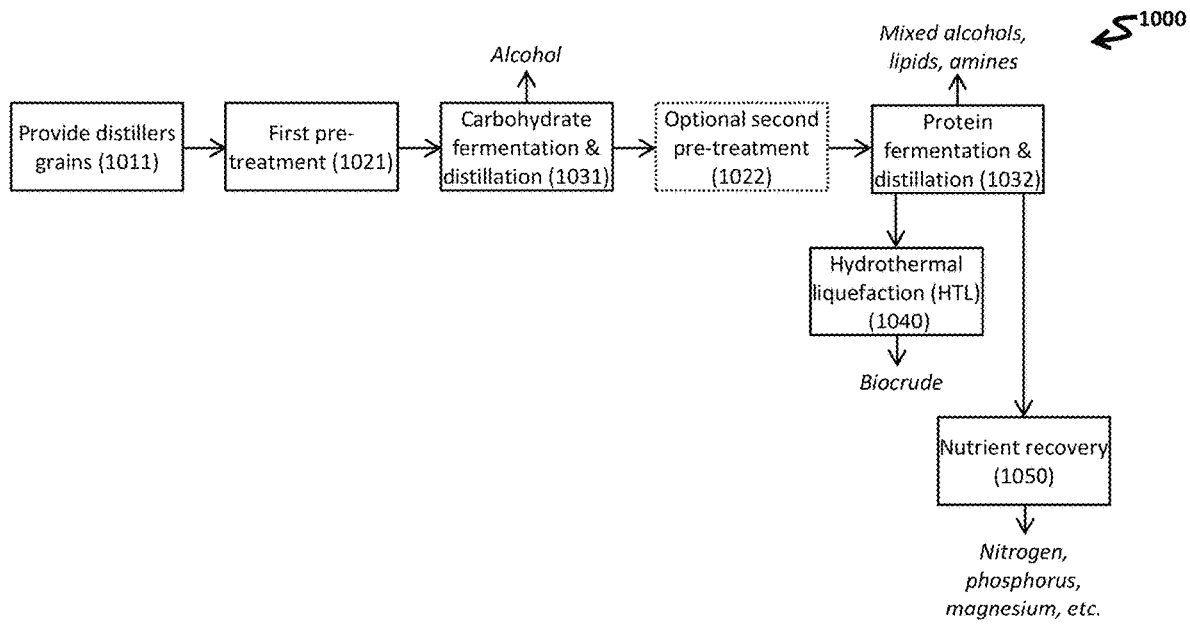

A second pre-treatment step can be optional. FIG. 1C shows another exemplary upgrading process 1000 that includes providing 1011 a biomass (e.g., distillers' grain); pre-treating 1021 the biomass (e.g., with a dilute acid pre-treatment); fermenting 1031 the carbohydrate fraction (e.g., including one or more sugars) with optional distillation (e.g., of the produced ethanol); optionally pre-treating 1022 the biomass (e.g., with one or more enzymes); fermenting 1032 the protein fraction (e.g., including one or more proteins, peptides, and/or amino acids) with optional distillation (e.g., of the produced mixed alcohols); liquefying 1040 any residual or fraction of a fermentation product (e.g., by way of hydrothermal liquefaction, thereby producing a biocrude); and recovering 1050 any residual or fraction of a fermentation product (e.g., thereby producing a nutrient, such as nitrogen, phosphorous, magnesium etc.)

Figure 1D:
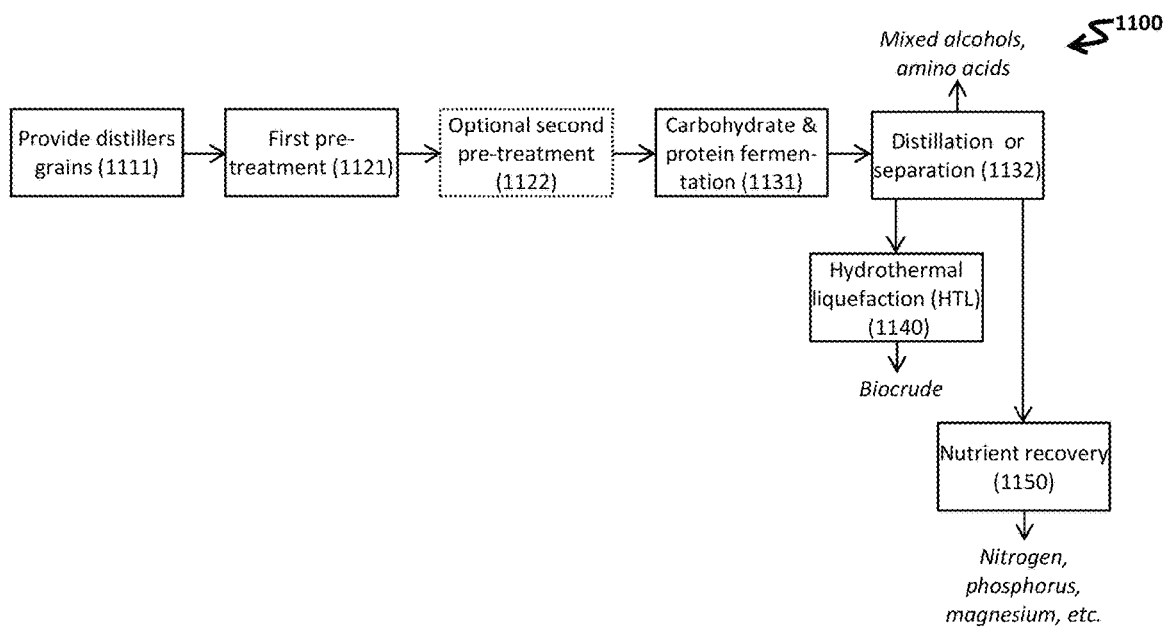

In particular embodiments, the fermentation step can include fermenting two different biocomponents (e.g., carbohydrates and proteins, including amino acids and peptides) within the biomass. In some embodiments, the fermentation step can include use of a co-culture of organisms (e.g., two or more different genetically engineered organisms, such as any described herein). For instance, a first organism can be used to degrade a first biocomponent (e.g., carbohydrates), and a second organism can be used to degrade a different, second biocomponent (e.g., proteins, amino acids, and/or peptides). FIG. 1D shows an exemplary upgrading process 1100 that includes providing 1111 a biomass (e.g., distillers' grain); pre-treating 1121 the biomass with a first pre-treatment (e.g., with a dilute acid pre-treatment); pre-treating 1122 the pre-treated biomass with an optional second pre-treatment (e.g., with one or more enzymes); fermenting 1131 the carbohydrate fraction (e.g., including one or more sugars) and the protein fraction (e.g., including one or more proteins, peptides, and/or amino acids); distillation or separation 1132 (e.g., of the produced ethanol and/or produced amino acids, including high value amino acids); liquefying 1140 any residual or fraction of a fermentation product (e.g., by way of hydrothermal liquefaction, thereby producing a biocrude); and recovering 1150 any residual or fraction of a fermentation product (e.g., thereby producing a nutrient, such as nitrogen, phosphorous, magnesium etc.)

Figure 1E:
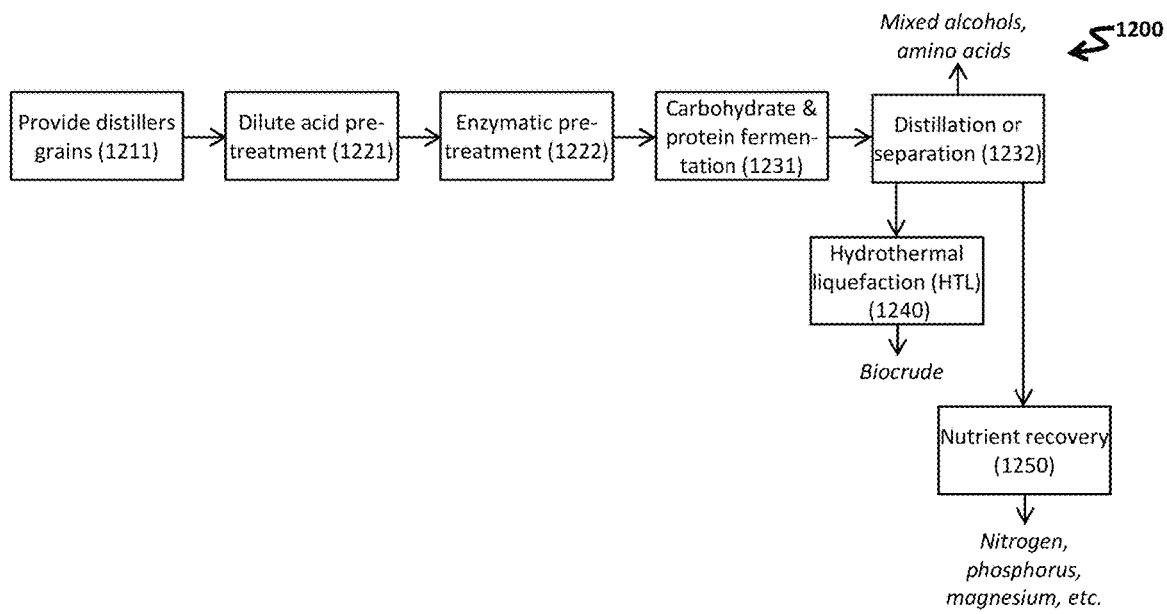

Two pre-treatment steps can be employed to break down components of the biomass. FIG. 1E shows an exemplary upgrading process 1200 that includes providing 1211 a biomass (e.g., distillers' grain); pre-treating 1221 the biomass with a first pre-treatment (e.g., with a dilute acid pre-treatment); pre-treating 1222 the pre-treated biomass with a second pre-treatment (e.g., with one or more enzymes); fermenting 1231 the carbohydrate fraction (e.g., including one or more sugars) and the protein fraction (e.g., including one or more proteins, peptides, and/or amino acids); distillation or separation 1232 (e.g., of the produced ethanol and/or produced amino acids, including high value amino acids); liquefying 1240 any residual or fraction of a fermentation product (e.g., by way of hydrothermal liquefaction, thereby producing a biocrude); and recovering 1250 any residual or fraction of a fermentation product (e.g., thereby producing a nutrient, such as nitrogen, phosphorous, magnesium etc.)

Figure 2A:
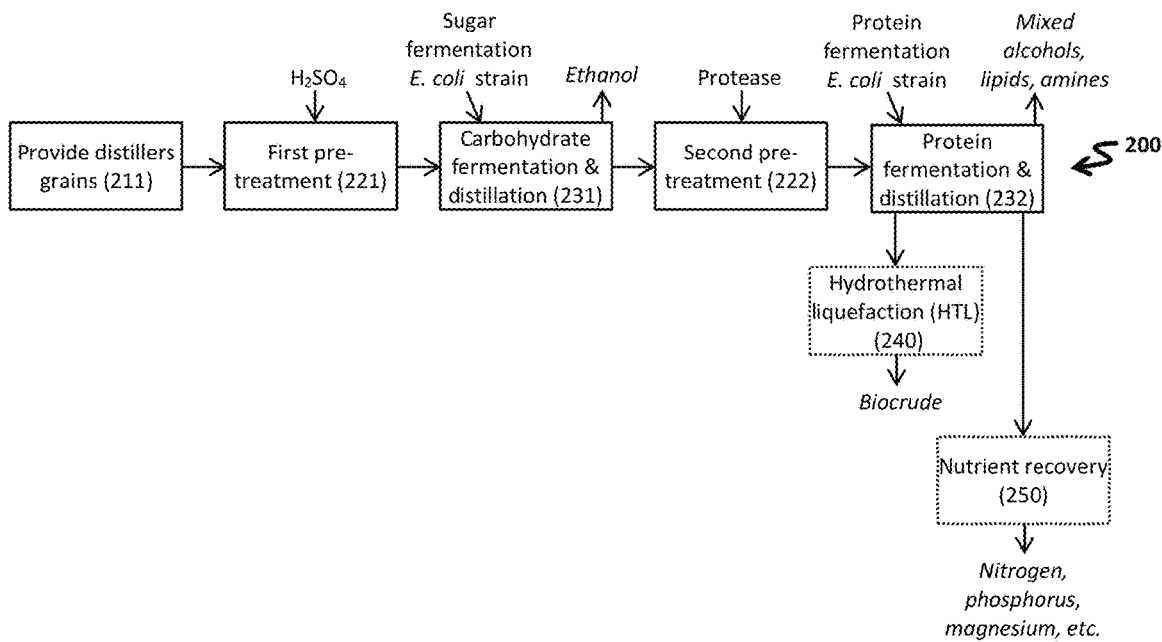
FIG. 2A-2B shows other exemplary process flow diagrams. Provided is (A) an exemplary process 200 including inputs and outputs designated by arrows leading either into or away from a box, respectively; and (B) another exemplary process 2000 including inputs and outputs designated by arrows leading either into or away from a box, respectively

Another exemplary conversion process 200 is shown in FIG. 2A, which provides various inputs and outputs during the process. As can be seen, the process 200 includes a first step of providing 211 a biomass (e.g., distillers' grain), which can then be pre-treated 221. This pre-treatment step 221 can include any useful input, e.g., water, one or more acids (e.g., dilute or strong $H_2SO_4$), a neutralizer (e.g., a base, such as NaOH), and/or one or more enzymes (e.g., a protease or a protease cocktail). The fermentation step 231 results in conversion of carbohydrates into one or more smaller or simpler components (e.g., alcohols) by employing an organism strain useful for sugar fermentation. A second pretreatment step 222 generally includes one or more enzymes, and a second fermentation step 232 results in conversion of proteins into one or more smaller or simpler components (e.g., alcohols, amino acids, ketoacids, and/or amines) by employing an organism strain useful for protein fermentation. Such smaller or simpler components can be further purified (e.g., extracted, distilled, precipitated, etc.) to provide pharmaceutical intermediates, chemicals, chemical/biochemical precursors, building blocks, reagents, and/or intermediates.

A distillation step (e.g., conducted after one fermentation step or after each fermentation step) can result in the separation of volatile fraction(s) from the less volatile fraction(s), resulting in, e.g., a fraction including one or more alcohols or mixtures thereof, and another fraction including a predominantly non-aqueous, lipid phase (e.g., a bioresidue). The fraction including alcohol(s) can be further purified to provide bioethanol.

Optionally, the bioresidue can be thermally treated at a temperature sufficient to separate volatile lipids from solid residuals, such as by way of hydrothermal liquefaction 240, to produce a liquefied mixture. This liquefied mixture can include biocrude oil, ash, biochar, and other components. The biocrude oil, in turn, can be further processed, e.g., by way of hydrotreatment with an input of hydrogen, to produce any useful biofuel, such as biodiesel, naphtha, or light hydrocarbons. Other components from the liquefied mixture can be phase separated to extract the solid residuals. This liquid phase can be further processed for nutrient and water recovery 250.

Figure 2B:
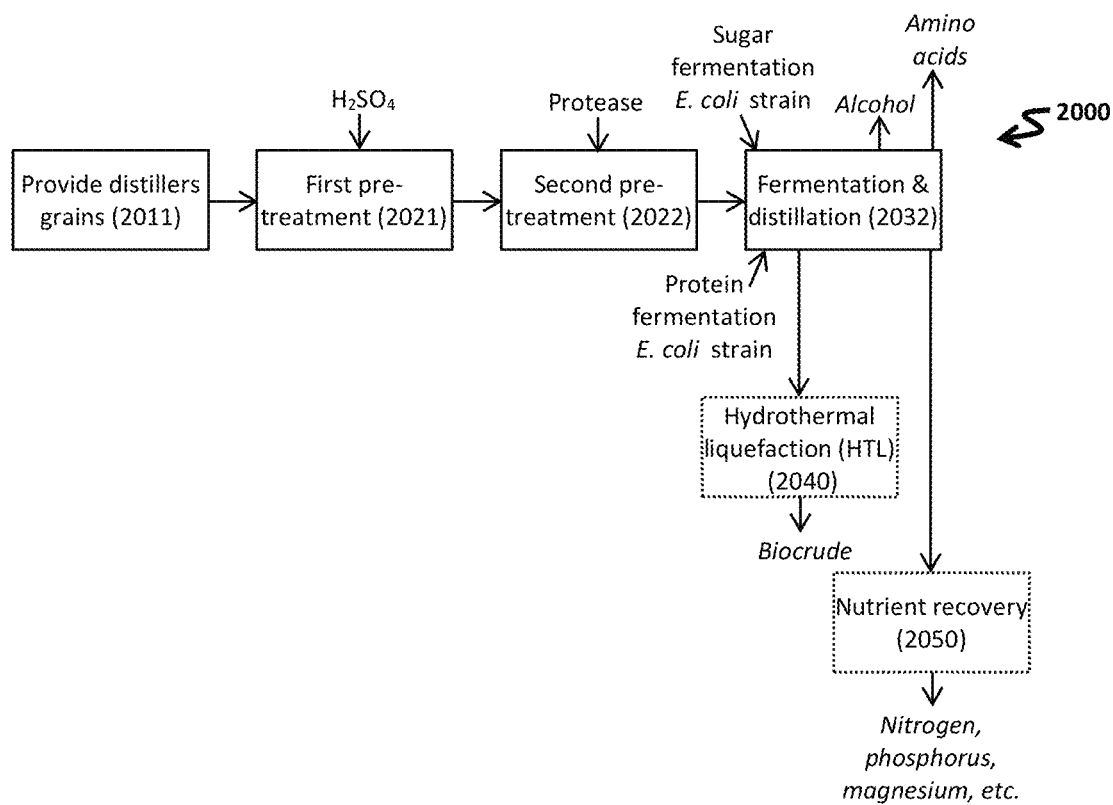

Yet another exemplary conversion process 2000 is shown in FIG. 2B, which provides various inputs and outputs during the process. As can be seen, the process 2000 includes a first step of providing 2011 a biomass (e.g., distillers' grain), which can then be pre-treated 2021. This pre-treatment step 2021 can include any useful input, e.g., water, one or more acids (e.g., dilute or strong $H_2SO_4$) and a neutralizer (e.g., a base, such as NaOH). The process can include a second pre-treatment step 2022, which can include any useful input, e.g., water, buffer, and/or one or more enzymes (e.g., a protease or a protease cocktail). The fermentation step 2032 results in conversion of carbohydrates into one or more smaller or simpler components (e.g., alcohols) and proteins into one or more smaller or simpler components (e.g., alcohols, amino acids, ketoacids, and/or amines). The fermentation step can employ a first organism strain useful for sugar fermentation and a second organism strain useful for protein fermentation. Such smaller or simpler components can be further purified (e.g., extracted, distilled, precipitated, lyophilized, etc.) to provide pharmaceutical intermediates, chemicals, chemical/biochemical precursors, building blocks, amino acids, reagents, and/or intermediates.

Optionally, the bioresidue can be thermally treated at a temperature sufficient to separate volatile lipids from solid residuals, such as by way of hydrothermal liquefaction 2040, to produce a liquefied mixture (e.g., any described herein). Other components from the liquefied mixture can be phase separated to extract the solid residuals, and this liquid phase can be further processed for nutrient and water recovery 2050.

Any useful biomass can be employed. Exemplary biomass include distillers' grains or co-products (e.g., wet distillers' grains (WDGs), dried distillers' grains (DDGs), dried distillers' grains with solubles (DDGS), fatty acids from oil hydrolysis, lipids from evaporation of thin stillage, syrup, distillers' grains, distillers' grains with or without solubles, solids from a mash before fermentation, solids from a whole stillage after fermentation, biodiesel, and acyl glycerides), oilseed meals (e.g., soybean meal or canola meal), feeds (e.g., alfalfa meal, cottonseed meal, DDGS, rice bran, or wheat bran), yeast (e.g., extracts), algae (e.g., *Nannochloropsis*, wastewater algae, or any described herein), cereal by-products (e.g., whey), etc. Additional exemplary biomass are described in Liu F et al., "Engineering microbial consortia for bioconversion of multisubstrate biomass streams to biofuels," Chapter 7 (pp. 101-120) in *Biofuels: Challenges and opportunities* (M. Al Qubeissi, ed.), IntechOpen (London, United Kingdom), 2019.

Pre-Treatment of the Biomass

Pre-treatment can be used to convert constituents within the biomass into various biocomponents (e.g., proteins, carbohydrates, fatty acids, and/or lipids). Such biocomponents can be pre-treated to obtain more solubilized or hydrolyzed constituents, such as amino acids or sugars (e.g., glucose). For instance, carbohydrates within the biomass can be pre-treated and, thereby, be converted into a sugar and/or an alcohol, such as glucose, fucose, galactose, xylose, mannose, mannitol, ethanol, butanol, and/or pentanol. In another instance, proteins within the biomass can be treated and, thereby, hydrolyzed and converted into amino acids. Such amino acids, in turn, can be fermented to produce one or more mixed alcohols and amines. In addition, one or more extraction techniques can be applied to separate the protein/carbohydrate fraction from other constituents. Such extraction techniques can include, e.g., use of one or more ionic liquids to selectively extract a particular fraction.

Pre-treatment can include the use of one or more acids, bases, oxidizers, reducers, and/or enzymes. Exemplary pre-treatment conditions include strong and/or dilute acid hydrolysis (e.g., with $H_2SO_4$ and/or HCl), base hydrolysis or neutralization (e.g., with NaOH), heat treatment, sonication, and/or enzyme degradation (e.g., with one or more proteases, such as endoproteases, exoproteases, serine proteases (e.g., subtilisin, also known as alcalase), aminopeptidases, carboxypeptidases, endoglucanases, cellobiohydrolases, glycoside hydrolases (e.g., lysozyme), endoglucanases, glucanases, endoxyalanases, pectinases, sulfatases (e.g., arylsulfatases), cellulases, xylanases, as well as mixtures thereof, such that available as commercially available Pronase®, a mixture of proteolytic enzymes that are produced in the culture supernatant of *Streptomyces griseus* K-1).

Fermentation

Fermentation conditions generally include the use of one or more organisms to convert starting reactants (e.g., biocomponents, such as carbohydrates, proteins, sugars, amino acids, etc.) into alcohol and other co-products. Fermentation can include degradation of carbohydrates into alcohol in the presence of one or more organisms. Such conditions can also release mixed alcohols and nitrogen from degradation of protein, which can contain up to about 90% of the nitrogen in a biomass. In this manner, fermentation provides useful biofuels and intermediates (e.g., alcohols). Furthermore, released nitrogen can be recovered and recycled.

For fermentation, any useful organisms can be employed, such as one or more bacteria (e.g., *Escherichia*, such as *E. coli*; *Zymobacter*, such as *Z. palmae*; or *Zymomonas*, such as *Z. mobilis*) and one or more yeast (e.g., *Saccharomyces*, such as *S. cerevisiae*), including mutant forms thereof, including those that deaminate protein hydrolysates (e.g., into ketoacids, tricarboxylic acid cycle intermediates, etc.), that convert proteins to alcohols (e.g., to C4 or C5 alcohols), and/or that lack one or more quorum-sensing genes (e.g., genes luxS or lsrA), such as those described in Atsumi S et al., "Non-fermentative pathways for synthesis of branched-chain higher alcohols as biofuels,"*Nature* 2008; 451:86-90; and Huo Y X et al., "Conversion of proteins into biofuels by engineering nitrogen flux," *Nat. Biotechnol.* 2011; 29(4): 346-51, which is incorporated herein by reference in its entirety; yeast (e.g., *Saccharomyces*, such as *S. cerevisiae* and *S. uvarum*); and fungi (e.g., *Aspergillus*, such as *A. niger*, *A. terreus*, and *A. fumigatus*).

In one instance, fermentation is conducted in the presence of one or more organisms useful for sugar or carbohydrate fermentation. Such organisms can include those selected by directed evolution to employ any useful sugar substrate, to have enhanced alcohol tolerance, and/or to have increased activity. Exemplary organisms include *E. coli* KO11, *E. coli* LY01, *E. coli* SZ110, *E. coli* LY168, *Z. mobilis mobilis* AX101, *S. cerevisiae* 424A(LNH-ST), and *S. cerevisiae* ATCC 96581.

In particular embodiments, such organisms (e.g., an organism from the genus *Escherichia*) can express one or more exogenous proteins that facilitate sugar or carbohydrate fermentation (e.g., by employing one or more exogenous nucleic acid sequences, such as in one or more expression vectors, that encode for one or more exogenous proteins). Exemplary exogenous proteins can include an exogenous acetolactate synthase, which converts pyruvate into acetolactate. Non-limiting acetolactate synthases include *B. subtilis* acetolactate synthase AlsS (FIG. 24A, SEQ ID NO:50), *B. subtilis* (strain 168) acetolactate synthase AlsS (FIG. 24B, SEQ ID NO:51), *Klebsiella pneumoniae* acetolactate synthase BudB (FIG. 24C, SEQ ID NO:52), and *Lactococcus lactis* alpha-acetolactate synthase Als (FIG. 24D, SEQ ID NO:53).

Expression of such acetolactate synthase can be accompanied by any other protein useful for carbohydrate degradation. In particular embodiments, such proteins can include, e.g., a ketol-acid reductoisomerase, such as any described herein (e.g., IlvC, such as in FIG. 11A-11B); a dihydroxyacid dehydratase, such as any described herein (e.g., IlvD, such as *E. coli* MG1655 dihydroxyacid dehydratase IlvD (FIG. 24E, SEQ ID NO:54)); or a bifunctional acetohydroxybutanoate synthase/acetolactate synthase, e.g., IlvH. Use of such accompaniment proteins can facilitate conversion of pyruvate into KIV (2-ketoisovalerate).

Conversion of KIV into alcohols can include use of other exogenous protein(s), such as one or more decarboxylases and dehydrogenases. Exemplary other exogenous protein(s) can include a 2-ketoacid decarboxylase (Kdc), such as any described herein (e.g., *Lactococcus lactis* 2-ketoacid decarboxylase Kdc (FIG. 24F, SEQ ID NO:55), *Lactococcus lactis* branched-chain alpha-ketoacid decarboxylase KdcA (FIG. 24G, SEQ ID NO:56), *Salmonella typhimurium* (strain LT2/SGSC1412/ATCC 700720) indolepyruvate decarboxylase (FIG. 24H, SEQ ID NO:57), and *Clostridium acetobutylicum* pyruvate decarboxylase (FIG. 24I, SEQ ID NO:58); and an alcohol dehydrogenase, such as any described herein (e.g., YqhD, such as in FIG. 10C-G).

In another instance, fermentation is conducted in the presence of one or more organisms useful for protein fermentation. Such organism can include those selected by directed evolution to switch cofactor specificity, to deaminate protein hydrolysates, and/or to reduce competing pathways. Exemplary organisms include those having mutants forms of one or more enzymes, such as YqhD and/or IlvC mutants to switch cofactor specificity, transhydrogenase overexpression in *E. coli* PntAB, alcohol dehydrogenase mutants (e.g., mutants of AdhE, AdhP, EutG, YiaY, YqhD, and/or YjgB), and/or ketol-acid isomerase mutants (e.g., mutants of IlvC, IlvD, IlvH, and/or IlvA), as well as any described in Brinkmann-Chen S et al., "General approach to reversing ketol-acid reductoisomerase cofactor dependence from NADPH to NADH," *Proc. Nat'l Acad. Sci. USA* 2013; 110(27):10946-51; and Bastian S et al., "Engineered ketol-acid reductoisomerase and alcohol dehydrogenase enable anaerobic 2-methylpropan-1-ol production at theoretical yield in *Escherichia coli*," *Metab. Eng.* 2011; 13(3):345-52, each of which is incorporated herein by reference in its entirety.

Exemplary mutants include a YqhD mutant (e.g., a mutant having a polypeptide sequence with at least one amino acid substitution, as compared to wild-type YqhD (e.g., such as SEQ ID NO:1 in FIG. 10C). In one non-limiting example, the YqhD mutant has a polypeptide sequence of SEQ ID NO:2 (FIG. 10D), or a fragment thereof, in which Xaa at position 39 is Ile, Tyr, Val, Leu, Phe, or any other conservative amino acid substitution described herein. In another non-limiting example, the YqhD mutant has a polypeptide sequence of SEQ ID NO:3 (FIG. 10E), or a fragment thereof, in which Xaa at position 40 is Pro, Arg, His, Lys, Trp or any other conservative amino acid substitution described herein.

In yet another non-limiting example, the YqhD mutant has a polypeptide sequence of SEQ ID NO:4 (FIG. 10F), or a fragment thereof, in which Xaa at position 39 is Ile, Tyr, Val, Leu, Phe, or any other conservative amino acid substitution described herein; and in which Xaa at position 40 is Pro, Arg, His, Lys, Trp or any other conservative amino acid substitution described herein. In another embodiment, the mutant includes Ile at position 39 and Arg at position 40; Ile at position 39 and Lys at position 40; Ile at position 39 and His at position 40; Val at position 39 and Arg at position 40; Val at position 39 and Lys at position 40; Val at position 39 and His at position 40; Leu at position 39 and Arg at position 40; Leu at position 39 and Lys at position 40; Leu at position 39 and His at position 40; Tyr at position 39 and His at position 40; Phe at position 39 and His at position 40; Phe at position 39 and Lys at position 40; Phe at position 39 and Arg at position 40; Trp at position 39 and Arg at position 40; Trp at position 39 and Lys at position 40; Trp at position 39 and His at position 40; Ser at position 39 and His at position 40; or Ser at position 39 and Thr at position 40.

In another non-limiting example, the YqhD mutant has a polypeptide sequence of SEQ ID NO:5 (FIG. 10G), or a fragment thereof, in which one or more amino acid substitutions are present at positions 37, 38, 39, and/or 40. In one embodiment, the mutant includes one of the following amino acids, independently, at position 37, 38, and 39: Gly, Ile, Tyr, Val, Leu, Phe, or any other conservative amino acid substitution described herein. In another embodiment, the mutant includes one of the following amino acids at position 40: Ser, Pro, Arg, His, Lys, Trp, or any other conservative amino acid substitution described herein.

Other exemplary mutants include an IlvC mutant (e.g., a mutant having a polypeptide sequence with at least one amino acid substitution, as compared to wild-type IlvC (e.g., such as SEQ ID NO:6 in FIG. 11A). In one non-limiting embodiment, the IlvC mutant has a polypeptide sequence of SEQ ID NO:7 (FIG. 11B), or a fragment thereof, in which one or more amino acid substitutions are present at positions 71, 76, 78, 110, 146, 185, and/or 433.

The mutants can have any useful characteristic provided during selective evolution. In one non-limiting instance, the mutant can have increased reactivity with nicotinamide adenine dinucleotide (NADH), as compared to a wild-type reference protein. In another instance, the mutant can have increased reactivity NADH over nicotinamide adenine dinucleotide phosphate (NADPH), as compared to a wild-type reference protein. In yet another instance, the mutant can have increased specificity for NADH over NADPH, as compared to a wild-type reference protein.

Figure 3A:
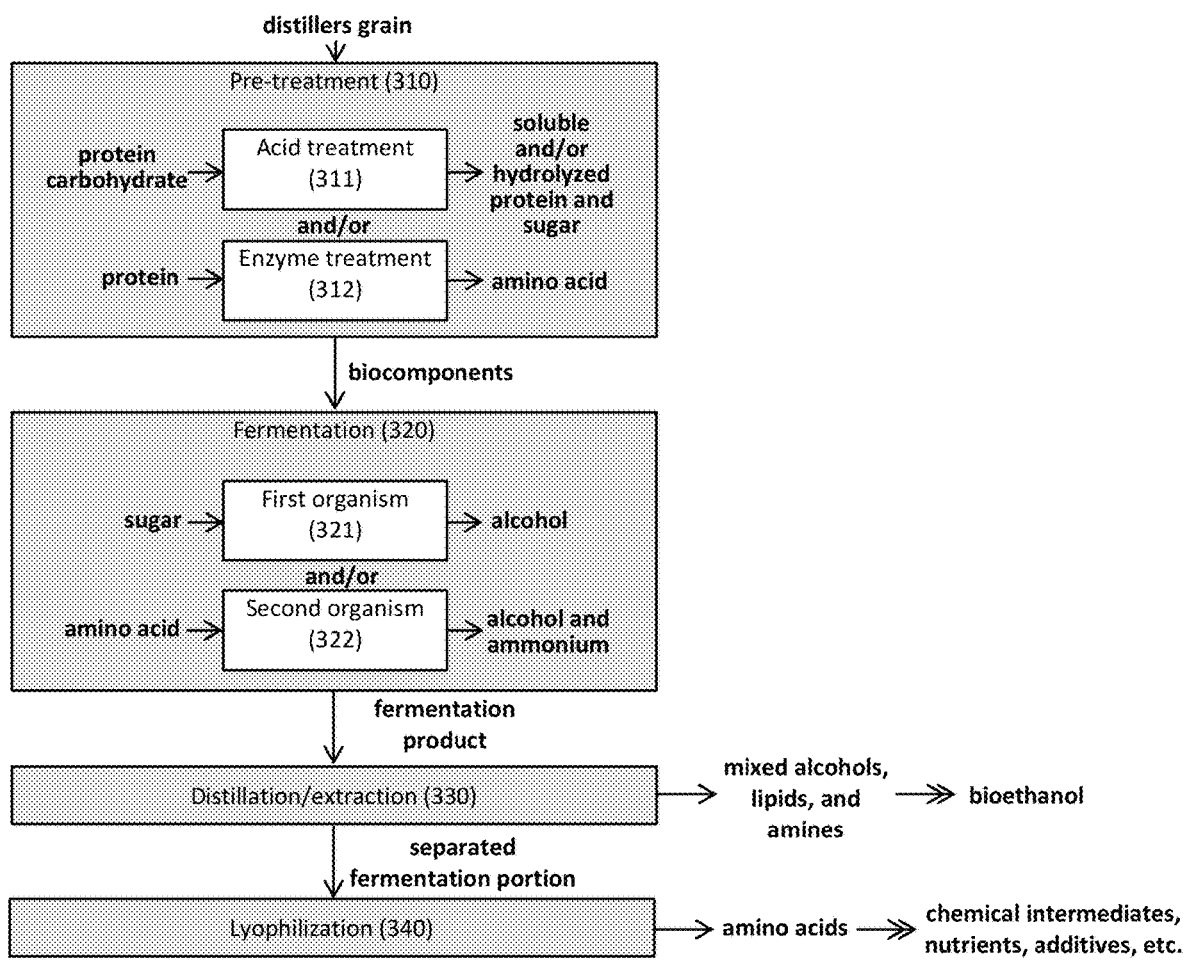
FIG. 3A-3E shows exemplary processes with various sub-steps. Provided are (A) an exemplary process including sub-steps for the pre-treatment 310 and fermentation 320 steps; (B) an exemplary process including a distillation/extraction step 3005 between the pre-treatment 3003 and fermentation 3004 steps; (C) another exemplary process including a first pre-treatment step 3103 and a subsequent distillation/extraction step 3105 to separate a biomass solid (e.g., a bioresidue); (D) yet another exemplary process including distillation/extraction steps 3505,3605 subsequent to each fermentation step 3504,3604; and (E) a further exemplary process including sub-steps for the pre-treatment 410 step and use of sub-steps or a co-culture for the fermentation 420 step.

FIG. 3A shows a portion of an exemplary process including a pre-treatment step 310, a fermentation step 320, a distillation/extraction step 330, and a lyophilization step 340. Each of these steps, in turn, can include one or more other sub-steps. For instance, pre-treatment 310 can include acid treatment 311 in order to degrade proteins and carbohydrates into soluble and/or hydrolyzed protein and sugar; as well as enzyme treatment 312 in order to degrade proteins into amino acids. Each of these components (e.g., proteins, carbohydrates, sugars, amino acids, etc.) obtained from the pre-treatment step is considered a biocomponent. In some instances, pre-treatment 310 results in solubilization of useful biocomponents, as well as separation of biomass solids.

Fermentation can include use of one or more organisms configured to facilitate degradation (e.g., specific or non-specific degradation) of one or more biocomponents. As can be seen, an exemplary fermentation step 320 includes use of at least two organisms, in which a first organism 321 is useful for degradation of sugar into alcohol and in which a second organism 322 is useful for degradation of amino acid into an alcohol (e.g., $R^4OH$, in which $R^4$ is an optionally substituted alkyl, such as an optionally substituted $C_{2-10}$ alkyl) and an amine (e.g., $N^+R^1R^2R^3R^4$ or $NR^1R^2R^3$, in which each of $R^1$, $R^2$, $R^3$, and $R^4$ is, independently, H or an optionally substituted alkyl). The fermentation step 320 results in a fermentation product, which can include a mixture of alcohols, amino acids, amines, and/or lipids.

Figure 8:
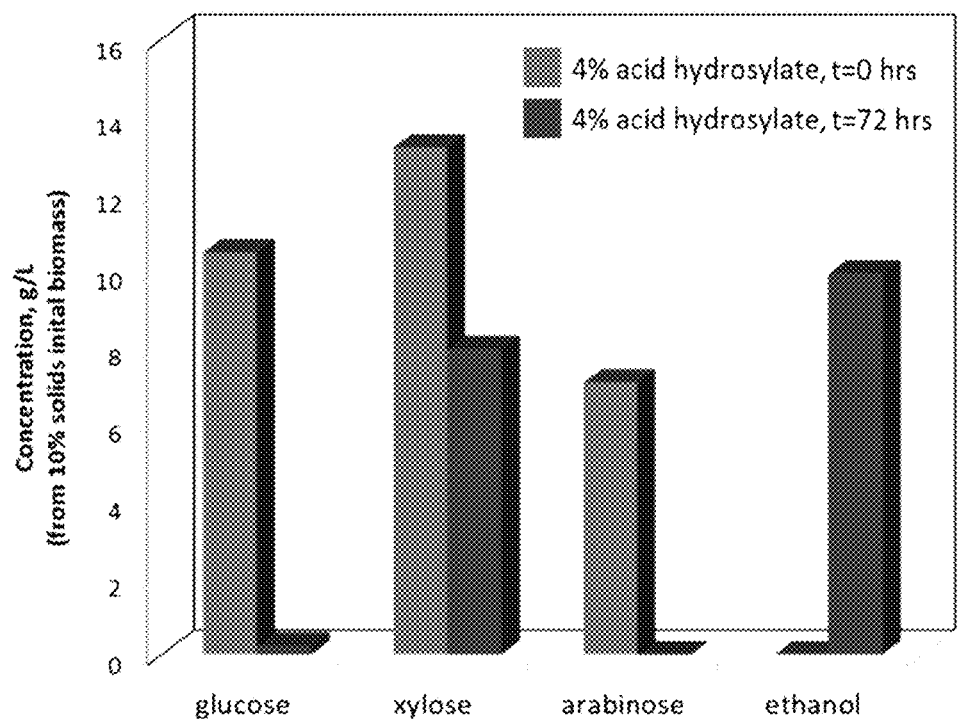
FIG. 8 shows carbohydrate hydrolysis and ethanol yields, in which the process included dilute acid pre-treatment and fermentation.
Figure 9:
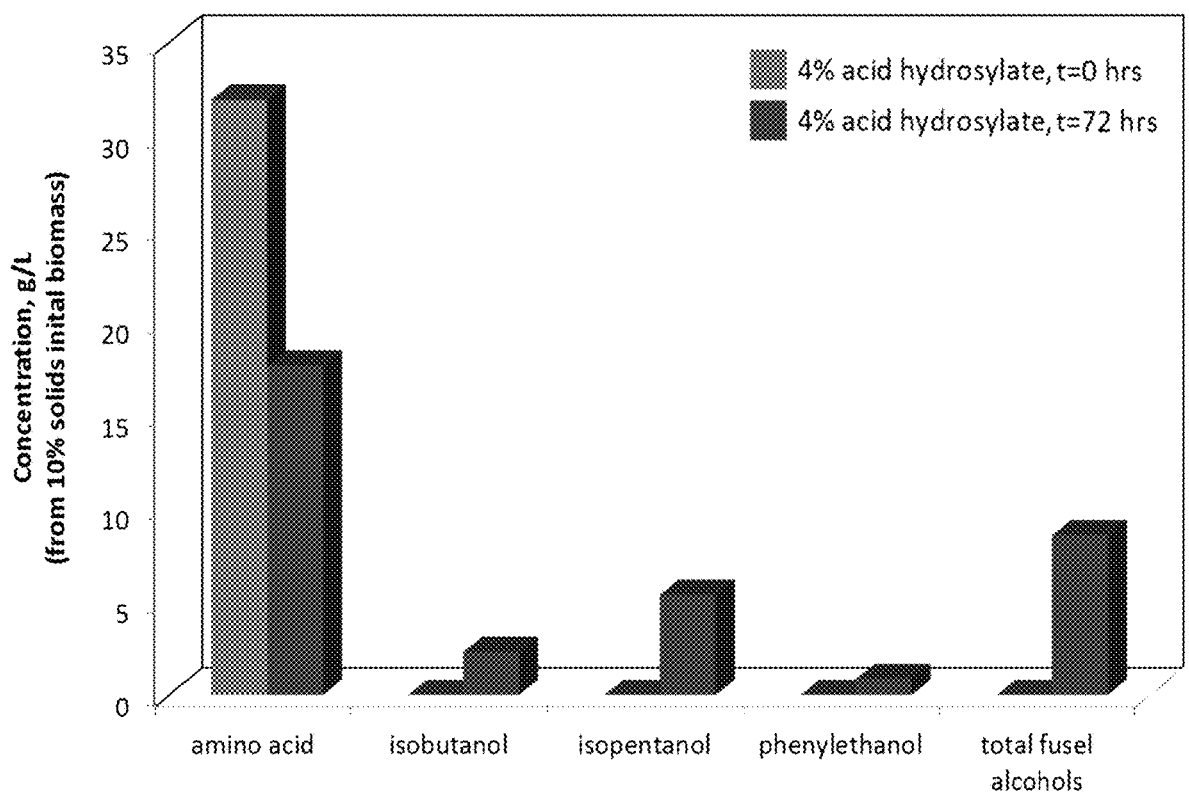
FIG. 9 shows protein hydrolysis and fusel alcohol yields, in which the process included dilute acid pre-treatment, enzymatic pre-treatment (e.g., protease digestion), and fermentation.

After distillation/extraction 330, various fractions of the mixture can be separated into different components, including a first fraction including mostly lipids and lipid products (e.g., a bioresidue); a second fraction including mixed alcohols and, optionally, neutral lipids; and a third fraction including amines and/or amino acids. The first fraction can be further processed (e.g., by way of liquefaction and/or pyrolysis) to produce a biocrude oil, which can be treated to form a biofuel. The second fraction can be further purified into, e.g., bioethanol. The third fraction can be further processed to isolate high-value amino acids. In some embodiments, the pre-treatment and fermentation conditions herein can provide enhanced alcohol yield (see, e.g., FIG. 8), as well as enhanced amino acid degradation and enhanced fusel alcohol yield (FIG. 9).

The pre-treatment, distillation/extraction, and fermentation steps can be conducted in any useful order. For instance, the fermentation step can be conducted prior to distillation/extraction, meaning that lipids, proteins, and carbohydrates, as well as derived components thereof, are present during fermentation.

Figure 3B:
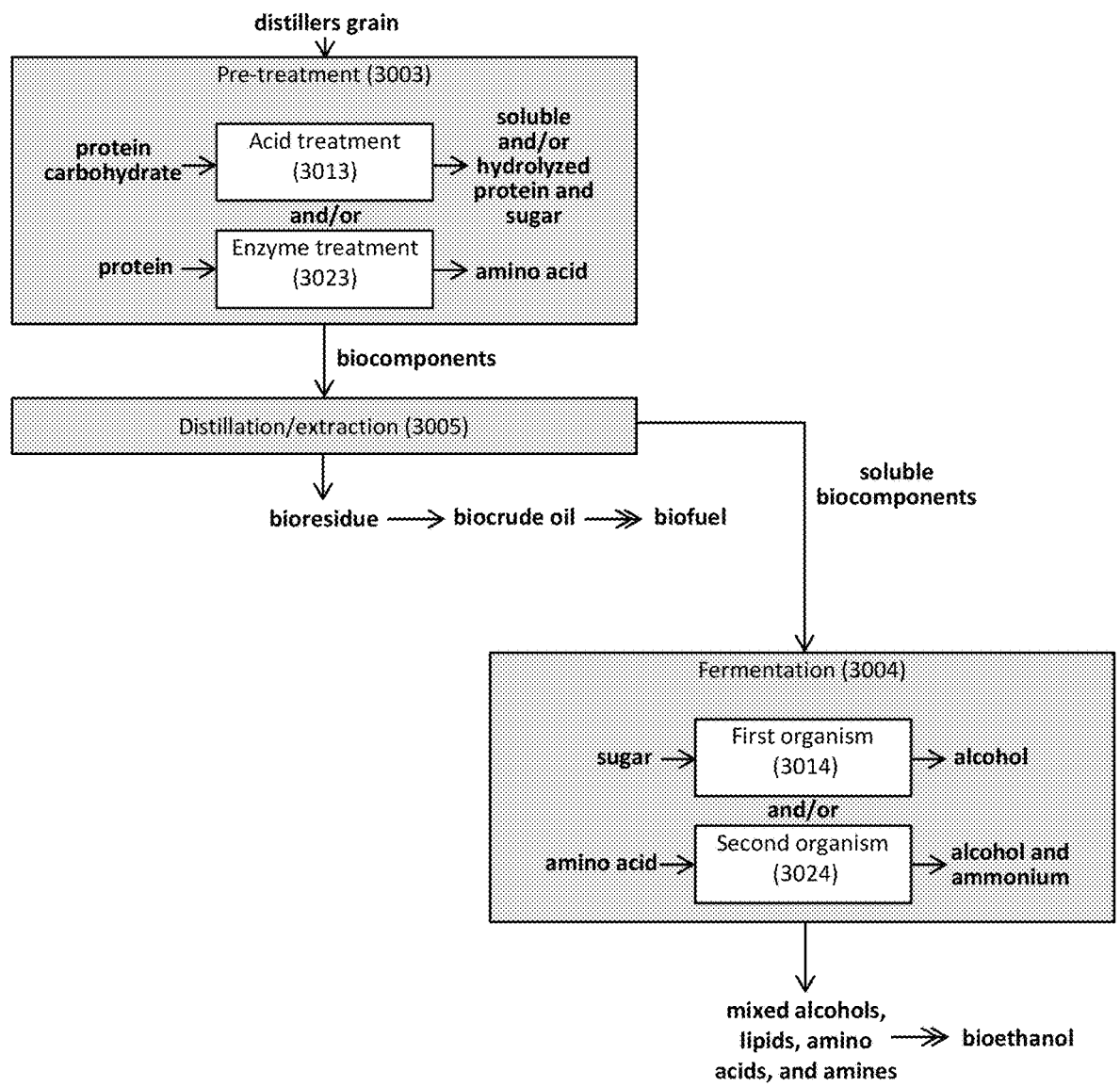

Alternatively, the distillation/extraction step can be conducted prior to fermentation, meaning that the lipid fraction will be omitted from the fermentation step. FIG. 3B shows a portion of an exemplary process including a pre-treatment step 3003, a distillation/extraction step 3005, and a fermentation step 3004. Pre-treatment 3003 can include the sub-steps of acid treatment 3013 in order to degrade proteins and carbohydrates into soluble and/or hydrolyzed protein and sugar; as well as enzyme treatment 3023 in order to degrade proteins into amino acids, thereby providing one or more biocomponents.

Next, a distillation/extraction 3005 step is conducted to provide a first fraction including mostly lipids and lipid products (e.g., a bioresidue) and a second fraction including soluble biocomponents. The first fraction can be further processed (e.g., by way of liquefaction and/or pyrolysis) to produce a biocrude oil, which can be treated to form a biofuel. The second fraction can be fermented and further purified into, e.g., bioethanol. As can be seen, an exemplary fermentation step 3004 includes use of at least two organisms, in which a first organism 3014 is useful for degradation of sugar into alcohol and in which a second organism 3024 is useful for degradation of amino acid into alcohol and an amine (e.g., including ammonium).

Figure 3C:
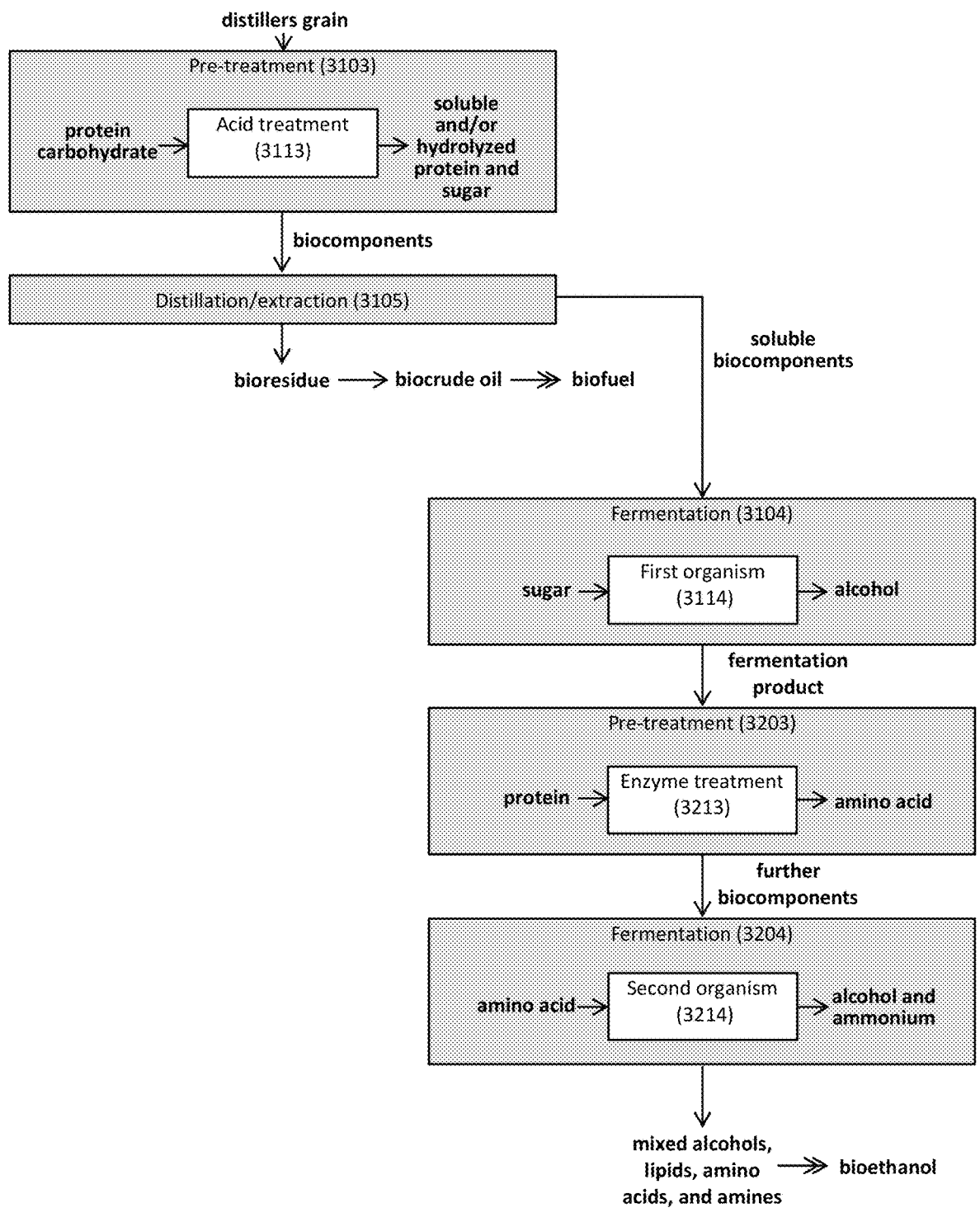

The process can include a pre-treatment step that precedes each fermentation step. FIG. 3C shows a portion of an exemplary process including a first pre-treatment step 3103, a distillation/extraction step 3105, and a first fermentation step 3104. Pre-treatment 3103 can include acid treatment 3113 in order to degrade proteins and carbohydrates into soluble and/or hydrolyzed protein and sugar, followed by fermentation 3104 with a first organism 3114 that is useful for degradation of sugar into alcohol.

The process can be followed by a second pre-treatment step 3203 and a second fermentation step 3214. Pre-treatment 3203 can include enzyme treatment 3213 in order to degrade proteins into amino acids, thereby providing one or more biocomponent, followed by fermentation 3204 with a second organism 3214 that is useful for degradation of amino acid into alcohol and an amine (e.g., an ammonium).

Figure 3D:
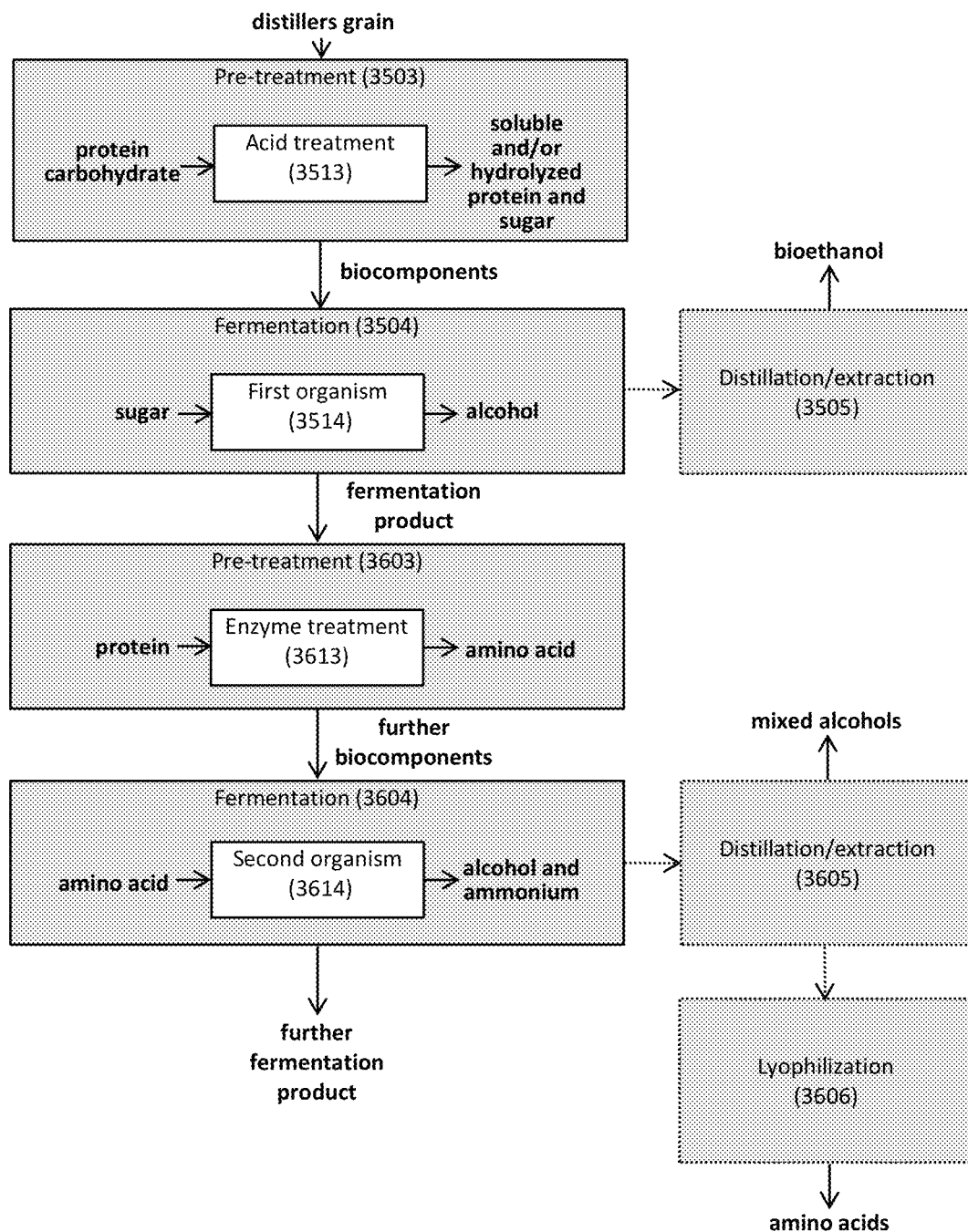

Distillation/extraction steps can be conducted at any useful time during the process. FIG. 3D shows a portion of an exemplary process including a first pre-treatment step 3503, a first fermentation step 3504, a second pre-treatment step 3603, and a second fermentation step 3604.

Pre-treatment steps 3503,3603 can include acid treatment 3513 in order to degrade proteins and carbohydrates into soluble and/or hydrolyzed protein and sugar; or enzyme treatment 3613 in order to degrade proteins into amino acids. Fermentation steps 3504,3604 can include use of a first organism 3514 that is useful for degradation of sugar into alcohol and a second organism 3614 that is useful for degradation of amino acid into alcohol and an amine (e.g., an ammonium). Optionally, a first distillation/extraction step 3505 can be conducted after the first fermentation step 3504, thereby isolating bioethanol and removing this potentially inhibitory product from the fermentation product. In another example, a second distillation/extraction step 3605 can be conducted after the second fermentation step 3604, thereby isolating mixed alcohols from the fermentation product. In yet another example, a further separation step (e.g., a lyophilization step 3606) can be employed to isolate amino acids from the fermentation product.

Figure 3E:
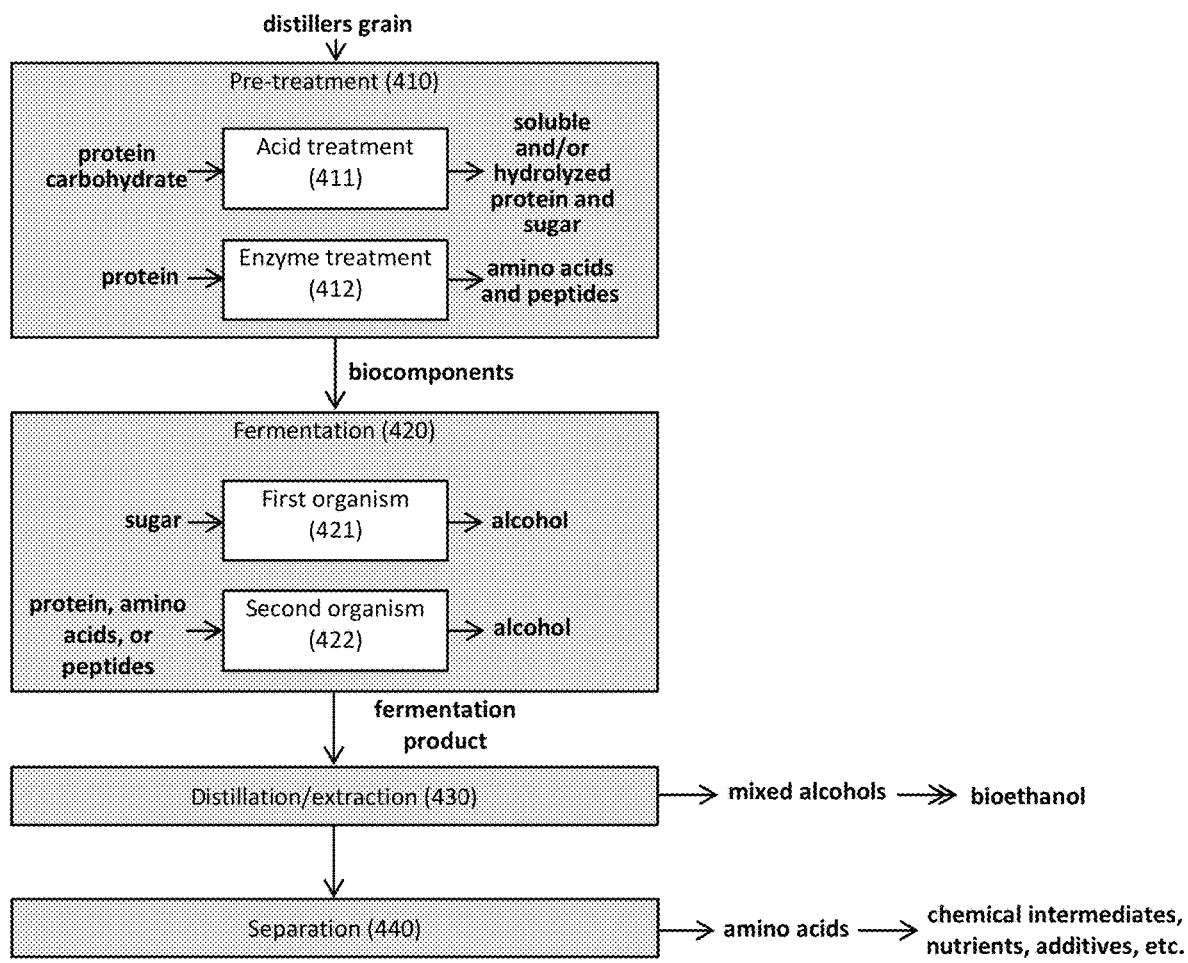

The pre-treatment and fermentation steps can include sub-steps, in which such sub-steps can be performed sequentially or simultaneously. FIG. 3E shows a portion of an exemplary process including a pre-treatment step 410 and a fermentation step 420 with sub-steps. Pre-treatment 410 can include the sub-steps (performed sequentially or simultaneously) of acid treatment 411 in order to degrade proteins and carbohydrates into soluble and/or hydrolyzed protein and sugar; as well as enzyme treatment 412 in order to degrade proteins into amino acids, thereby providing one or more biocomponents. Fermentation 420 can include use of a first organism 421 that is useful for degradation of sugar into alcohol and a second organism 422 that is useful for degradation of amino acid into alcohol and an amine (e.g., an ammonium). Use of such organisms can happen as sequential sub-steps or simultaneous sub-steps (e.g., by use of a co-culture including both the first and second organisms). In some embodiments, the second organism preferentially degrades low value amino acids, thereby leaving non-degraded, high value amino acids (e.g., any described herein) within the fermentation product.

A distillation/extraction step 430 can be conducted after the fermentation step 420, thereby isolating bioethanol. In another example, a separation step 440 can be conducted after the distillation/extraction step 430 to provide a biomass residuum including amino acids (e.g., high value amino acids, such as one or more of valine, glutamic acid, proline, alanine, aspartic acid, tyrosine, glycine, and/or histidine, including salts thereof, in any useful amount, such as any % total value or range of % total values described herein).

Distillation Extraction

The alcohol fermentation products, lipids, and amino acids from the biomass can be captured by distillation and solvent co-extraction. Retaining the lipids through the protein fermentation has been demonstrated to increase yield by reducing product inhibition by phase segregation into lipid microparticles, which can be extracted by lipophilic solvents, such as hexane and ethyl acetate, avoiding high energy fractional distillation of the more than $C_2$ alcohol (e.g., $C_{2-10}$ alcohol) and lipid products.

Any useful distillation and extraction techniques can be employed, including flash extraction, ionic liquid extraction, etc., to isolate one or more biocrude oil, aqueous phases, aqueous co-products, nutrients, etc.

Thermal Conversion, Liquefaction or Pyrolysis

High-temperature treatment (e.g., liquefaction or pyrolysis) can be used to separate or convert particular components of the biomass solids, bioresidue, etc. Exemplary thermal conversion conditions include use of catalysts, use of hydrogen (e.g., in hydrotreatment), use of water (e.g., in liquefaction, including sub-critical or super-critical water), use of aerobic conditions, use of anaerobic conditions (e.g., in pyrolysis), use of high pressure (e.g., of from about 2,000 psi to about 3,000 psi), and/or use of high temperatures (e.g., of from about 200° C. to about 800° C.) to decompose the bioresidue into small molecules, which in turn can react and repolymerize to form oily compounds within a biocrude oil.

In one instance, the thermal conversion condition includes liquefaction, which is generally conducted in the presence of water. By using high temperature and/or high pressure conditions, water becomes a reactive compound that converts the bioresidue into a biocrude oil. Exemplary liquefaction conditions include a wet biomass (e.g., more about 70% moisture), a temperature of from about 200° C. to about 500° C., and a pressure of from about 4 to about 25 MPa.

In another instance, the thermal conversion condition includes pyrolysis, which is generally conducted in the absence of water and in anaerobic conditions. Exemplary pyrolysis conditions include a dry biomass (e.g., less than about 5% moisture), a temperature of from about 200° C. to about 750° C., and a pressure of from about 0.1 to about 0.5 MPa.

Exemplary thermal conversion conditions are described in Ma F et al., "Biodiesel production: a review," *Bioresourc. Technol.* 1999; 70:1-15; Naik S N et al., "Production of first and second generation biofuels: a comprehensive review," *Renew. Sustain. Energy Rev.* 2010; 14:578-97; Raheem A et al., "Thermochemical conversion of microalgal biomass for biofuel production," *Renew. Sustain. Energy Rev.* 2015; 49:990-9; Ringer M et al., "Large-scale pyrolysis oil production: a technology assessment and economic analysis," *National Renewable Energy Laboratory Technical Report NREL/TP*-510-37779, November 2006, 93 pp.; and Schneider R C S et al., "Potential production of biofuel from microalgae biomass produced in wastewater," in *Biodiesel—Feedstocks, Production and Applications*, Prof Zhen Fang (ed.), InTech, 2012, 22 pp., each of which is incorporated herein by reference in its entirety.

Any of the liquefaction steps herein can be replaced by any other thermal conversion step (e.g., pyrolysis) in which high temperature conditions are employed to thermally degrade a bioresidue.

Hydrotreatment

Hydrotreatment is generally used to convert compositions into useful intermediate products or end-use products. Such hydrotreatment generally includes use of high temperatures to institute any useful chemical change, e.g., to break apart triglycerides; to form low molecular weight carbon species, such as optionally substituted alkanes, cycloalkanes, or aryls; to saturate carbon chains with hydrogen; to denitrogenate species; and/or to deoxygenate species to form alkanes, such as n-alkanes. For instance, hydrotreatment can be used to upgrade biocrude oil into biofuels, biochar, or ash; as well as to convert aqueous co-products into biogas. Biocrude oil produced from the post-fermentation residuals by HTL is indicated to have ~50% reduction in nitrogen (primary and secondary amines), thus making it acceptable for hydrotreatment using the existing petrochemical infrastructure.

Hydrotreatment can include isomerization, hydrocracking, distillation, hydrodeoxygenation, catalytic processing (e.g., such as use of one or more catalysts to remove nitrogen, oxygen, and/or sulfur from the biocrude oil under any useful condition, such as a pressure of from about 5 MPa to about 15 MPa and a temperature of from about 200° C. to about 450° C.), liquefaction (e.g., such as hydrothermal liquefaction (HTL) or catalytic liquefaction of a biocrude oil into a biofuel or a biofuel intermediate by use of an operating temperature of from about 100° C. to about 500° C.), transesterification (e.g., treatment of biocrude oil with an alcohol and an optional catalyst to produce methyl ester biodiesel), and/or catalytic hydrothermal gasification (CHG) (e.g., of an aqueous co-product into biogas).

The hydrotreatment process can employ any useful catalyst (e.g., a metal catalyst, such a copper-based catalyst (e.g., CuCr, CuO), a nickel-based catalyst (e.g., NiMo), a ruthenium-based catalyst, a palladium-based catalyst (e.g., Pd/C), a platinum-based catalyst, a rhenium-based catalyst, or a cobalt-based catalyst (e.g., CoMo)) in the presence of any carrier (e.g., a zeolite, an alumina, etc.); any useful reagent, such as hydrogen (e.g., $H_2$) or water (e.g., supercritical water); any useful pressure, e.g., such as from about 3 MPa to about 30 MPa (e.g., from about 5 MPa to about 20 MPa); and/or any useful temperature, e.g., such as from about 100° C. to about 500° C. (e.g., from about 250° C. to about 350° C.). Further exemplary hydrotreatment conditions are described in Ma F et al., "Biodiesel production: a review," *Bioresourc. Technol.* 1999; 70:1-15; Tran N H et al., "Catalytic upgrading of biorefinery oil from micro-algae," *Fuels* 2010; 89:265-74; and Wildschut J et al., "Catalyst studies on the hydrotreatment of fast pyrolysis oil," *Appl. Catalysis B* 2010; 99:298-306, each of which is incorporated herein by reference in its entirety.

Exemplary biofuels formed by hydrotreatment include naphtha, biodiesel (e.g., including one or more unsaturated fatty acids or fatty acid esters, such as of from about 10% to about 35% of a long chain fatty acid having a $C_{13}$-$C_{21}$ tail, such as a palmitic fatty acid ($C_{16}$ tail), linoleic fatty acid ($C_{18}$ tail), oleic fatty acid ($C_{18}$ tail), and/or stearic fatty acid ($C_{18}$ tail)), green diesel, renewable aviation fuel, hydrocarbons (e.g., light hydrocarbons), alcohol (e.g., ethanol; propanol, such as 1-propanol; butanol, such as n-butanol, isobutanol, 2-butanol, 3-butanol, 2-methyl-1-butanol, 3-methyl-1-butanol, etc.), and/or a biogas (e.g., hydrogen or methane). Other products formed by hydrotreatment include solid residuals (e.g., biochar and ash), aqueous co-products (e.g., ketoacids, amines, nutrients, etc.), as well as other useful co-products (e.g., animal feed, fertilizer, glycerine, biopolymers, etc.).

Phase Separation

Phase separation steps can be employed to separate components of a liquefied mixture, fermentation broth, aqueous fraction, a non-aqueous fraction, alcohol fraction, etc. Such steps include any that separate liquid from solid phases, as well as separate two or more phases that can be differentiated based on solubility, miscibility, etc. (e.g., as those present in non-aqueous phases, aqueous phases, lipophilic phases, etc.) in any useful solvent (e.g., an organic solvent, an aqueous solvent, water, buffer, etc.). Phase separation techniques include flash separation (e.g., separation of liquefied mixture into biocrude oil, solid residuals, aqueous phase, and/or aqueous co-products), acid absorption (e.g., absorption of acid in a matrix to provide recovered nutrients and water for recycled use), filtration, distillation, solvent extraction, ion liquid extraction, etc. The resultant products and co-products can include one or more intermediate products that can optionally be processed to form useful end-use products.

EXAMPLES

Example 1: Biochemical Upgrading of Dried Distillers' Grains

Dried distillers' grains are a high-protein biomass that is recalcitrant to further processing. The methods described herein provide a process to upgrade this biomass into useful intermediates and by-products. In one embodiment, the method includes an integrated sugar and protein fermentation process, with pre-treatment steps to facilitate fermentation. The method can include use of a dilute acid (e.g., use of 2-10% $H_2SO_4$ at a temperature of from about 90° C. to 145° C. for any useful incubation period, such as about 30 minutes to 6 hours) prior to use of a sugar fermentation strain (e.g., *E. coli* KO11) to convert sugars into ethanol. The method can also include use of an enzyme (e.g., about 0.5 g/L to 2 g/L of a protease or protease cocktail at a temperature of from about 37° C. to 55° C. for any useful incubation period, such as from about 12 to 48 hours) prior to use of a protein fermentation strain (e.g., *E. coli* YH83 with one or more additional mutated variations) to convert amino acids to alcohols (e.g., more than $C_2$ alcohols, such as $C_{3-10}$ alcohols) and amines (e.g., $NH_4$).

Figure 4A:
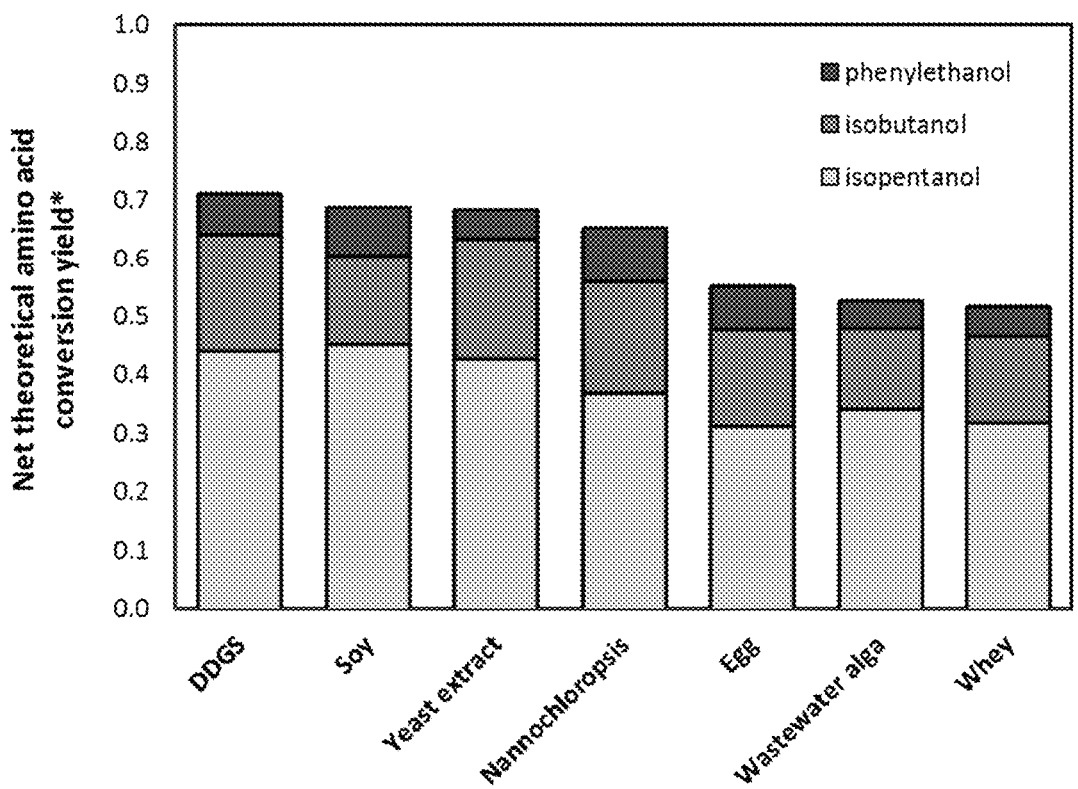
FIG. 4A-4C shows comparative technoeconomic potential of various high-protein feedstocks, including dried distillers' grains with solubles (DDGS). Provided are (A) a comparison of net theoretical amino acid yields for various biomass and (B) a comparison of unutilized high value amino acids for various biomass. The asterisk in (A) indicates that remineralized ammonia (as $NH_4MgPO_4$) was included in the mass balance. Also provided is (C) amino acid analysis of an exemplary biomass residuum.
Figure 4B:
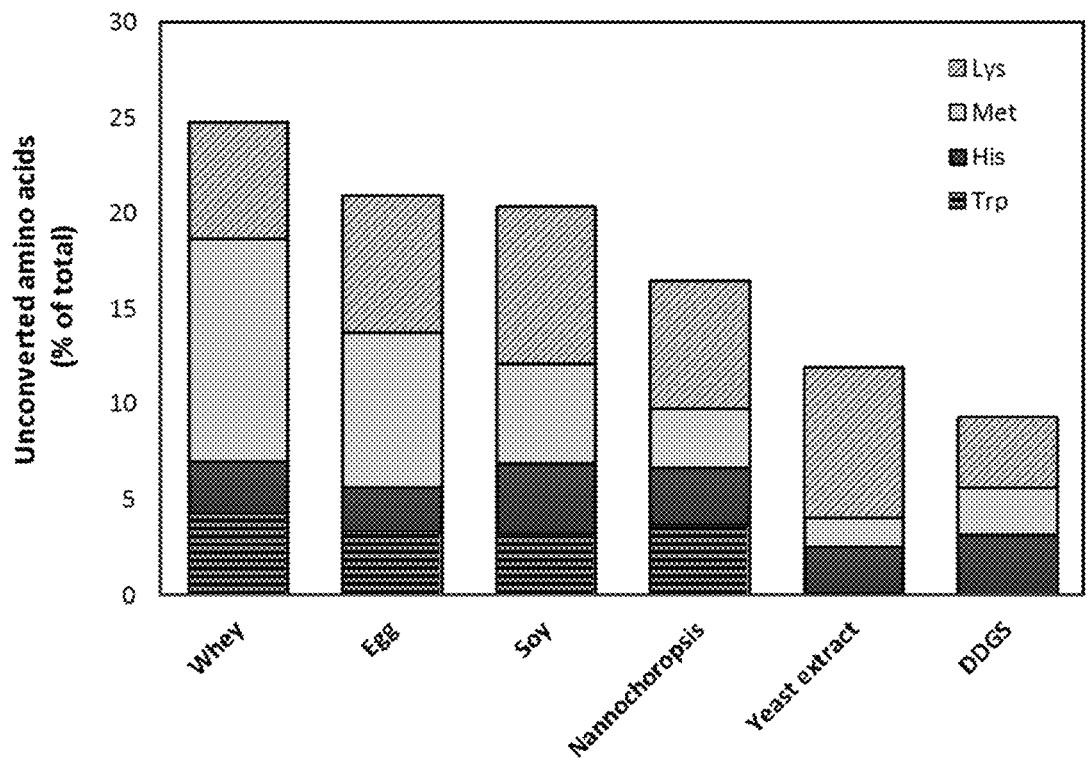

Any useful biomass can be processed. In particular, high-protein biomass can be particularly beneficial. Exemplary biomass include dried distillers' grains with solubles (DDGS), soy products (e.g., soy meal), yeast products (e.g., yeast extract), whey, algae (e.g., microalgae, macroalgae, diatoms, green algae, yellow algae, phytoplankton, plankton, protists, haptophytes, chlorophyta, and/or cyanobacteria), etc. FIG. 4A-4B provides the potential conversion yield of various biomass, as well as the potential yield of unutilized high value amino acids. As an initial step, processing methods in this Example were employed with DDGS samples.

Figure 5:
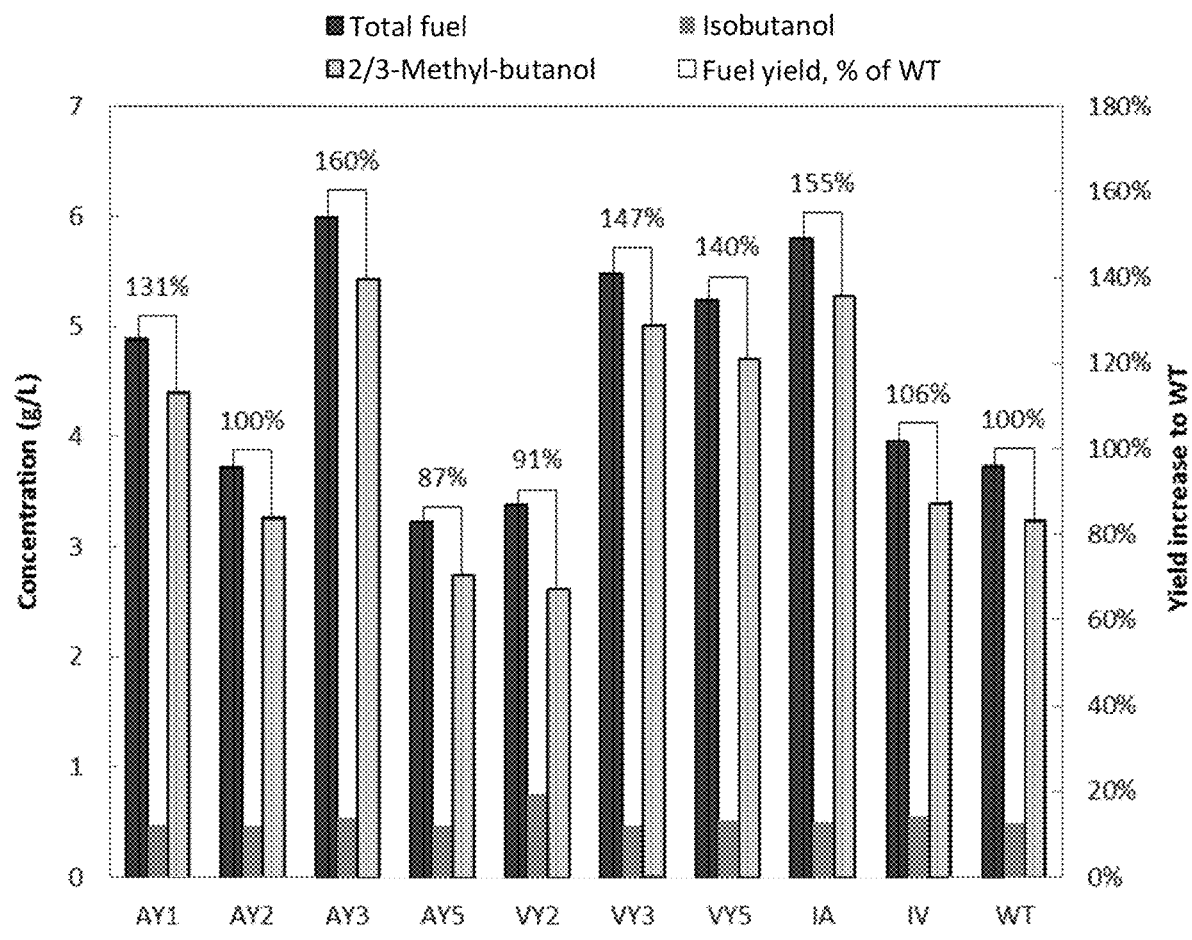
FIG. 5 shows the effect of redox cofactor engineering to produce various genetically engineered organism strains. Provided is a graph showing the concentration of fusel butanol produced by various redox mutant strains in the presence of an amino acid mixture. Redox mutant strains include AY1, AY2, AY3, AY5, VY2, VY3, VY5, IA, and IV, as described herein, which were compared to the wild-type (WT) strain.

Fermentation strains were developed and identified. As seen in FIG. 5, genetic engineering of E. coli resulted in organisms with high activity under anaerobic or microaerobic conditions. Our approach focused on, in part, altering the cofactor specificity of two enzymes in the pathway that provides isobutanol. In particular, two enzymes in the ketoacid pathway were modified: ketol-acid reductoisomerase IlvC and alcohol dehydrogenase YqhD. Generally, the wild-type strain employs a NADPH cofactor having a 2'-phosphate group. Modifications for the mutants were optimized to provide increased activity in the presence of a non-native NADH cofactor, as compared to the wild-type strain.

Mutant strains included AY1 (replacing IlvC with mutant A combined with replacing YqhD with mutant Y1), AY2 (replacing IlvC with mutant A combined with replacing YqhD with mutant Y2), AY3 (replacing IlvC with mutant A combined with replacing YqhD with mutant Y3), AY5 (replacing IlvC with mutant A combined with replacing YqhD with mutant Y5), VY2 (replacing IlvC with mutant V combined with replacing YqhD with mutant Y2), VY3 (replacing IlvC with mutant V combined with replacing YqhD with mutant Y3), VY5 (replacing IlvC with mutant V combined with replacing YqhD with mutant Y5), IA (replacing IlvC with mutant A), and IV (replacing IlvC with mutant V). Additional details for these mutant strains are described herein. In particular, five new E. coli strains showed increased conversion yield, as compared to the wild-type YH83 strain.

Figure 6:
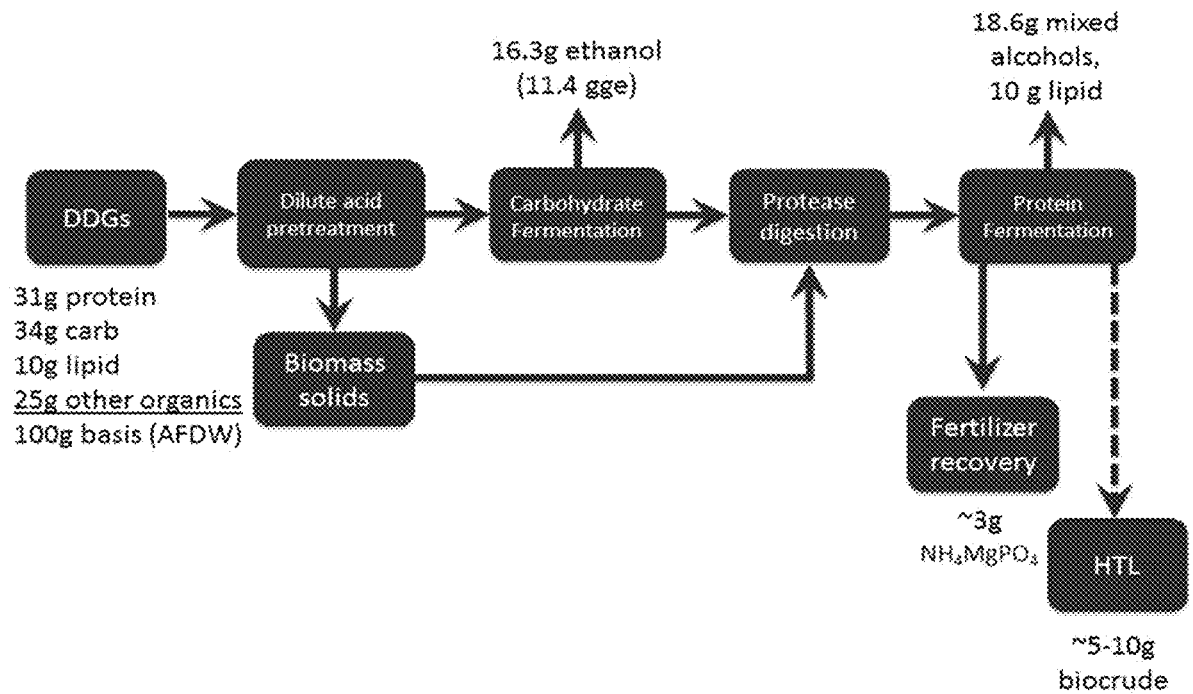
FIG. 6 shows an exemplary process flow diagram for upgrading biomass, such as DDGs.
Figure 7:
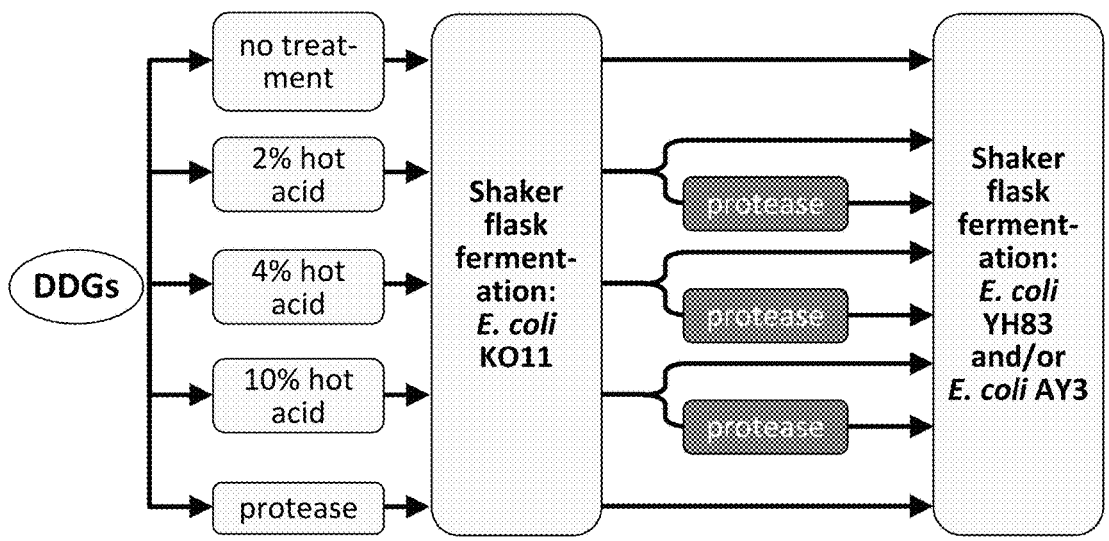
FIG. 7 shows another exemplary process flow diagram for further optimization.

FIG. 6 shows an exemplary process flow for use with modified fermentation stains. This exemplary process can be optimized by varying the dilute acid pre-treatment conditions, by employing enzymatic pre-treatment at particular points of the process, and by separating the two fermentation steps, in which each step uses a different strain (see, e.g., FIG. 7).

Dilute acid pre-treatment and fermentation achieved enhanced bioconversion of carbohydrates (e.g., sugars) into ethanol. As seen in FIG. 8, dilute acid hydrolysis pre-treatment resulted in more than 90% hydrolysis of various carbohydrates, including glucose, xylose, and arabinose. After treatment with 4% hot acid for 72 hours, the concentrations of these three representative sugars were decreased, and the concentration of ethanol increased at a theoretical conversion yield of about 60.7%. Improved xylose degradation can be promoted in any useful manner, e.g., by increasing the incubation temperature, increasing the concentration of the acid during pre-treatment, including a pre-treatment step with basic conditions (e.g., in the presence of NaOH or KOH), and/or by including one or more enzymes to cleave xylose, such as an isomerase, a reductase, etc.

Enzymatic pre-treatment and fermentation achieved enhanced bioconversion of proteins into fusel alcohol (e.g., more than $C_2$ alcohols, such as isobutanol, isopentanol, and/or phenylethanol) and amines. Enzymatic pre-treatment combined with dilute acid pre-treatment resulted in more than 90% hydrolysis of various carbohydrates. Furthermore, as seen in FIG. 9, after treatment for 72 hours, the concentration of amino acids was decreased, and the concentration of various fusel alcohols increased at a theoretical conversion yield of about 40.8%. Improved resistance to product inhibition can be promoted in any useful manner, e.g., by employing one or more separation or extraction steps; or by employing one or more lipids to promote vesicle formation.

Example 2: Cofactor Engineering to Improve the Fusel Alcohol Yield

Algal protein, as well as other high-protein feedstock, can be feasibly converted into fusel butanol with an engineered E. coli strain. In particular, algal protein has been used for producing fuel compounds, but the titer of fusel butanol is generally relatively low. One possible reason is cofactor imbalance during the algal protein fermentation.

To resolve this problem, a direct evolution approach was applied to switch the cofactor specificity of two enzymes (IlvC and YqhD) in the isobutanol pathway. These two enzymes rely on native cofactor NADPH in this pathway. Cofactor switching can allow for reactivity in the presence of a non-native cofactor (NADH), even if the native cofactor (NADPH) is lacking (e.g., such as in microaerobic or anaerobic conditions). Through high throughput screening, more than 20 YqhD mutants showed the activity with NADH.

Five YqhD mutants were selected and then combined with one of two IlvC mutants to reengineer the production strain. Upon combining the beneficial mutations of IlvC and YqhD, the engineered E. coli strain AY3 provided an optimized performance, in which fusel butanol yield increased by about 60%, as compared to wild-type E. coli, under anaerobic fermentation with an amino acid mixture. When applied to algal protein hydrolysates, the engineered AY3 strain produced from about 38% to 100% more fusel butanol in the fermentation broth, as compared to wild-type. This study provides a promising approach to improve bioconversion of algal protein into fusel butanol (e.g., as advanced fuel compounds) and amino acids (e.g., for further processing as nutrients or chemical intermediates). Additional details for this study are provided in Example 3. The following materials and methods were employed for this study.

Strains and Plasmids:

The mutant E. coli strain YH83 (BW25113/F' [traD36, proAB+, lacI$^q$ ZΔM15]ΔglnAΔgdhAΔluxSΔlsrA) containing plasmids pYX68, pYX90, and pYX97 was generously provided by Professor James C Liao from University of California, Los Angeles (UCLA) (see, e.g., Huo Y X et al., Nat. Biotechnol. 2011; 29(4):346-51). The strain was engineered for bioconversion of protein hydrolysates into isobutanol. Plasmids pYX90 and pYX97 contained IlvC and YqhD, which use NADPH as the cofactor. Plasmid pBbE1a and the E. coli strain DH1 were used for the expression and screening of mutant libraries of enzyme YqhD, as well as for the creation of IlvC mutants.

Selection of Cofactor Binding Sites:

The amino acids for mutation in YqhD were selected by inspecting the cofactor NADPH binding site. Autodock 4 was used to investigate the cofactor-enzyme interaction. The protein X-ray structure of E. coli K-12 YqhD (Entry No. 1OJ7) containing cofactor NADPH was extracted from RCSB Protein Data Bank.

Mutant Library Construction, Expression, and High-Throughput Screening:

Plasmid pBbE1a was generously provided by Dr. Taek Soon Lee from Joint BioEnergy Institute. Genes IlvC and YqhD were amplified from plasmids (pYX90 and pYX97), and then sub-cloned into vector pBbE1a under restriction cutting sites (EcoRI and BamHI) to achieve vectors pBbE1a-IlvC and pBbE1a-YqhD, respectively. Saturation mutagenesis was applied to create a recombinant mutant library of enzyme YqhD, following the description in the previous study (see, e.g., Wu W et al., "Site-saturation mutagenesis of formate dehydrogenase from *Candida bodinii* creating effective NADP+-dependent FDH enzymes," *J. Molec. Catal. B* 2009; 61(3-4):157-61). For the recombinant library of YqhD, primers with degenerate codons were used to create mutations at the selected amino acid sites. High fidelity DNA polymerase fusion Q5 (New England BioLabs, Inc. (NEB), Ipswich, Mass.) was used to generate the library and to express library members in *E. coli* DH1. Strains containing YqhD mutants were diluted properly and spread onto Luria-Bertani (LB) plates supplemented with ampicillin (100 μg/mL) for the following library screening.

According to the previous study (see, e.g., Bastian S et al., *Metab. Eng.* 2011; 13(3):345-52), the two mutant IlvCs (A71S, R76D, S78D Q110V/Q110A) switched the cofactor specificity from NADPH to NADH with the relatively high activity with NADH. Site mutagenesis (point mutation) was used to create two mutants of enzyme IlvC at the four target amino sites mentioned above. An iterative strategy was used to create all four sites of mutations. High fidelity DNA polymerase fusion Q5 was again used to create point mutations of IlvC in the vector pBbE1a-IlvC, as described before (see, e.g., Wu W et al., *J. Molec. Catal. B* 2009; 61(3-4): 157-61). Mutations were confirmed through DNA sequencing. All the primers used herein are listed in Table 1, below.

TABLE 1

Primers and mutants for YqhD and IlvC

| Name | Sequence | SEQ ID NO: | Notes |
|---|---|---|---|
| YqhD-pBbE1a-F | 5-CTC AGC GAA TTC ATG AAC AAC TTT AAT CTG CAC ACC CCA AC-3 | 10 | Clone YqhD into pBbE1a |
| YqhD-pBbE1a-R | 5-TGACCTGGATCCTTA GCG GGC GGC TTC GTA TAT AC-3 | 11 | |
| IlvC-pBbE1a-F | 5-CTC AGC GAA TTC ATG GCT AAC TAC TTC AAT ACA CTG AAT CTG C-3 | 12 | Clone IlvC into pBbE1a |
| IlvC-pBbE1a-R | 5-TGACCTGGATCC TTA ACC CGC AAC AGC AAT ACG TTT C-3 | 13 | |
| YqhD-S40-F | 5-GTATTGATTACCTACGGCGGC GGC NNN GTG AAA AAA ACC GGC GTT CTC-3 | 14 | Create mutant library S40 |
| YqhdS40-R | 5-GAG AAC GCC GGT TTT TTT CAC NNN GCC GCC GCC GTA GGT AAT CAA TAC-3 | 15 | |
| YqhD-G39S40-F | 5-GTATTGATTACCTACGGCGGC NNN NNN GTG AAA AAA ACC GGC GTT CTC-3 | 16 | Create mutant library G39S40 |
| Yqhd-G39S40-R | 5-GAG AAC GCC GGT TTT TTT CAC NNN NNN GCC GCC GTA GGT AAT CAA TAC-3 | 17 | |
| YqhD-S40P-F | 5-GTATTGATTACCTACGGCGGC CCG GTG AAA AAA ACC GGC GTT CTC-3 | 18 | Mutant Y1 (S40P) |
| Yqhd-S40P-R | 5-GAG AAC GCC GGT TTT TTT CAC CGG GCC GCC GTA GGT AAT CAA TAC-3 | 19 | |
| YqhD-S40R-F | 5-GTATTGATTACCTACGGCGGC CGT GTG AAA AAA ACC GGC GTT CTC-3 | 20 | Mutant Y2 (S40R) |
| Yqhd-S40R-R | 5-GAG AAC GCC GGT TTT TTT CAC CGT GCC GCC GTA GGT AAT CAA TAC-3 | 21 | |
| YqhD-G39I/S40R-F | 5-GTATTGATTACCTACGGCGGC ATCCGT GTG AAA AAA ACC GGC GTT CTC-3 | 22 | Mutant Y3 (G39I/S40R) |
| YqhD-G39I/S40R-R | 5-GAG AAC GCC GGT TTT TTT CAC ACG GAT GCC GCC GTA GGT AAT CAA TAC-3 | 23 | |
| YqhD-G39Y/S40H-F | 5-GTATTGATTACCTACGGCGGC TATCAT GTG AAA AAA ACC GGC GTT CTC-3 | 24 | Mutant Y5 (G39Y/S40H) |
| Yqhd-G39Y/S40H-R | 5-GAG AAC GCC GGT TTT TTT CAC ATG ATA GCC GCC GTA GGT AAT CAA TAC-3 | 25 | |
| IlvCA71SR76DS78D-F | 5-CGT AAA GAA TCG ATT GCC GAG AAG GAT GCG GAT TGG-3 | 26 | |
| IlvCA71SR76DS78D-R | 5-CCA ATC CGC ATC CTT CTC GGC AAT CGA TTC TTT ACG-3 | 27 | |
| ilvCQ110A-F | 5-CGG ACA AGG CGC ACT CTG ATG TAG-3 | 28 | Mutant A (A71S/R76/S78D/Q110) |
| ilvCQ110A-R | 5-CTA CAT CAG AGT GCG CCT TGT CCG-3 | 29 | |
| ilvCQ110V-F | 5-CGG ACA AGG TGC ACT CTG ATG TAG-3 | 30 | Mutant V (A71S/R76D/S78D/Q110) |
| ilvCQ110V-R | 5-CTA CAT CAG AGT GCA CCT TGT CCG-3 | 31 | |

TABLE 1-continued

Primers and mutants for YqhD and IlvC

| Name | Sequence | SEQ ID NO: | Notes |
|---|---|---|---|
| ILVC-Pyx90-Gib-F1 | 5-GAA AGC TCT CTA GGT CGA CGA GGA ATC ACC ATG GCT AAC TAC TTC AAT ACA CTG AAT CTG-3 | 32 | Replace IlvC with mutant |
| ILVC-Pyx90-Gib-R1 | 5-GTA CTT AGG CAT GGT ATA TCT CCT TCC GGG TTA ACC CGC AAC AGC AAT ACG TTT CAT ATC-3 | 33 | A or V |
| ILVD-AvTA-pYX90-Gib-F2 | 5-GAT ATG AAA CGT ATT GCT GTT GCG GGT TAA CCC GGA AGG AGA TAT ACC ATG CCT AAG TAC-3 | 34 | |
| ILVD-AvTA-pYX90-Gib-R2 | 5-GGA TTT GTC CTC CTA CTC AGG AGA GCG TTC ACC GAC AAA CAA CAG ATA AAA CGA AAG GCC CAG-3 | 35 | |
| Spec-alsS-pYX90-Gib-F3 | 5-CTG GCT CTT TCG TTT TAT CTG TTG TTT GTC GGT GAA CGC TCT CCT GAG TAG GAC AAA TCC-3 | 36 | |
| Spec-alsS-pYX90-Gib-R3 | 5-CAG ATT CAG TGT ATT GAA GTA GTT AGC CAT GGT GAT TCC TCG TCG ACC TAG AGA GCT TTC-3 | 37 | |
| YqhD-Pyx97-Gib-F1 | 5-GGA GAA AGG TCA CAT GAA CAA CTT TAA TCT GCA CAC CCC AAC CCG CAT TC-3 | 38 | Replace YqhD with mutant |
| YqhD-Pyx97-Gib-R1 | 5-CTC TAG CAC GCG TAC CAT GGG ATC CTT AGC GGG CGG CTT CGT ATA TAC-3 | 39 | Y1, Y2, Y3, or Y5 |
| ColE-Amp-pYX97-Gib-F2 | 5-GTA TAT ACG AAG CCG CCC GCT AAG GAT CCC ATG GTA CGC GTG CTA GAG-3 | 40 | |
| ColE-Amp-pYX97-Gib-R2 | 5-CAT GAT AAT AAT GGT TTC TTA GAC GTC AGG TGG CAC TTT TCG GGG AAA TGT GCG CGG AAC-3 | 41 | |
| LeuDH-KivD-pYX97-F3 | 5-GTT CCG CGC ACA TTT CCC CGA AAA GTG CCA CCT GAC GTC TAA GAA ACC ATT ATT ATC ATG-3 | 42 | |
| LeuDH-KivD-pYX97-R3 | 5-GAA TGC GGG TTG GGG TGT GCA GAT TAA AGT TGT TCA TGT GAC CTT TCT CC-3 | 43 | |

Single colonies of YqhD mutant and wild-type were cultured into 96-well plates. Each well contained 200 µl of LB medium with corresponding antibiotics. Cultures were incubated at 300 rpm and at 37° C. overnight (16 hours) and induced by 1.0 mM isopropyl β-d-1-thiogalactopyranoside (IPTG) for another 24 hours at 250 rpm, 30° C. in a humidified shaker. Cells were harvested by centrifugation (3000 rpm, 4° C., 15 min.) and stored at −20° C. before conducting assays. For high-throughput screening assays, E. coli cells were lysed with 200 µl of 50 mM MOPS (pH 7.0) containing 1 mg/ml of lysozyme (Sigma-Aldrich Corp., St. Louis, Mo.) and 20 U/ml of DNase (NEB) at 4° C. for 6 hours under gentle shaking. Lysed cells were spun down, and 100 µl of the cell free extract was transferred into another 96 well plate. YqhD and its mutant activity assay buffer contained 50 µl of 0.25 mM NADH, 10 µl of isobutyraldehyde, and 40 µl of MOPS (pH 7.0). Consumption of NADH was monitored at 340 nm in a plate reader (Molecular Devices, LLC, Sunnyvale, Calif.).

Plasmids and Strain Construction for Anaerobic Bioconversion of Algal Protein Hydrolysates:

Positive hits with high activity with NADH were selected to replace the wild-type YqhD gene in plasmid pYX97. Two mutant genes of IlvC were selected to replace the wild-type IlvC gene in plasmid pYX90. A Gibson assembly was applied to replace wild-type YqhD and IlvC with the corresponding mutant genes. Plasmids pYX97 and pYX90 with mutant genes, as well as pYX68 were co-transformed into strain YH40 for the bioconversion of algal protein hydrolysates into fusel butanol. All the primers used herein are listed in Table 1, above.

Addition of NADPH into Fermentation Media:

Wild-type strain YH83 was cultured in 20 ml of LB media with 100 µg/ml ampicillin, 34 µg/ml chloramphenicol, and 25 µg/ml spectinomycin overnight. Then, 5 ml of culture was transferred into 150 ml of 1×M9 medium (see, e.g., Huo Y X et al., *Nat. Biotechnol.* 2011; 29(4):346-51; and Wu W, "Fuel ethanol production using novel carbon sources and fermentation medium optimization with response surface methodology," *Int. J. Agri. Biol. Eng.* 2013; 6(2):42-53) (in 160 ml serum bottle) containing 20 g/L of an amino acid mixture, 2 g/L of LB, and 150 µM NADPH with corresponding aforementioned antibiotics in a rotary shaker at 220 rpm, 37° C. The culture was induced by 1 mM IPTG at 37° C. when the OD reached 0.6 for the production of fusel butanol. Samples were tested at regular time intervals to determine the concentration of fusel butanol in each sample. Each run was performed in biological duplicate.

Investigation of the Fusel Butanol Yields with an Amino Acid Mixture:

Engineered strains of YH83 containing various combinations of mutant YqhD and IlvC were cultured in 20 ml of LB media with corresponding aforementioned antibiotics, overnight. Then, 3 ml of culture was transferred into 30 ml of 1×M9 medium containing 20 g/L of an amino acid mixture (Sigma-Aldrich, Corp.), 5 g/L of LB, and antibiotics. Fermentation was performed as described above. Each run was performed in biological duplicate. Strains containing the details of the mutants are listed in Table 1, above.

Bioconversion of Algal Protein Hydrolysates into Fusel Butanol:

ATP algae biomass samples were pretreated with diluted acid, according to the protocol from the National Renewable Energy Laboratories (referenced hereinafter as "ATP3") or according to the protocol described previously (see, e.g., Garcia-Moscoso J L et al., "Kinetics of peptides and arginine production from microalgae (*Scenedesmus* sp.) by flash hydrolysis," *Ind. Eng. Chem. Res.* 2015; 54(7):2048-58) through a thermal flash hydrolysis (referenced hereinafter as "ODU"). Hydrolyzed algal carbohydrate was converted into ethanol through alcoholic fermentation using an ethanogenic strain, *E. coli* KO11. The cell mass was removed through centrifugation (6,000 rpm, 4° C., 10 min.) at the end of KO11 fermentation. The supernatant containing ethanol and algal protein was air-bubbled at room temperature for 10 minutes to remove ethanol. Then, the resultant supernatant was concentrated and digested with 2 mg/mL Pronase® (Promega Corp., Madison, Wis.) following the manufacturer's protocol. The protease-digested, algal protein hydrolysate was sterilized through a 0.45 µm PTFE membrane and used as the fermentation media for fusel butanol production. This hydrolysate was incubated with mutant strain AY3 in the presence of the amino acid mixture. Samples were tested at regular intervals with GC-MS analysis. Each run was performed in biological duplicate.

Analytic Determination of the Presence of Fusel Butanol and Amino Acid:

Concentrations of amino acids were analyzed using an amino acid analyzer (Hitachi Ltd., Tokyo, Japan) at the genome center of University of California, Davis, following their protocol. Fusel butanol was extracted using ethyl acetate at a ratio of 1:1 (ethyl acetate:fermentation broth), with 2-methyl-pentanol as an internal reference. The mixture was vortex at 1,200 rpm for 20 min. and centrifuged at 14,000 rpm, 5 min. The ethyl acetate layer was collected for further GC-MS analysis. Two µl of sample was inserted into the injection port (220° C.) of an Agilent 7890A Gas Chromatograph containing a 30 m×0.25 mm i.d. DB wax capillary column with a film thickness of 0.25 µm. The column was temperature programmed as follows: 40° C. for 4 min., increasing to 65° C. at 10° C./min. and holding for 10 min., then increasing to 120° C. at 10° C./min. and holding for 2 min., and then increasing to 220° C. at 20° C./min and holding for 5 min. The carrier gas was ultra-high purity helium at a constant flow rate of 1.8 ml/min. The initial column head pressure was 16.188 psi with a split ratio of 10. The gas chromatograph was coupled to a quadrupole mass selective detector (MSD), Agilent 5975C. The MSD parameters included EI at 70 eV, mass range at 10-650 Da, and scan speed at 2 scans/sec. Spectral components were searched against the NIST 2015 mass spectral library. Serial of dilutions of isobutanol and 2-methyl-butanol in ethyl acetate were analyzed to determine a standard curve. Concentrations of fusel butanol were calculated by referring samples to the standard curve.

Example 3: Cofactor Engineering of Ketol-Acid Reductoisomerase (IlvC) and Alcohol Dehydrogenase (YqhD)

Increasing concerns about diminishing fossil fuels and global environmental problems have attracted interest in sustainable biofuels obtained from renewable resources (see, e.g., Peralta-Yahya P P et al., "Microbial engineering for the production of advanced biofuels," *Nature* 2012; 488(7411): 320-8; and Keasling D, "Sustainable production of advanced biofuels," 241*st ACS National Meeting & Exposition*, held on 27-31 Mar. 2011 in Anaheim, Calif., Abstract 202). Algae-based biofuel is considered to be one sustainable alternative biofuel due to several benefits, including simplified pretreatment as compared to lignocellulosic biomass, higher biomass yields as compared to plants, possible cultivation on nonarable land, and possible reclamation of waste water (see, e.g., Razeghifard R, "Algal biofuels," *Photosynth. Res.* 2013; 117(1-3):207-19; and Luque R, "Algal biofuels: the eternal promise?," *Energy Environ. Sci.* 2010; 3:254-7). So far, algae biomass have been converted to versatile biofuel chemicals, such as bioethanol, biohydrogen, biogas, crude oil, and biodiesel (see, e.g., Li K et al., "An overview of algae bioethanol production," *Int. J. Energy Res.* 2014; 38(8):965-77; Melis A et al., "Hydrogen production: green algae as a source of energy," *Plant Physiol.* 2001; 127(3):740-8; Hernindez D et al., "Biofuels from microalgae: lipid extraction and methane production from the residual biomass in a biorefinery approach," *Bioresour. Technol.* 2014; 170:370-8; López Barreiro D et al., "Assessing microalgae biorefinery routes for the production of biofuels via hydrothermal liquefaction," *Bioresour. Technol.* 2014; 174:256-65; Sharma K K et al., "High lipid induction in microalgae for biodiesel production," *Energies* 2012; 5(5):1532-53; and Scott S A et al., "Biodiesel from algae: challenges and prospects," *Curr. Opin. Biotechnol.* 2010; 21(3):277-86).

Current state-of-the-art algal biofuels have primarily focused on producing biodiesel by boosting algal lipid yield under nutrient stress conditions. This strategy ignores another major component of algae: proteins. Under conditions that support robust algae growth, algal carbohydrate and proteins are two of the major components of biomass, including up to ~80% of the ash-free dry weight (AFDW) of microalgae biomass, in which up to 60% can be proteins (see, e.g., Luque R, *Energy Environ. Sci.* 2010; 3:254-7; Becker E W, "Microalgae: biotechnology and microbiology," Cambridge University Press, Cambridge, U.K., 1994 (293 pp.); and Singh J et al., "Commercialization potential of microalgae for biofuels production," *Renew. Sustain. Energy Rev.* 2010; 14(9):2596-610).

Recently, engineered *E. coli* strains have been employed to convert algal protein into fusel butanol. Modified strains can be selected to exhibit deamination of protein hydrolysates to C4 and C5 alcohols at 56% of the theoretical yield (see, e.g., Huo Y X et al., "Conversion of proteins into biofuels by engineering nitrogen flux," *Nat. Biotechnol.* 2011; 29(4):346-51). By combining the Ehrlich pathway with three exogenous transamination and deamination cycles, the engineered *E. coli* strain produced up to 0.183 g of fusel butanol/g of amino acids under aerobic or microaerobic fermentation conditions (see, e.g., Huo Y X et al., *Nat. Biotechnol.* 2011; 29(4):346-51). In some instances, anaerobic conditions can be preferred for large scale fermentation due to lower operating costs and higher theoretical yield.

In the Ehrlich pathway for isobutanol production, two enzymes use nicotinamide adenine dinucleotide phosphate (NADPH) as a cofactor: ketol-acid reductoisomerase (IlvC) and alcohol dehydrogenase (YqhD). Thus, bioconversion of protein hydrolysates requires at least two reducing equivalents of NADPH to convert glucose to isobutanol (see, e.g., Atsumi S et al., "Non-fermentative pathways for synthesis of branched-chain higher alcohols as biofuels," *Nature* 2008; 451(7174):86-9). Under anaerobic fermentation, glycolysis can only produce nicotinamide adenine dinucleotide (NADH) as an available reducing equivalent, while the pentose phosphate pathway (PPP) and the tricarboxylic acid (TCA) cycle are not functional due to the lack of oxygen. This may result in a cofactor imbalance during anaerobic fermentation or oxygen limited fermentation conditions (e.g., microaerobic conditions). Thus, although anaerobic or microaerobic fermentation is preferred to minimize processing costs and to increase theoretical yields, these very fermentation conditions can result in an inhibitory cofactor imbalance that can limit alcohol production.

NADPH limitation can result in cofactor imbalance, as reported previously for isobutanol production from glucose (see, e.g., Shi A et al., "Activating transhydrogenase and NAD kinase in combination for improving isobutanol production," *Metab. Eng.* 2013; 16:1-10; and Bastian S et al., "Engineered ketol-acid reductoisomerase and alcohol dehydrogenase enable anaerobic 2-methylpropan-1-ol production at theoretical yield in *Escherichia coli*," *Metab. Eng.*

2011; 13(3):345-52). Therefore, we hypothesized that fusel butanol yield can be improved through resolving the cofactor imbalance present in anaerobic fermentation of algal protein.

To achieve this, we first tested our hypothesis that lack of NADPH affects fusel alcohol production. Thus, we performed experiments by adding NADPH in the fermentation media, and observing the effect of NADPH on alcohol yield. Then, we designed two isobutanol biosynthesis pathway enzymes (IlvC and YqhD) to switch cofactor specificity from NADPH to NADH through directed evolution. Upon combining the beneficial mutations of two enzymes in the isobutanol biosynthesis pathway, the resultant engineered *E. coli* strain improved fusel butanol yield by about 60%, as compared to wild-type, under anaerobic fermentation conditions with an amino acid mixture as the feedstock. When applied to algal protein hydrolysates, the mutant strain with best performance produced 38% to 100% more fusel butanol, as compared to wild-type.

Figure 10A:
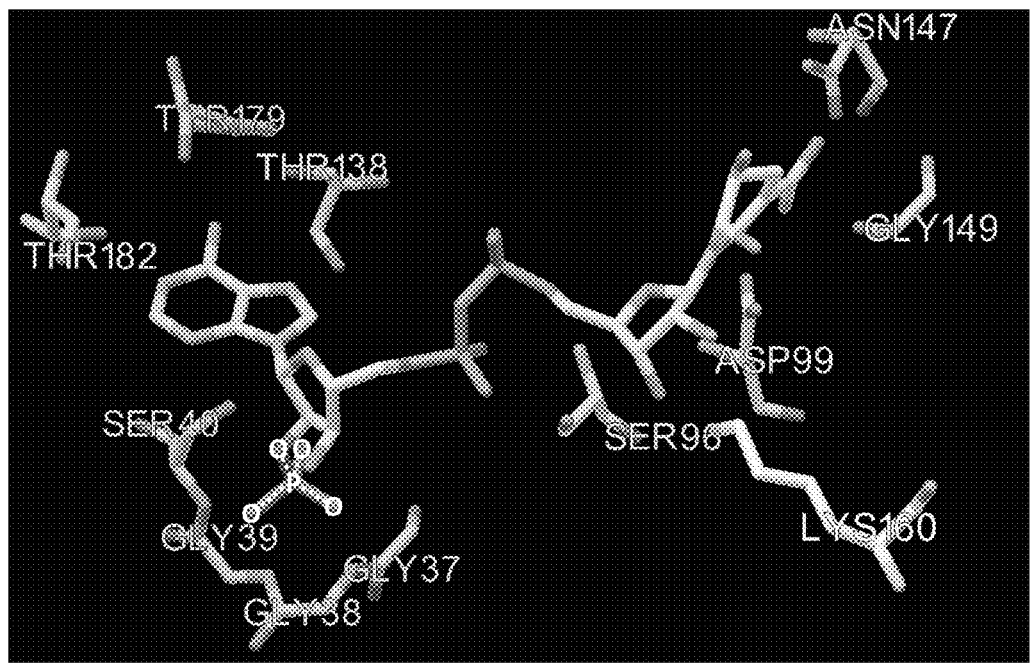

Engineering the Cofactor Specificity of *E. coli* IlvC and YqhD to Switch to NADH:

The x-ray crystal structure of YqhD had been reported previously (see, e.g., Sulzenbacher G et al., "Crystal structure of *E. coli* alcohol dehydrogenase YqhD: evidence of a covalently modified NADP coenzyme," *J. Mol. Biol.* 2004; 342(2):489-502). This structure contained cofactor NADP$^+$ as a ligand. The protein possesses a GGGS (residues 37-40) motif, which binds the 2'-phosphate groups of NADP through hydrogen bonds, as shown in FIG. 10A (phosphorous and oxygen atoms of the 2'-phosphate is indicated by P, O, and dashed lines). These hydrogen bonds provide a preference for binding NADPH over NADH, making the motif GGGS a major cofactor binding site. Therefore, two amino acids (Gly39Ser40) were chosen to identify mutations that would confer cofactor switching from NADPH to NADH through site-saturation mutagenesis.

Figure 10B:
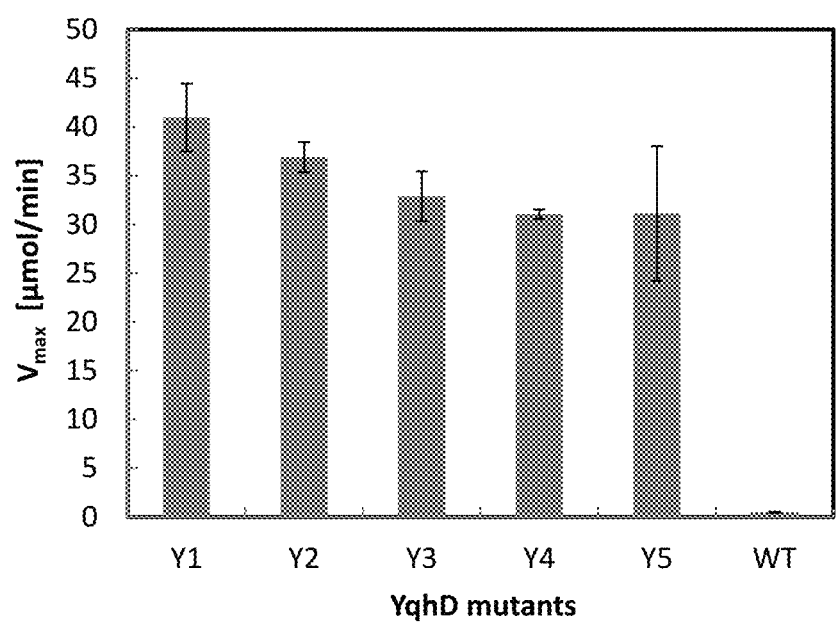

Two mutant libraries (G39S40 and S40) were generated and screened for NADH activity using a cell free extract. More than 20 positive mutants showed various activities with cofactor NADH. Five mutants showed 60-80 times higher activity with NADH (as shown in FIG. 10B), as compared to wild-type YqhD (FIG. 10C). The five mutants were selected to replace wild-type YqhD in plasmid pYX97, including two single mutations of S40 (Y1, Y2) (see, e.g., FIGS. 10D-10E) and three double mutations of G39S40 (Y3, Y4, Y5) (see, e.g., FIG. 10F).

*E. coli* IlvC has been engineered to switch cofactor from NADPH to NADH for isobutanol production under anaerobic fermentation (see, e.g., Bastian S et al., *Metab. Eng.* 2011; 13(3):345-52). Two mutants of IlvC (A71S, R76D, S78D, Q110V/A) with higher activity with NADH were chosen to replace wild-type IlvC in plasmid pYX90 (see, FIG. 11A-11B).

Figure 12A:
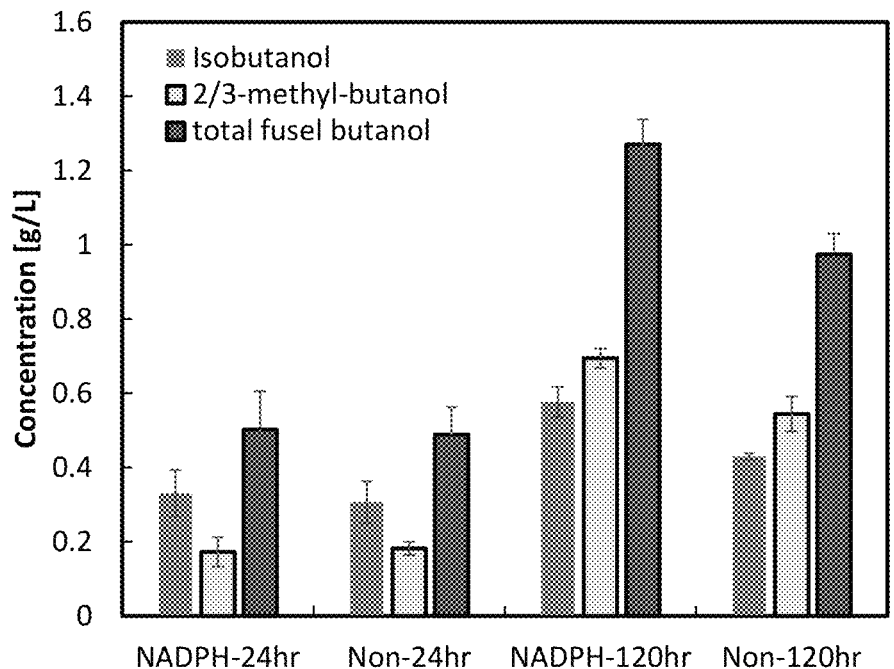
FIG. 12A-12B shows the effect of adding native cofactor NADPH on yield of butanol for protein bioconversion. Provided are (A) a graph showing the effects of NADPH addition on the produced concentration fusel butanol under anaerobic fermentation conditions and (B) a graph showing the improvement of fusel butanol yield after 24 hours and 120 hours.
Figure 12B:
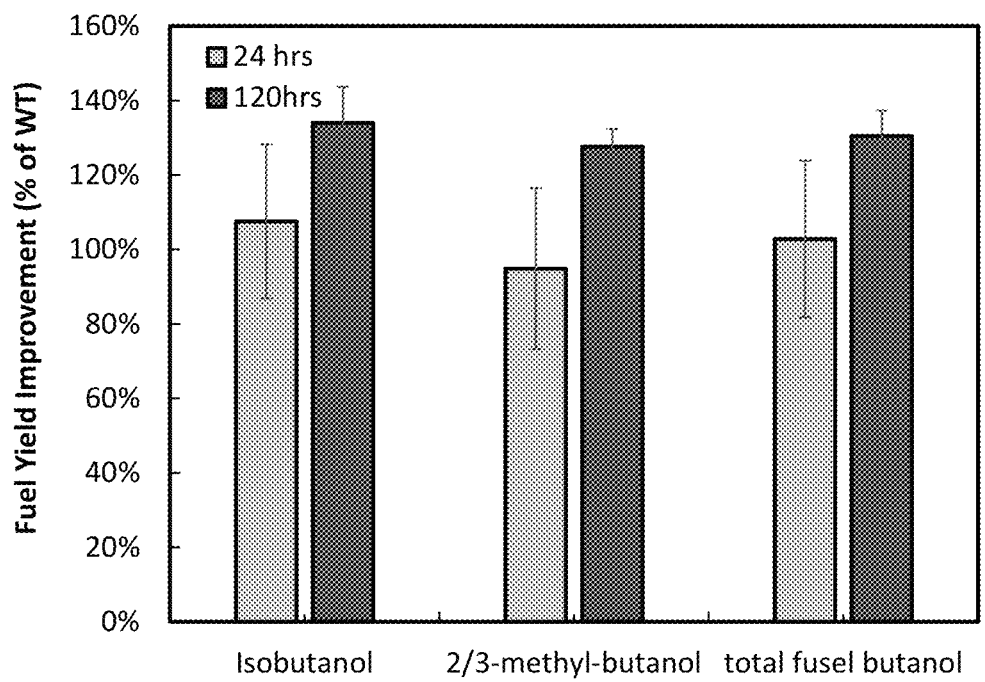

Improved Fusel Butanol Yield Under an Aerobic Fermentation with NADPH:

We hypothesized that cofactor imbalance compromised fusel butanol yield during protein bioconversion. To test this hypothesis, the native cofactor NADPH of YqhD and IlvC was added into the fermentation medium as an external source of NADPH. FIG. 12A-12B show that addition of NADPH significantly improved yields of isobutanol and 2/3-methyl-butanol during protein bioconversion. Within 5 days of cultivation, yields of isobutanol, 2/3-methyl-butanol, and total fusel butanol increased by about 34%, 28%, and 30%, respectively, confirming that cofactor imbalance can be one factor affecting fusel butanol production.

Figure 13A:
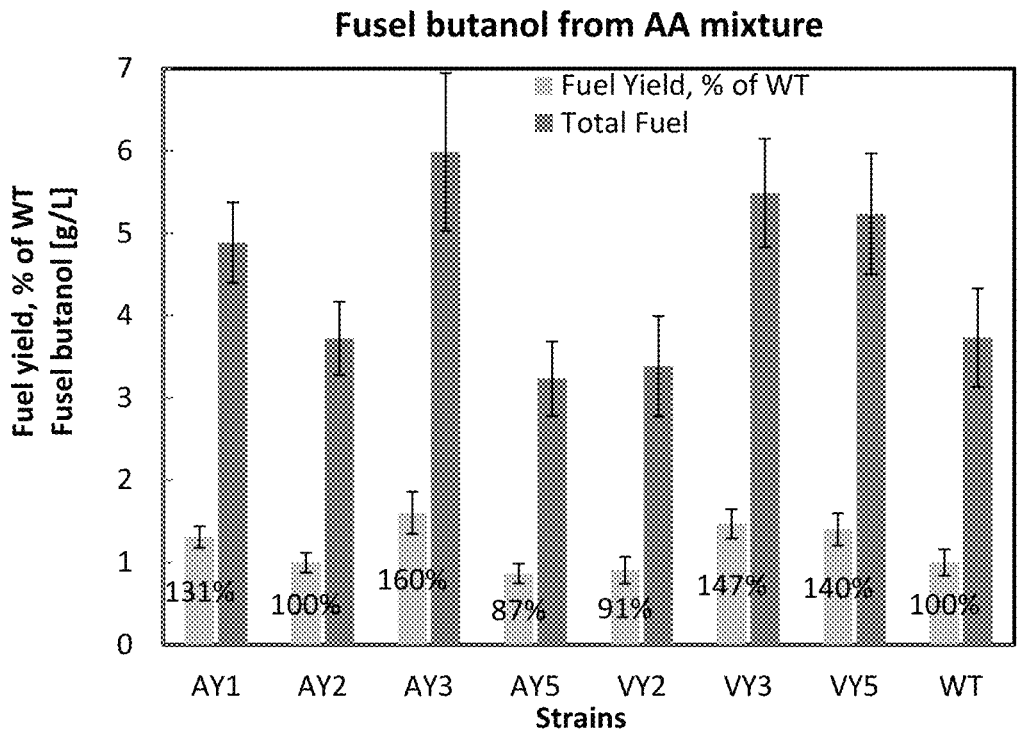
FIG. 13A-13C shows bioconversion of algal protein hydrolysates into fusel butanol by engineered mutant strains. Provided are (A) a graph showing fermentation performance of engineered mutant strains on an amino acid mixture; (B) a graph showing bioconversion of two algal protein hydrolysates (ATP3 or ODU) into fusel butanol employing either an engineered mutant strain AY3 or a wild-type strain YH83 ("WT"); and (C) a graph showing consumption of two algal protein hydrolysates (ATP3 or ODU) by engineered mutant strain AY3 after 72 hours.

Bioconversion of Amino Acid Mixtures and Algal Protein into Fusel Butanol:

The fusel butanol yields of the engineered YH83 strains, which contained both IlvC and YqhD mutants, were initially investigated through bioconversion of amino acid mixtures in the 1×M9 medium. As seen in FIG. 13A, the mutant strains produced various amounts of fusel butanol in the fermentation broth. Among the seven mutant strains, four strains (AY1, AY3, VY3, and VY5) yielded at least 30% higher concentrations of fusel butanol, as compared to wild-type. In particular, the AY3 strain produced more than 60% higher amount of fusel butanol than wild-type, i.e., up to 6 g/L fusel butanol from 20 g/L amino acids. The wild-type produced 3.7 g/L fusel butanol.

Further studies were conducted with pretreated algal protein hydrolysates. Two hydrolysates were used as medium to investigate fermentation performance of mutant strain AY3. As shown in the FIG. 13B, mutant strain AY3 produced higher titers of isobutanol, 2/3-methyl-butanol, and total fusel butanol with both pretreated algal protein hydrolysates (ATP3 and ODU), as compared to wild-type strain YH83.

Figure 13B:
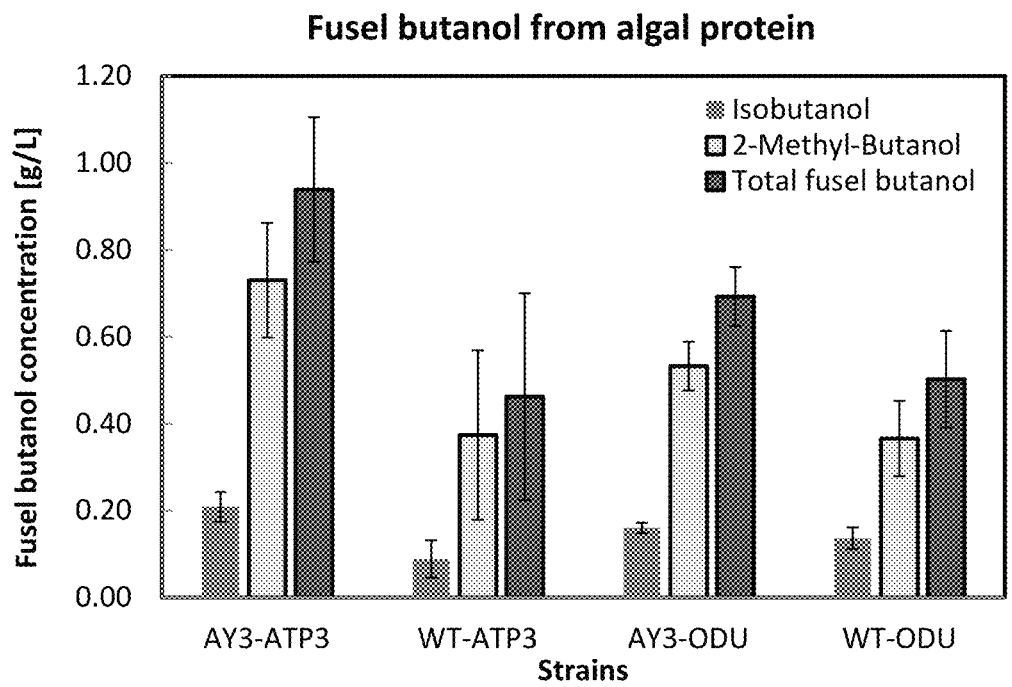

Within 3 days of fermentation, the mutant strain AY3 yielded more than 100% and 38% higher total fusel butanol titers than wild-type with ATP3 and ODU, respectively, as shown in FIG. 13B. Yields using algal hydrolysates were lower than that observed with amino acid mixtures. Yields can be optimized, e.g., by providing supplemental nutrients with the algal hydrolysates, adjusting the ionic strength of the hydrolysate, neutralizing the hydrolysate, etc.

Figure 13C:
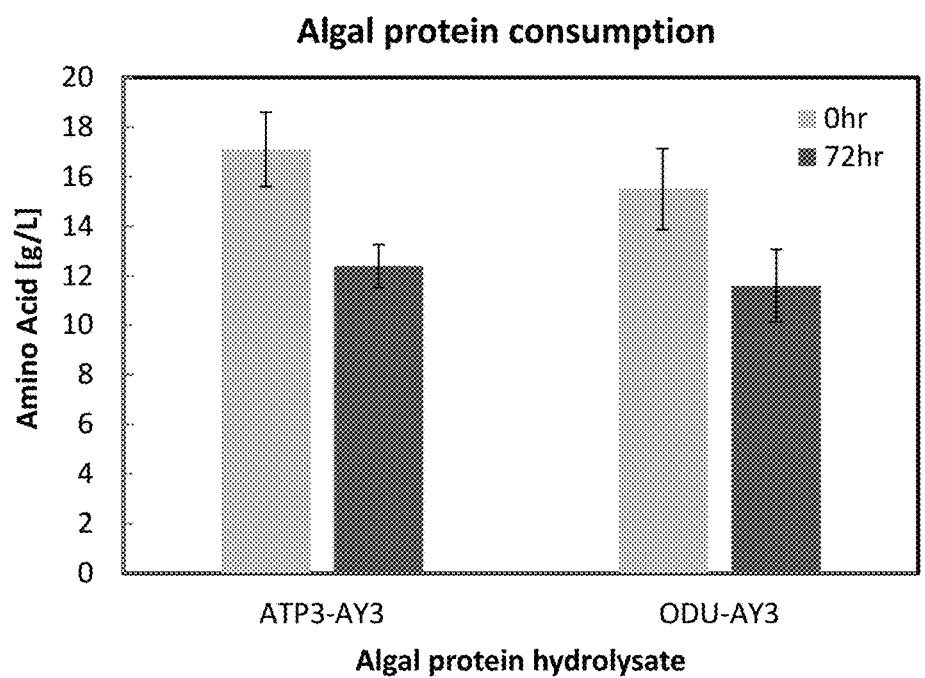

As shown in FIG. 13C, only about 25% of algal protein hydrolysates were consumed after 3 days of fermentation. Based on substrate consumption, the strain AY3 yielded 0.2 to 0.18 g fusel butanol/g amino acid for converting algal hydrolysates AY3 and ODU, respectively. Yields could be optimized in any useful manner, e.g., by increasing incubation times, increasing protease digestion times, repeating and recycling separated fractions, etc.

Here, we engineered two enzymes (IlvC and YqhD) in the isobutanol biosynthesis pathway to resolve cofactor imbalance during fermentation. By combining beneficial mutations of these two enzymes, the engineered AY3 strain improved fusel butanol yield with an algal hydrolysate, as compared to the wild-type strain. Fusel butanol possess the higher energy density, lower vapor pressure, lower hygroscopicity than fuel ethanol and has been considered as an advanced fuel compounds (see, e.g., Lan E I et al., "Microbial synthesis of n-butanol, isobutanol, and other higher alcohols from diverse resources," *Bioresour. Technol.* 2013; 135:339-49; and Smith K M et al., "An evolutionary strategy for isobutanol production strain development in *Escherichia coli,"* *Metab. Eng.* 2011; 13(6):674-81). Recently, algal protein hydrolysates were reported into fusel butanol but at a relative low titer (see, e.g., Huo Y X et al., *Nat. Biotechnol.* 2011; 29(4):346-51). One of possible factors that results in the lower fusel titer could be the co-factor imbalance during the fermentation, in which strategies to address these factors are described herein.

Example 4: Bioconversion of Distillers' Grains Hydrolysates to Advanced Biofuels by an *Escherichia coli* Co-Culture Global bioethanol production reached 25.7 billion gallons in 2015, with further increase in annual production projected. During the ethanol refining process, starch in the grain flour is converted into ethanol and the remainder of the grain components, such as proteins, lipids and fibers comprise a residual coproduct, commonly known as distillers' grains with solubles (DGS) (see, e.g., Bothast R J et al., "Biotechnological processes for conversion of corn into ethanol," *Appl. Microbiol. Biotechnol.* 2005; 67:19-25). It is estimated that in the dry milling process, the utilization of a bushel of corn (56 lb) results in 2.8 gallon of ethanol and 18 lb of DGS. In 2015, 40 million metric tons of DGS were produced from US ethanol biorefineries.

First generation bioethanol production utilizes the starch fraction of maize, which accounts for approximately 60% of the ash-free dry weight of the grain. Scale-up of this technology for fuels applications has resulted in a massive supply of DGS coproduct, which is considered as a rich source of cellulosic polysaccharides (52-57%), protein (27-31%), oil (10-12%) and other nutrients (see, e.g., Bothast R J et al., *Appl. Microbiol. Biotechnol.* 2005; 67:19-25) and has long been marketed as a ruminant feed adjunct. However, due to the variability in nutrient content, inconsistency of the product stream, and digestibility issues, as well as other concerns such as mycotoxins, antibiotic residues, sulphur content, and the risk of introducing bacterial pathogens (see, e.g., Liu K S, "Chemical composition of distillers grains, a review," *J. Agric. Food Chem.* 2011; 59:1508-26), acceptance of DGS in the feed industry has been limited. Alternatively, because of its vast supply and sugar and protein content, DGS is a potentially promising biomass source for upgrading to valuable fuel products using bioconversion strategies that are compatible with the established starch ethanol process. Therefore, efficient valorization of DGS to produce value-added products (e.g., petroleum displacing products) could significantly improve the techno-economic feasibility of the established starch bioethanol process.

Recent advances in synthetic biology, metabolic engineering, and systems biology, have enabled rapid progress in developing microbial factories (see, e.g., Zhou Y J et al., "Production of fatty acid-derived oleochemicals and biofuels by synthetic yeast cell factories," *Nat. Commun.* 2016; 7:11709 (9 pp.); Liao J C et al., "Fuelling the future: microbial engineering for the production of sustainable biofuels," *Nat. Rev. Microbiol.* 2016; 14:288-304; and Chubukov V et al., "Synthetic and systems biology for microbial production of commodity chemicals," *npj Syst. Biol. Appl.* 2016; 2:16009 (11 pp.)) and novel enzyme cascade systems (see, e.g., Liu F et al., "Functional assembly of a multi-enzyme methanol oxidation cascade on a surface-displayed trifunctional scaffold for enhanced NADH production," *Chem. Commun.* 2013; 49:3766-8; Park M et al., "Positional assembly of enzymes on bacterial outer membrane vesicles for cascade reactions," *PLoS One* 2014; 9:e97103 (6 pp.); and Dueber J E et al., "Synthetic protein scaffolds provide modular control over metabolic flux," *Nat. Biotechnol.* 2009; 27:753-9) for the synthesis of biofuels and other chemicals.

When considering a microbial system for biomass conversion, although there are successful examples in developing 'superbugs' capable of multiple functions, engineering a single microbe to simultaneously perform multiple tasks is still quite challenging and bioenergetically costly under most situations, especially when utilizing complex substrates or performing complicated biosynthesis. Alternatively, well-designed microbial consortia involving two or more microbes that can take advantage of individual microbes and their interactions to realize synergistic division of labor and more efficient utilization of biochemical substrates, and therefore exhibit better properties than monocultures, could provide enhanced productivity, stability or metabolic efficiency (see, e.g., Bizukojc M et al., "Metabolic modelling of syntrophic-like growth of a 1,3-propanediol producer, *Clostridium butyricum*, and a methanogenic archeon, *Methanosarcina mazei*, under anaerobic conditions," *Bioprocess Biosyst. Eng.* 2010; 33:507-23; Qu Y et al., "Use of a coculture to enable current production by *Geobacter sulfurreducens*," *Appl. Environ. Microbiol.* 2012; 78:3484-7; and Zhang H et al., "Engineering *Escherichia coli* coculture systems for the production of biochemical products," *Proc. Nat'l Acad. Sci. USA* 2015; 112:8266-71)

Ethanol has been successfully produced as a fuel product from the sugar fractions in pretreated DGS hydrolysates by an engineered yeast (see, e.g., Kim Y et al., "Enzyme hydrolysis and ethanol fermentation of liquid hot water and AFEX pretreated distillers' grains at high-solids loadings," *Bioresour. Technol.* 2008; 99:5206-15). Recent studies suggest that fusel alcohols, primarily isobutanol (C4) and iso-pentanols ($C_5$), which contain higher carbon content than ethanol ($C_2$) have improved physical properties and higher energy densities than ethanol and are therefore considered as compatible, and in some cases, superior gasoline blending agents than ethanol (see, e.g., Sarathy S M et al., "Alcohol combustion chemistry," *Prog. Energy Combust. Sci.* 2014; 44:40-102).

Here, we developed an *E. coli* co-culture that is capable of simultaneously converting sugars as well as proteins in the DGS hydrolysates to produce fusel alcohols. In the engineered co-culture system, one *E. coli* strain was constructed for efficient conversion of hexose and pentose sugars in the DGS hydrolysates to isobutanol and other fusel alcohols. The second *E. coli* strain was modified for efficient utilization of the proteins in the DGS hydrolysates to produce mixed C4 and C5 alcohols.

Figure 14A:
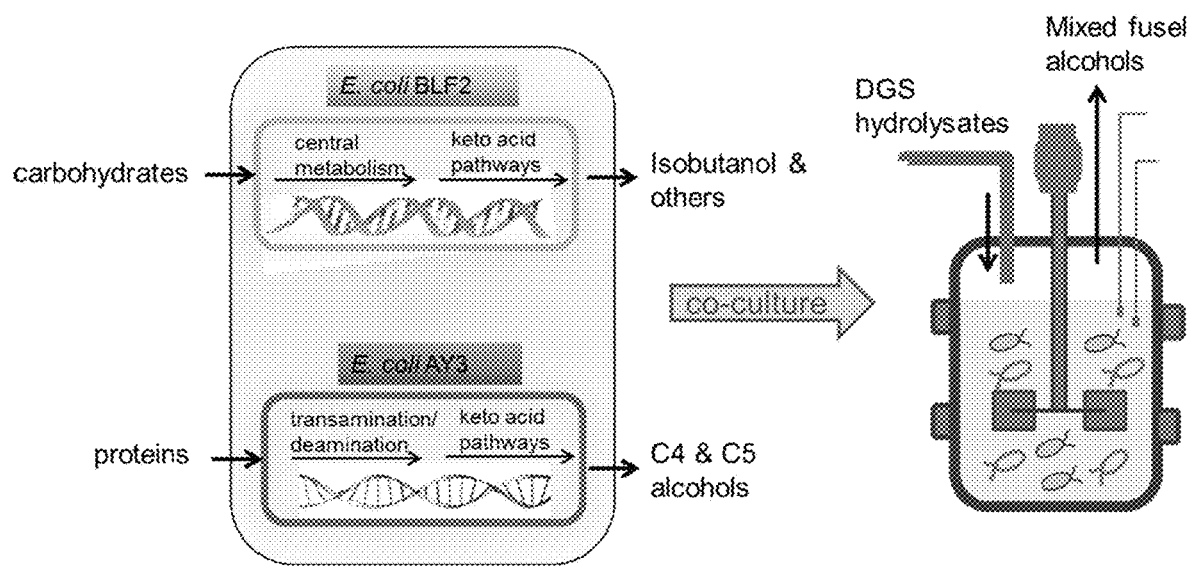
FIG. 14A-14C shows use of an exemplary microbial co-culture for DGS conversion. Provided are (A) an exemplary schematic of one-pot bioconversion of DGS hydrolysates into advanced biofuels by an engineered E. coli co-culture. Also provided are (B) two constructed exemplary plasmids containing the genes encoding for the five enzymes involved in the isobutanol production pathway and (C) an exemplary schematic of a 2-keto acid pathways for fusel alcohol production from glucose and xylose in E. coli BLF2. The five genes overexpressed and the corresponding higher fusel alcohol products are annotated with gray boxes. Abbreviations are as follows: AlsS (acetolactate synthase), IlvC (acetohydroxy acid isomeroreductase), IlvD (dihydroxy-acid dehydratase), Kdc (2-ketoacid decarboxylase), Adh (alcohol dehydrogenase), Ldh (lactate dehydrogenase), Pta (phosphotransacetylase), Ack (acetate kinase), KIV (2-ketoisovalerate), KIC (2-ketoisocaproate), KV (2-ketovalerate), KB (2-ketobutyrate), and KMV (2-keto-3-methylvalerate).

By co-culturing these two *E. coli* strains, we demonstrated 'one-pot' bioconversion of the protein and carbohydrate fractions of DGS hydrolysate into advanced biofuels (FIG. 14A). As described herein, the carbohydrate conversion strain *E. coli* BLF2 was constructed from the wild type *E. coli* strain B and showed improved capability to produce fusel alcohols from hexose and pentose sugars. Up to 12 g/L fusel alcohols was produced from glucose or xylose synthetic medium by *E. coli* BLF2. The second strain, *E. coli* AY3, was dedicated for utilization of proteins in the hydrolysates to produce mixed C4 and C5 alcohols. To maximize conversion yield by the co-culture, the inoculation ratio between the two strains was optimized. The co-culture with an inoculation ratio of 1:1.5 of *E. coli* BLF2 and AY3 achieved the highest total fusel alcohol titer of up to 10.3 g/L from DGS hydrolysates. The engineered *E. coli* co-culture system was shown to be similarly applicable for biofuel production from other biomass sources, including algae hydrolysates. Furthermore, the co-culture population dynamics revealed by quantitative PCR analysis indicated that despite the growth rate difference between the two strains, co-culturing didn't compromise the growth of each strain. The q-PCR analysis also demonstrated that fermentation with an appropriate initial inoculation ratio of the two strains was important to achieve a balanced co-culture population which resulted in higher total fuel titer.

The efficient conversion of DGS hydrolysates into fusel alcohols could improve the feasibility of the first-generation bioethanol process. The integrated carbohydrate and protein conversion platform developed here can be applicable for the bioconversion of a variety of biomass feedstocks rich in sugars and proteins, as described below.

Example 5: Experimental Methods

Strains and Plasmids:

*Escherichia coli* strain B (ATCC 11303) was purchased from ATCC. *E. coli* AY3 was previously developed in our lab (see, e.g., Wu W et al., "Cofactor engineering of ketolacid reductoisomerase (IlvC) and alcohol dehydrogenase (YqhD) improves the fusel alcohol yield in algal protein anaerobic fermentation," *Algal Res.* 2016; 19:162-7). The mutant strain *E. coli* B01 with single deleted gene Δldh:: cam+ was constructed using the technique of one-step disruption of chromosomal genes (see, e.g., Datsenko K A et al., "One-step inactivation of chromosomal genes in *Escherichia coli* K-12 using PCR products," *Proc. Nat'l Acad. Sci. USA* 2000; 97:6640-5) using primers 5'-GGATGGCGATACTCTGCCATCCGTAAT TTT-TACTCCACTTCCTGCCAGTTTGTGTAGGCTG-GAGCTGCTTC-3' (SEQ ID NO:60) and 5'-CGCTAT-TCTAGTTTGTGATATTTTTCGCCACCACAAGGAGTG-GAAAATGTGA CATGGGAATTAGCCATGGTCC-3' (SEQ ID NO:61) from *E. coli* B strain.

To construct pLF101, part of the ilvD gene was PCR amplified using primers 5'-GTAAA AAATATGTTCCGCGCAGGTCC-3' (SEQ ID NO:62) and 5'-TTTATTTGATGCCTCTAGCA CGCGTACGCGTT-TAACCCCCCAGTTTC-3' (SEQ ID NO:63) using pYX90 (see, e.g., Huo Y X et al., "Conversion of proteins into biofuels by engineering nitrogen flux," *Nat. Biotechnol.* 2011; 29:346-51; generously provided by Professor James C. Liao from University of California, Los Angeles) as the template. The rrnB T1 terminator was amplified using primers 5'-ACGCGT GCTAGAGGCATCAAATAAAAC-3' (SEQ ID NO:64) and 5'-AGTGAGCGAGGAAGCGGA ATATATC-3' (SEQ ID NO:65) using pYX90 as the template. Then, the two fragments were assembled with SbfI and AvrII digested pYX90 to achieve pLF101-alaS-ilvC-ilvD using In-Fusion® HD Cloning Kit (Clontech, CA) following the manufacture's protocol.

To construct pLF102, part of the Amp$^R$ gene and pLacO1 region was amplified using primers 5'-GCAAAAAAGCGGTTAGCTCCTTCG-3' (SEQ ID NO:66) and 5'-CTCCTACTGT ATA-CATGGTATATCTCCTTGTCGACAATGAAT-TCGGTCAGTGCGTCCTG-3' (SEQ ID NO:67). The PCR fragment was assembled with PvuI and SalI digested pYX97 (see, e.g., Huo Y X et al., *Nat. Biotechnol.* 2011; 29:346-51; generously provided by Professor James C. Liao from University of California, Los Angeles) using In-Fusion® HD Cloning Kit (Clontech, CA).

The DNA sequences of the constructs were confirmed by DNA sequencing. The plasmids pLF101 and pLF102 were co-transformed into the *E. coli* strain B01, which generated the production strain *E. coli* BLF2.

Medium and Culture Conditions:

M9 medium containing 40 g/L glucose or 40 g/L xylose or 20 g/L glucose and 20 g/L xylose, 5 g/L yeast extract, 100 µg/mL ampicillin, 34 µg/mL chloramphenicol, and 25 µg/mL spectinomycin, and 1000th dilution of Trace Metal Mix A5 (Sigma-Aldrich, MO) was used for cell growth. The cells were inoculated in 3 mL medium in the test tube and incubated at 37° C. overnight at 250 rpm. Two hundred µL of the overnight culture was inoculated into 20 mL fresh medium in the shake flask and incubated at 37° C., 250 rpm. One mM isopropyl-β-d-thio-galactoside (IPTG) was added when $OD_{600}$ reached 0.8. Then, the culture was grown at 30° C. and 250 rpm for 2 days. Samples were collected at regular time intervals for further analysis.

Biomass Pretreatment and Fermentation:

The distillers' grains samples (35% solids) were provided by Aemetis, Inc. (Cupertino, Calif.) and pretreated following the protocols from the National Renewable Energy Laboratories. Briefly, DGS were mixed with 4% dilute sulfuric acid to a final concentration of 8.5% (w/v) solid. Then, the mixture was incubated in a 90° C. water bath for 5 h and neutralized with $Ca(OH)_2$ solids until pH reached 6.5. The resulting slurry was subsequently hydrolyzed with 1.5 mg/mL Pronase (Sigma-Aldrich, St. Louis, Mo.) following the manufacture's protocol. After enzymatic digestion, the slurry was centrifuged, and the supernatant was sterilized by filtration through the 0.22 µm PTFE membrane (Fisher Scientific, CA). *Nannochloropsis* sp. algae samples were pretreated similarly but incubated with 10% sulfuric acid. The resulting hydrolysates were used directly as the medium for cell growth and fusel alcohol production with no additional supplements.

*E. coli* BLF2 cells were cultivated in 10 mL LB medium and grown at 37° C., 250 rpm. The overnight culture was centrifuged at 4000 rpm for 10 min, and the cell pellets were collected and washed with corresponding hydrolysates twice and resuspended in 1 mL hydrolysates. About 0.8 mL of the mixture was inoculated into 20 mL DGS or algae hydrolysates supplemented with 100 µg/mL ampicillin, 34 µg/mL chloramphenicol, and 25 µg/mL spectinomycin. The culture was incubated at 37° C., 250 rpm and induced with 1 mM IPTG when the $OD_{600}$ reached 0.8. The flasks were cap-sealed and cultured for another 48 h at 30° C., 250 rpm, for fusel alcohol production. Samples were taken at the beginning and end of the fermentation for further analysis.

For co-culture fermentation, *E. coli* strains AY3 and BLF2 were cultivated in 10 mL LB medium separately. The overnight culture was centrifuged, and the final cell pellets were individually re-suspended into 0.5-1 mL hydrolysates and were both adjusted to the same $OD_{600}$. Then, various ratios of AY3 and BLF2 cells (0.5:1, 1:1, 1.5:1, 2:1, etc.) were inoculated into the DGS or algae hydrolysates at a final concentration of 20% (v/v). The induction and fermentation were performed as described above.

Analytical Methods:

To determine the concentrations of glucose, xylose and arabinose in the medium, as well as the products such as isobutanol and ethanol, culture of the grown cells was centrifuged at 13,000 rpm for 10 min, and 5 mL of the supernatant was injected into an Agilent HPLC system (1100 Series) equipped with the Rezex ROA-Organic Acid Sugar column (Phenomenex, CA). Other fusel alcohols, including 2-methyl-1-butanol, 3-methyl-1-butanol, and 2-phenylethanol, were extracted with ethyl acetate at the ratio of 1:1 (fermentation broth:ethyl acetate) with 2-methyl-1-pentanol as the internal reference. The ethyl acetate layer was collected for GC-MS analysis. One microliter of sample was injected into the injection port (250° C.) of an Agilent gas chromatography 6890N equipped with a 30 m×0.25 mm DB-WAXetr capillary column with a film thickness of 0.5 µm. The temperature of the column was programmed as follows: 40° C. for 4 min, increasing to 65° C. at 10° C./min and holding for 10 min, then increasing to 300° C. at 65° C./min and holding for 5 min. The carrier gas was ultra-high purity helium at a constant flow rate of 1.5 mL/min. The chromatograph was coupled to a quadrupole MS 5975B. Spectral components were searched against the Wiley275 mass spectral library.

The total amino acids and proteins in the pretreated DGS and *Nannochloropsis* sp. hydrolysates before and after fermentation were determined using the ninhydrin assay (see, e.g., Friedman M, "Applications of the ninhydrin reaction for analysis of amino acids, peptides, and proteins to agricultural and biomedical sciences," *J. Agric. Food Chem.* 2004; 52:385-406). The total carbohydrates in algae hydrolysates were determined by the phenol-sulfuric acid method (see, e.g., Masuko T et al., "Carbohydrate analysis by a phenol-sulfuric acid method in microplate format," *Anal. Biochem.* 2005; 339:69-72) using a glucose standard.

Real Time Quantitative PCR:

Primers for the species-specific sequences of BLF2 and AY3 strains were designed for the quantitative PCR reaction. Primers 5'-GCTTTAATGAGTGG AATCGCC-3' (SEQ ID NO:68) and 5'-GATGCAATGTTCTGGCTAACG-3' (SEQ ID NO:69) were used to specifically amplify the agaE gene of *E. coli* BLF2 strain. Primers 5'-GTGGAAA GAGGGCGATAAGAG-3' (SEQ ID NO:70) and 5'-TCATGACGTTGGTAGAAGCG-3' (SEQ ID NO:71) were used for the specific amplification of the malB gene of AY3 strain.

The q-PCR assays were carried out with the CFX96 Real-time PCR system with a $C_{1000}$ Thermal Cycler (Bio-Rad, CA). The reaction mixture of 20 µL final volumes contained 1 µL DNA template, 0.15 µM each respective primer, and 10 µL of SYBR Green Master Mix (Bio-Rad, CA). All amplifications were carried out in optical grade 96 well plates (Fisher Scientific, MA) with an initial step at 98° C. for 3 min followed by 35 cycles of 98° C. for 15 s, and 59° C. for 30 s. At the completion of each run, melting curves for the amplicons were measured by raising the temperature 0.5° C. from 65° C. to 95° C. while monitoring fluorescence. The specificity of the PCR amplification was checked by examining the melting curve for $T_m$ and the lack of non-specific peaks. All tests were conducted in triplicate.

Cell Number Determination in the Co-Culture:

The cell numbers of *E. coli* BLF2 and AY3 in the co-culture were determined by the PCR-based multiple species cell counting method as described by Huang R et al., "PCR-based multiple species cell counting for in vitro mixed culture," *PLoS One* 2015; 10:e0126628 (13 pp.). To prepare the reference mixed samples, *E. coli* BLF2 and AY3 were grown overnight in 3 mL LB medium respectively. Then, their individual colony forming units per mL (CFU/mL) were determined using serial dilutions and plating method. The genomic DNA of the individual samples was extracted using the Quick-DNA Fungal/Bacterial Miniprep Kit (Zymo Research, CA) and the same amount (by volume) of DNA solution extracted from the two species was mixed and the threshold cycle $C_{T,R}$ was determined by quantitative PCR. For the unknown mixed samples, the genomic DNA of 2 mL fermentation culture was extracted, and q-PCR was performed to determine the CT,X as described above.

The cell numbers of *E. coli* BLF2 and AY3 in the co-culture samples during the fermentation process are deter-mined by the following equation modified from Huang R et al., *PLoS One* 2015; 10:e0126628 (13 pp.). (the genomic DNA of the reference samples and unknown co-culture samples have the same dilution for q-PCR reaction):

$$N_X = (1+E)^{C_{T,R}-C_{T,X}} \times CFU_R \times V_R \qquad \text{(Eq. 1)}$$

wherein $N_X$ is the cell number of *E. coli* BLF2 or AY3 in the co-culture; E is the amplification efficiency of the q-PCR reaction using the primers specific to BLF2 or AY3; $C_{T,R}$ is the number of threshold cycles ($C_T$) of q-PCR for BLF2 or AY3 in the reference sample; $C_{T,X}$ is the number threshold cycles ($C_T$) of q-PCR for BLF2 or AY3 in the unknown co-culture sample; $CFU_R$ is the cell concentration of BLF2 or AY3 reference sample; and $V_R$ is the volume of processed reference cells for DNA extraction.

Example 6: Strain Development for Co-Culture

*E. coli* strain AY3 previously developed in our lab (see, e.g., Wu W et al., "*Algal Res.* 2016; 19:162-7; and described herein) was used for the conversion of the protein fractions in the DGS hydrolysates into C4 and C5 fusel alcohols. *E. coli* AY3 is an improved strain of *E. coli* YH83, which was engineered to deaminate proteins and was able to utilize amino acids as the sole carbon source for growth (see, e.g., Wu W et al., *Algal Res.* 2016; 19:162-7; and Huo Y X et al., *Nat. Biotechnol.* 2011; 29:346-51).

The mutant *E. coli* YH83 was the YH40 strain (BW25113/F' [traD36, proAB⁺, lacI^qZΔM15] ΔglnA, ΔgdhA ΔluxS ΔlsrA) overexpressing isobutanol biosynthesis pathway genes (alsS-ilvC-ilvD-kivd-yqhD) and amino acids degradation genes (ilvE, ilvA, sdaB, avtA, and LeuDH) in three separate plasmids pYX68, pYX90 and pYX97 (Table 2). The cofactor specificity of two key enzymes in the alcohol metabolic pathway has been modified through the directed evolution approach to create AY3 strain with improved fusel alcohol production yield.

TABLE 2

Bacterial strains and plasmids for co-culture experiments

| Designation | Relevant characteristics | Sources/references* |
|---|---|---|
| Plasmids | | |
| pYX68 | pSC101 ori; Chl^R; PrrnB; ilvE-ilvA-sdaB | Huo et al. |
| pYX90 | p15A ori; Spect^R; P_LlacO_1; alsS-ilvC-ilvD-avtA | Huo et al. |
| pYX97 | ColE1 ori; Amp^R; P_LlacO_1; leuDH-kivd-yqhD | Huo et al. |
| pLF101 | p15A ori; Spect^R; P_LlacO_1; alsS-ilvC-ilvD | Herein; Liu et al. |
| pLF102 | ColE1 ori; Amp^R; P_LlacO_1; kivd-yqhD | Herein; Liu et al. |
| Strains | | |
| *E. coli* DH5α | lacZDM15 recA | NEB |
| *E. coli* YH40 | BW25113/F' [traD36, proAB⁺, lacI^q ZΔM15] derivative with enhanced ability of amino acid utilization and with ΔglnA, ΔgdhA, ΔlsrA | Huo et al. |
| *E. coli* AY3 | *E. coli* YH40 with plasmids pYX68, pYX90 with the mutant genes and pYX97 with the mutant genes | Herein; Wu et al.; Huo et al. |
| *E. coli* B | Prototroph | ATCC 11303 |
| *E. coli* B01 | *E. coli* B Δldh::cam⁺ | Herein; Liu et al. |
| *E. coli* BLF2 | *E. coli* B01 with plasmids pLF101 and pLF102 | Herein; Liu et al. |

*Huo YX et al., "Conversion of proteins into biofuels by engineering nitrogen flux," Nat. Biotechnol. 2011;29:346-51; Wu W et al., "Cofactor engineering of ketol-acid reductoisomerase (IlvC) and alcohol dehydrogenase (YqhD) improves the fusel alcohol yield in algal protein anaerobic fermentation," Algal Res. 2016;19:162-7; and Liu F et al., "Bioconversion of distillers' grains hydrolysates to advanced biofuels by an *Escherichia coli* co-culture," Microb. Cell Fact. 2017;16:192 (14 pp.).

*Escherichia coli* strain B (ATCC 11303) was selected as the wild type in this study for constructing the fusel alcohol production strain for carbohydrate utilization, because of its natural ability to metabolize glucose as well as xylose sugars (see, e.g., Alterthum F et al., "Efficient ethanol production from glucose, lactose, and xylose by recombinant *Escherichia coli*," *Appl. Environ. Microbiol.* 1989; 55:1943-8).

Therefore, this strain offers the opportunity to convert both hexose and pentose sugars present in the DGS hydrolysates. First, the gene encoding lactate dehydrogenase (ldh) was deleted from the chromosome of *E. coli* strain B using the technique of one-step disruption of chromosomal genes and was replaced with the chloramphenicol resistance gene ($Cm^R$) from the plasmid pKD3 (see, e.g., Datsenko K A et al., *Proc. Nat'l/Acad. Sci. USA* 2000; 97:6640-5). The resulting strain *E. coli* B01 had resistance to chloramphenicol, which enabled it to be co-cultured with the protein conversion strain *E. coli* AY3 that requires three antibiotic selectable markers ($Cm^R$, $Amp^R$, $Sm^R$) to retain the plasmids.

Two plasmids for introducing the pathway into *E. coli* B01 strain for isobutanol production from 2-keto acid precursors were constructed. Plasmid pLF101($Sm^R$) contained the genes encoding for acetolactate synthase (AlsS) from *Bacillus subtilis*, acetohydroxy acid isomeroreductase (IlvC) and dihydroxyacid dehydratase (IlvD) from *E. coli* (see, e.g., Atsumi S et al., "Engineering the isobutanol biosynthetic pathway in *Escherichia coli* by comparison of three aldehyde reductase/alcohol dehydrogenase genes," *Appl. Microbiol. Biotechnol.* 2010; 85:651-7). The second plasmid pLF102 ($Amp^R$) contained the genes encoding for 2-ketoacid decarboxylase (Kdc) from *Lactococcus lactis* and alcohol dehydrogenase (Adh) from *E. coli* (see, e.g., Atsumi S et al., *Appl. Microbiol. Biotechnol.* 2010; 85:651-7).

Figure 14B:
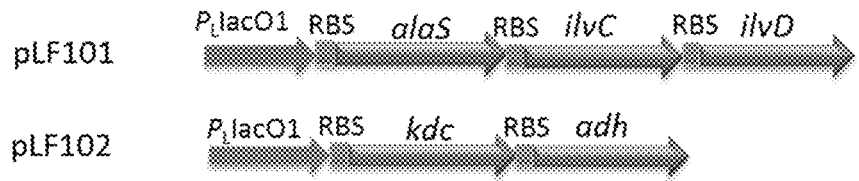
Figure 14C:
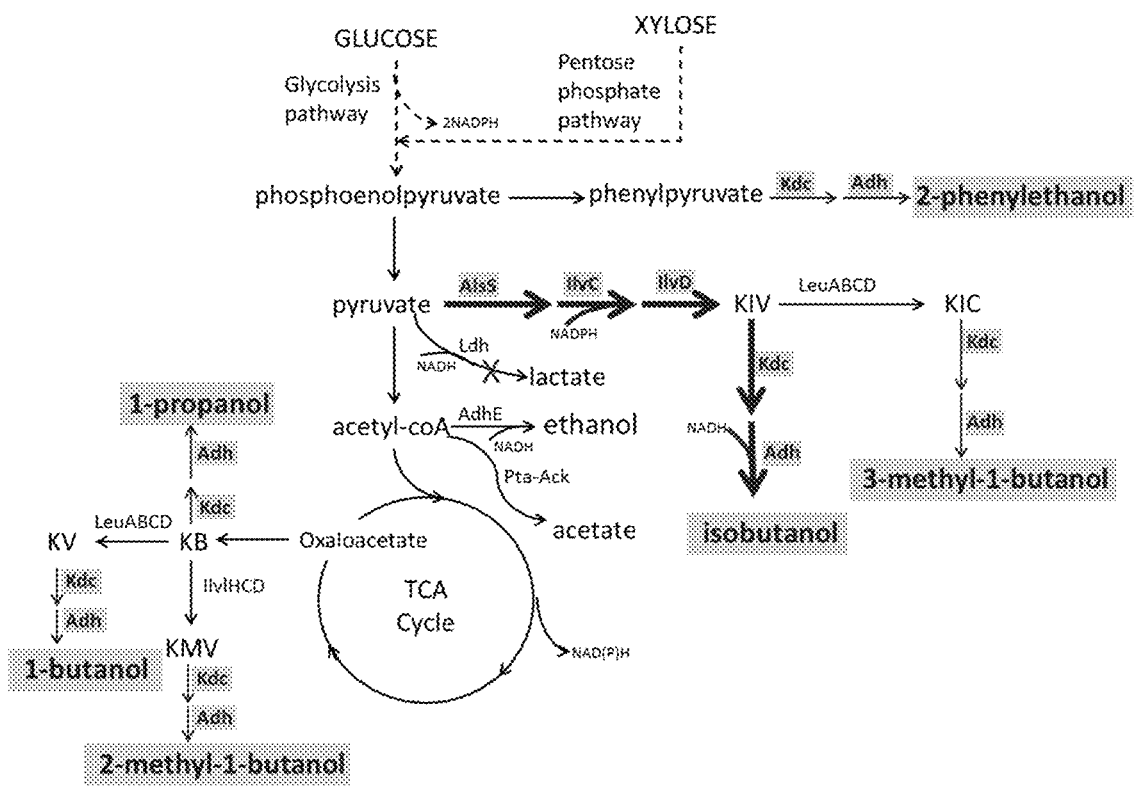

These two plasmids (pLF101 and pLF102) were co-transformed into *E. coli* B01 strain and the resulting strain. *Escherichia coli* BLF2 (Table 2) overexpressed the five genes involved in the isobutanol production pathway. Therefore, pyruvate produced from glucose and xylose is converted by AlsS, IlvC, and IlvD to 2-ketoisovalerate (KIV) which is further converted to isobutanol by Kdc (e.g., Kivd) and Adh (e.g., YqhD) (FIG. 14B). Although Kdc from *L. lactis* has the highest specific activity towards 2-ketoisovalerate, it can also use several other 2-keto acids as substrates with lower specific activities (see, e.g., de La Plaza M et al., "Biochemical and molecular characterization of α-ketoisovalerate decarboxylase, an enzyme involved in the formation of aldehydes from amino acids by *Lactococcus lactis*," *FEMS Microbiol. Lett.* 2004; 238:367-74). Therefore, besides isobutanol, other fusel alcohols such as 2-methyl-1-butanol and 3-methyl-1-butanol may also be produced from other 2-keto acid precursors, such as 2-ketoisocaproate (KIC) and 2-ketomethylvalerate (KMV) by Kdc and Adh, respectively (FIG. 14C).

Example 7: Fermentation of Glucose and Xylose Sugars by *E. coli* BLF2

Figure 15A:
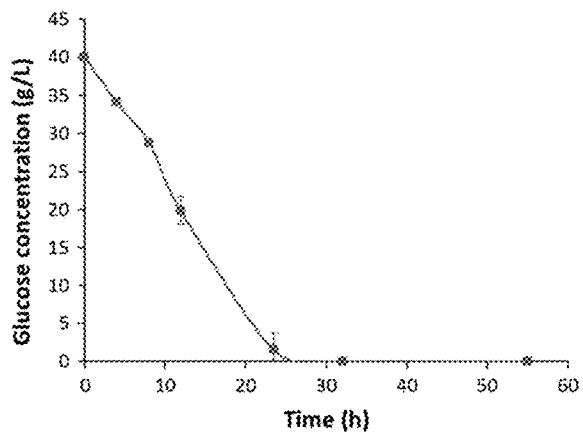
FIG. 15A-15D shows fermentation of glucose or xylose as a sole carbon source by E. coli BLF2. Provided are graphs showing (A) time-dependent glucose concentration in the medium during fermentation, (B) kinetic profiles of fusel alcohol production from glucose, (C) time-dependent xylose concentration in the medium during fermentation, and (D) kinetic profiles of fusel alcohol production from xylose. Abbreviations are as follows: Iso (isobutanol), Eth (ethanol), 2,1 (2-methyl-1-butanol), 3,1 (3-methyl-1-butanol), and Phe (phenylethanol).
Figure 15B:
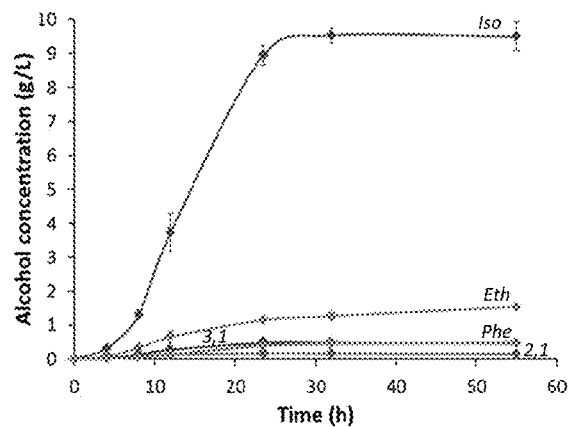

To evaluate isobutanol production yield from the engineered carbohydrate conversion strain *E. coli* BLF2, we used synthetic media which contained either glucose or xylose or glucose and xylose mixture as the sole carbon source for the cell growth. As analyzed by HPLC and GC-MS, the majority of the fermentation product of *E. coli* BLF2 was isobutanol (FIG. 15B). Other alcohols such as 2-methyl-1-butanol, 3-methyl-1-butanol, 2-pheny-lethanol and ethanol were also observed. At the end of the shake flask fermentation, a total of 12.1 g/L mixed fusel alcohols were produced from initial 40 g/L glucose, including 9.5 g/L isobutanol which comprised 80% of the alcohol mixture (FIG. 15B).

Figure 15C:
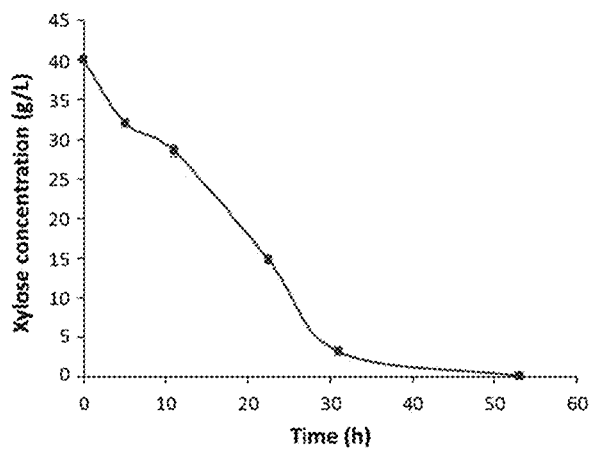
Figure 15D:
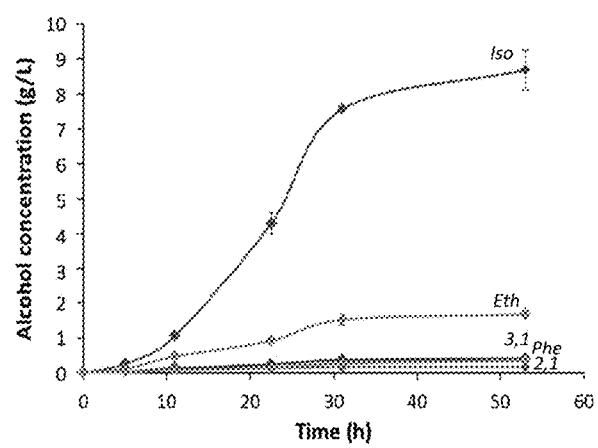

An average volumetric productivity of about 0.47 g/L h for the total alcohols was achieved when glucose was used as the sole carbon source. When growing in xylose medium, the xylose utilization rate was about 30% lower than glucose (FIG. 15A, 15C). Alcohol production with an average productivity of 0.32 g/L h was obtained which was similarly ~30% lower than that from glucose FIG. 15B, 15D).

Figure 16A:
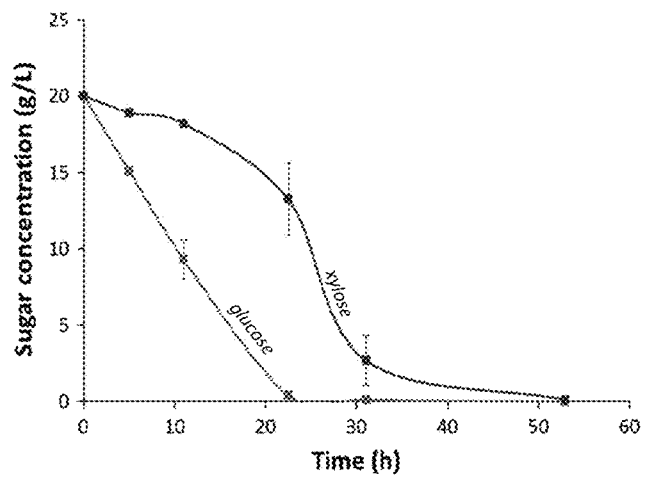
FIG. 16A-16B shows fermentation of a glucose and xylose mixture by E. coli BLF2. Provided are graphs showing (A) time-dependent glucose and xylose concentrations during the mixed sugar fermentation and (B) kinetic profiles of fusel alcohol production during the fermentation. Abbreviations are as follows: Iso (isobutanol), Eth (ethanol), 2,1 (2-methyl-1-butanol), 3,1 (3-methyl-1-butanol), and Phe (phenylethanol).
Figure 16B:
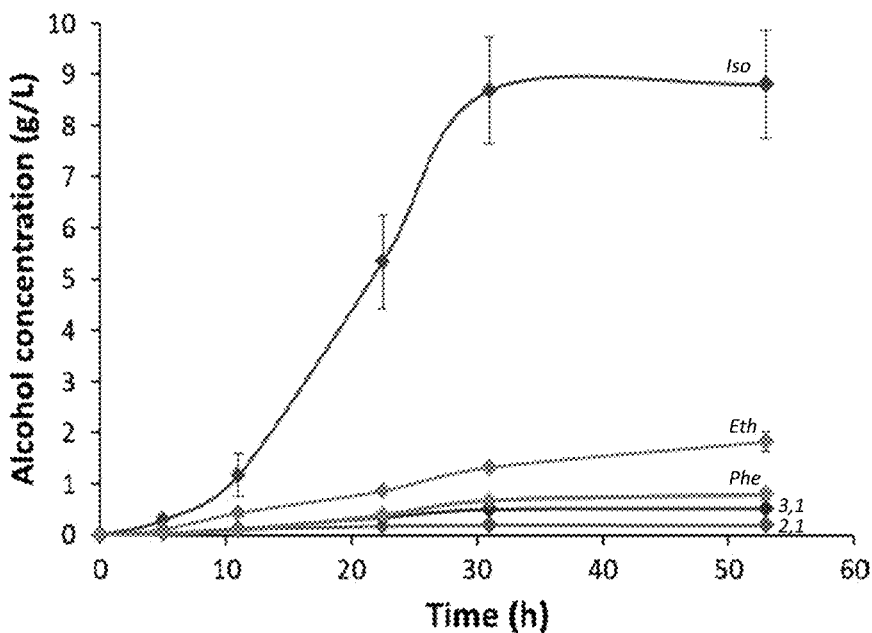

When sugar mixtures containing 20 g/L glucose and 20 g/L xylose was used as the growth medium, the cells preferably utilized glucose, and the utilization rate of xylose was slower than when it was fermented as a sole carbohydrate source (FIG. 16A), which suggests activation of carbon catabolite repression mechanisms (see, e.g., Kim J H et al., "Simultaneous consumption of pentose and hexose sugars: an optimal microbial phenotype for efficient fermentation of lignocellulosic biomass," *Appl. Microbiol. Biotechnol.* 2010; 88:1077-85). Glucose was completely exhausted after 20 h of cultivation while xylose was completely consumed after 50 h (FIG. 16A). The volumetric productivity for the total fuel alcohols from the sugar mixture was about 0.37 g/L h (FIG. 16B), which was lower than that from glucose but higher than when xylose was used as a sole carbon source.

Example 8: DGS Fermentation by *E. coli* BLF2

The kinetics of fusel alcohol production from carbohydrates present in DGS hydrolysates by *E. coli* BLF2 was evaluated from a time series study. The distillers' grains samples obtained from a bioethanol company (Aemetis, Inc.) were pretreated with 4% sulfuric acid at 8.5% solids loading. Dilute-acid based methods have been used for pretreatment of a variety of lignocellulosic substrates for facilitating conversion of oligosaccharides to monomeric sugars suitable for bacterial fermentation (see, e.g., Noureddini H et al., "Dilute-acid pretreatment of distillers' grains and corn fiber," *Bioresour. Technol.* 2010; 101:1060-7; Um B H et al., "Effect of sulfuric and phosphoric acid pretreatments on enzymatic hydrolysis of corn stover," *Appl. Biochem. Biotechnol.* 2003; 105-108:115-25; and Zhu Y et al., "Dilute-acid pretreatment of corn stover using a high-solids percolation reactor," *Appl. Biochem. Biotechnol.* 2004; 117:103-14).

Figure 17A:
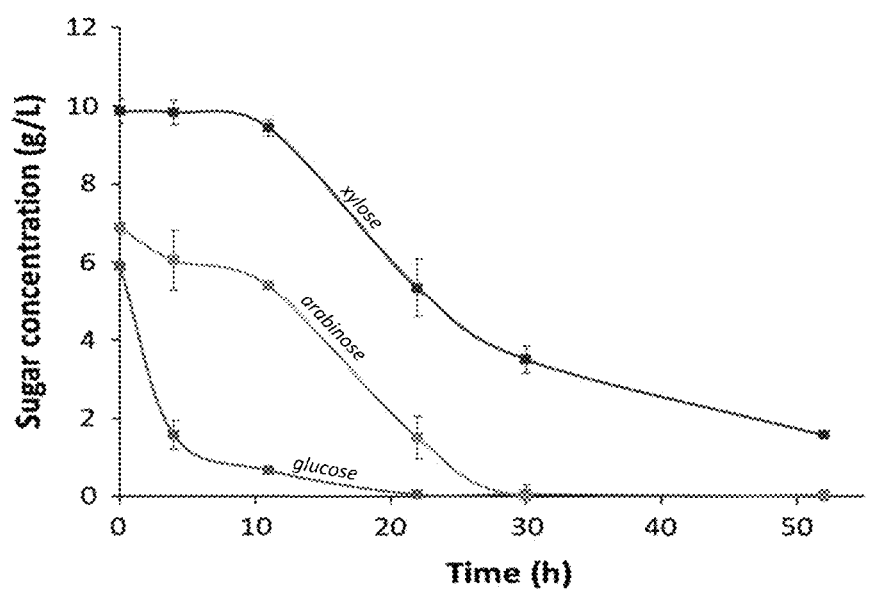
FIG. 17A-17C shows fermentation of pretreated DGS hydrolysates by E. coli BLF2. Provided are graphs showing (A) time-dependent glucose, xylose, and arabinose concentrations during the fermentation, (B) kinetic profiles of fusel alcohol production during the fermentation, and (C) compositions of the mixed fusel alcohols produced during the fermentation. Abbreviations are as follows: Iso (isobutanol), Eth (ethanol), 2,1 (2-methyl-1-butanol), 3,1 (3-methyl-1-butanol), and Phe (phenylethanol).

As analyzed by HPLC, the DGS hydrolysates after dilute-acid pretreatment contained 6 g/L glucose, 10 g/L xylose, and 7 g/L arabinose. The pretreated DGS hydrolysates without any additional supplement were used directly for BLF2 fermentation. During the fermentation course, glucose was preferentially utilized by the cells, and the uptake of xylose and arabinose was inhibited until glucose concentration was significantly attenuated (FIG. 17A), which suggests the inhibition of xylose and arabinose metabolism in the presence of glucose (i.e., catabolite repression).

Figure 17B:
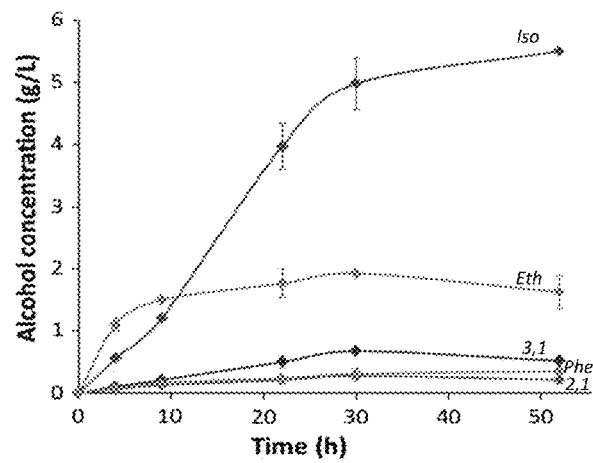
Figure 17C:
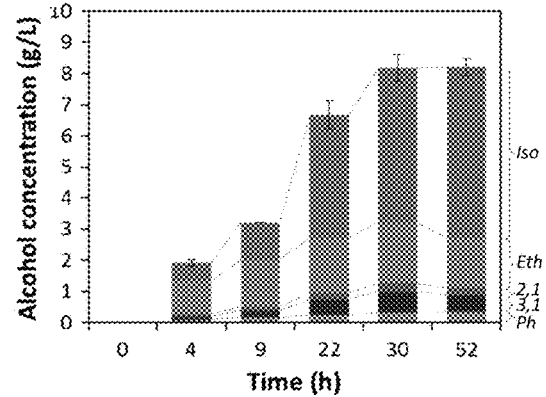

At the end of the 52 h fermentation, glucose and arabinose was completely consumed, while 84% of the total xylose in the hydrolysates was utilized with about 1.6 g/L unutilized. The conversion of the sugar fraction in the DGS hydrolysates by *E. coli* BLF2 resulted in a total of 8.2 g/L fusel alcohols including 5.5 g/L isobutanol, which was 67% of the mixed alcohols (FIG. 17B-17C).

Figure 18A:
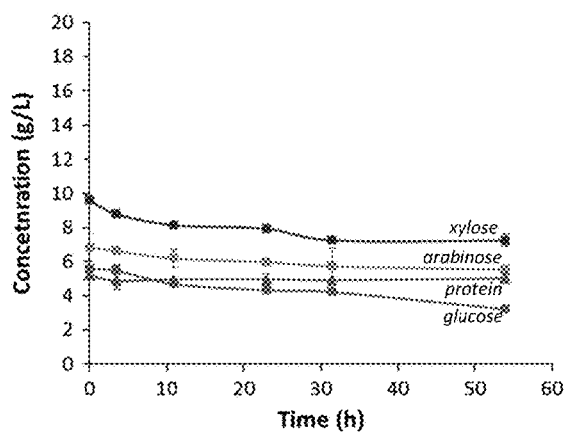
FIG. 18A-18D shows fermentation of pretreated DGS hydrolysates with and without Pronase digestion by E. coli AY3 strain. Provided are graphs showing (A) time-dependent sugar and protein concentrations during the fermentation of undigested DGS hydrolysate, (B) kinetic profiles of fusel alcohol production during the fermentation of undigested DGS hydrolysate, (C) time-dependent sugar and protein concentrations during the fermentation of DGS hydrolysate with Pronase digestion, and (D) kinetic profiles of fusel alcohol production during the fermentation of DGS hydrolysate with protease digestion. Abbreviations are as follows: Iso (isobutanol), Eth (ethanol), 2,1 (2-methyl-1-butanol), 3,1 (3-methyl-1-butanol), and Phe (phenylethanol).
Figure 18B:
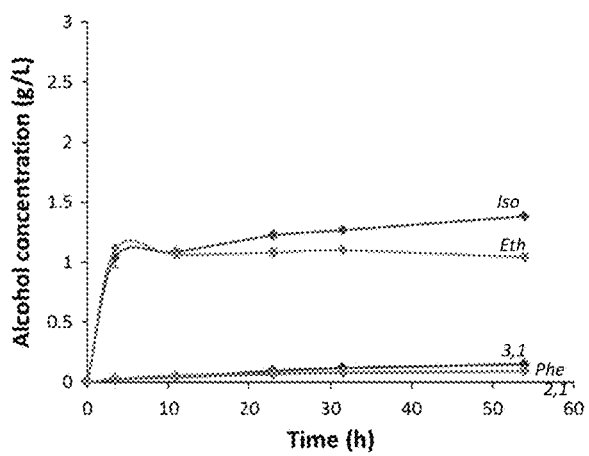
Figure 18C:
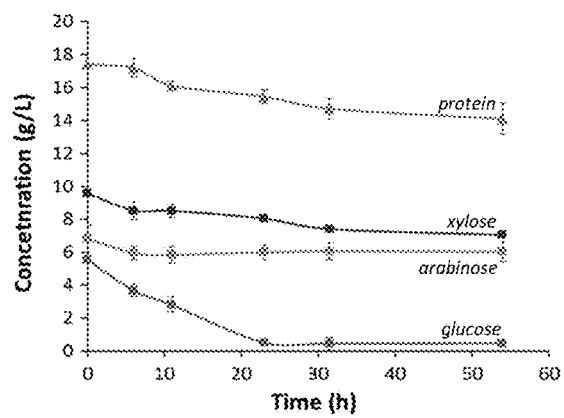

The protein conversion strain *E. coli* AY3 was previously engineered to utilize amino acids as carbon source for growth (see, e.g., Wu W et al., *Algal Res.* 2016; 19:162-7; and Huo Y X et al., *Nat. Biotechnol.* 2011; 29:346-51). Although it could also use glucose for growth, AY3 strain showed very limited ability in utilizing pentose sugars (xylose and arabinose) in the DGS hydrolysates (FIG. 18A, 18C).

Figure 18D:
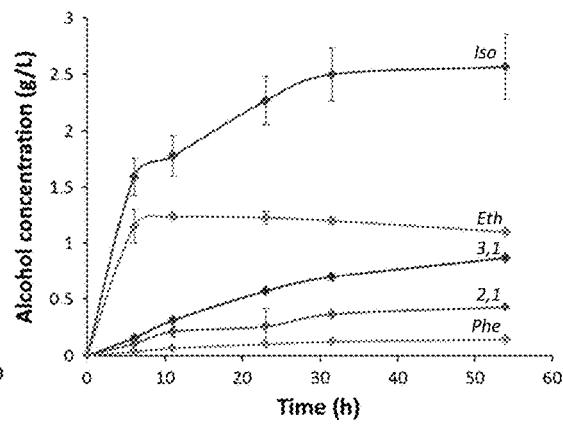

In the undigested DGS hydrolysates, there was about 5 g/L amino acids which remained unconverted as determined by the ninhydrin method (see, e.g., Friedman M, *J. Agric. Food Chem.* 2004; 52:385-406). AY3 only consumed 42% glucose and produced 2.8 g/L mixed fusel alcohols from the DGS hydrolysates without digestion (FIG. 18A-18B). After Pronase treatment, a total of 17.4 g/L free amino acid was released from the proteins in the DGS hydrolysates which can be utilized by *E. coli* AY3 as carbon source for growth. AY3 performed significantly better in the digested DGS hydrolysates and converted 3.3 g/L amino acids and 5.1 g/L glucose and produced a total of 5.1 g/L mixed fusel alcohols (FIG. 18C-18D).

Example 9: One-Pot Bioconversion of DGS Hydrolysate by *E. coli-E. coli* Co-Cultures Based on the techno-economic impact of reducing unit operations and increasing net conversion yields of the whole biomass hydrolysate, we investigated the feasibility of simultaneous bioconversion of protein and carbohydrate fractions in a 'one-pot' fermentation by co-culturing the two strains *E. coli* BLF2 and AY3. In the co-culture, *E. coli* BLF2 was dedicated for conversion of hexose and pentose sugars in DGS hydrolysates into C4 and C5 fusel alcohols, and *E. coli* AY3 was designated to convert DGS proteins into C4 and C5 fusel alcohols (FIG. 14A).

After dilute-acid pretreatment, the DGS hydrolysates were digested with Pronase to hydrolyze the proteins to monomeric amino acids or short peptides that can be readily utilized for co-culture fermentation. To optimize the inoculation ratio between the two strains in the co-culture system, the fusel alcohol yields were investigated under different initial BLF2/AY3 inoculation ratios at 0.5:1, 1:1, 1.5:1, and 2:1 as well as single strains of BLF2 or AY3 alone.

Figure 19A:
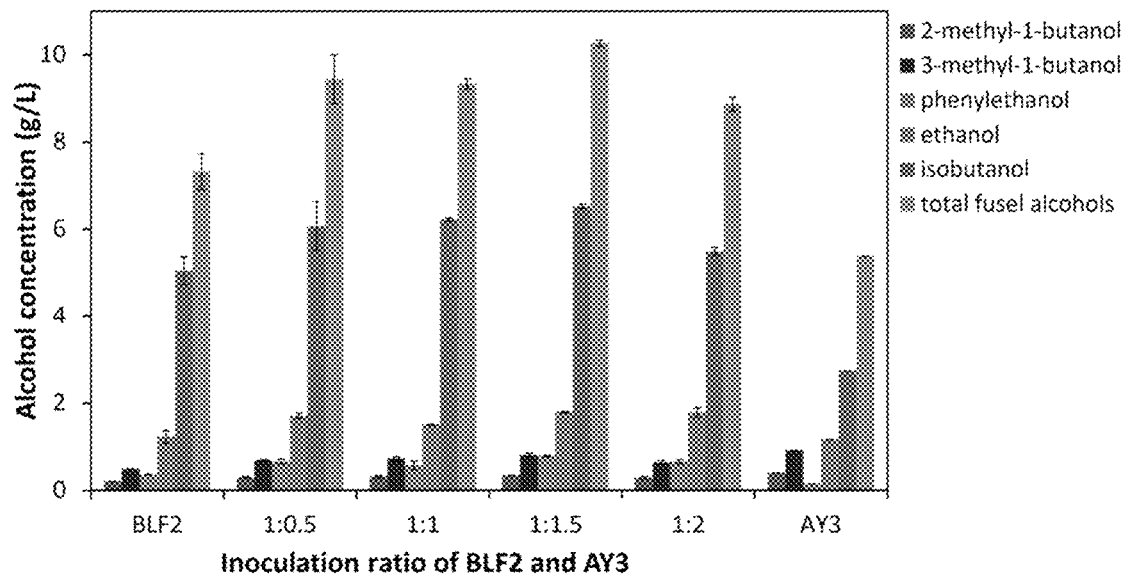
FIG. 19A-19D shows conversion of DGS hydrolysates by the co-culture of E. coli BLF2 and AY3 at different inoculation ratios. Provided are graphs showing (A) fusel alcohol production at 52 h and (B) its composition analysis, (C) the concentration of sugars in the hydrolysates before and after fermentation, and (D) the concentration of proteins in the hydrolysates before and after fermentation, in which the numbers provided above the bars indicate the percentages of protein converted. Abbreviations are as follows: Iso (isobutanol), Eth (ethanol), 2,1 (2-methyl-1-butanol), 3,1 (3-methyl-1-butanol), and Phe (phenylethanol).
Figure 19B:
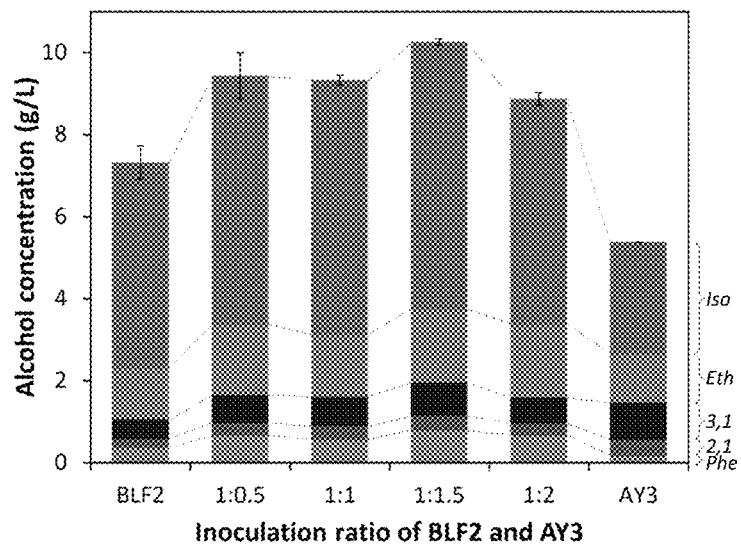
Figure 19C:
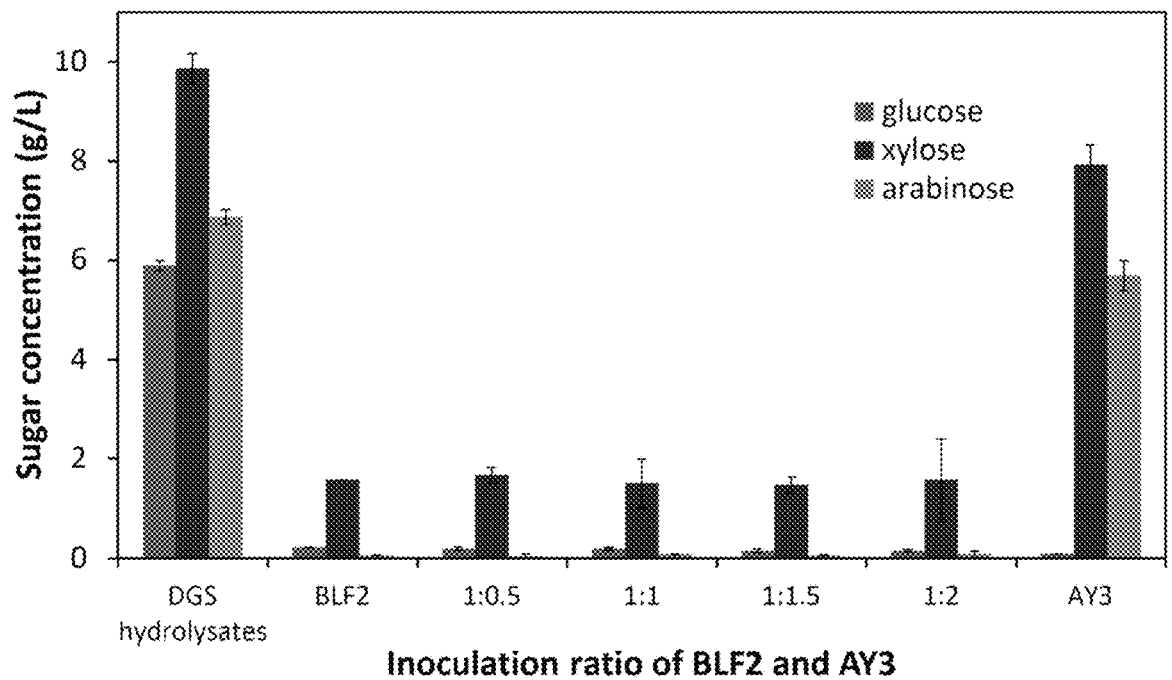
Figure 19D:
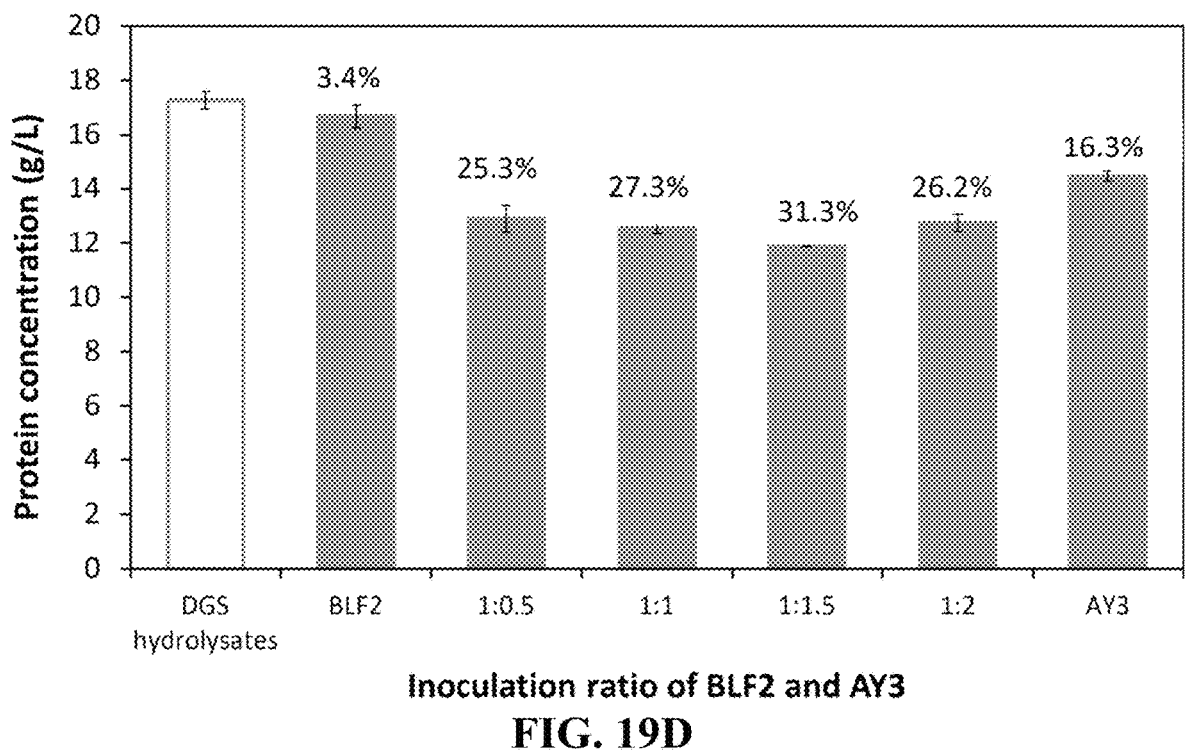

As shown in FIG. 19A-19B, when co-culture of the two strains were grown on DGS hydrolysates at an inoculation ratio of 1:1.5, the highest titer of total fusel alcohols up to 10.3 g/L was produced, including 6.5 g/L isobutanol which comprised 63.1% of the total alcohols. Correspondingly, the co-culture with the inoculation ratio of 1:1.5 consumed the highest total amount of carbohydrates and proteins in the hydrolysates (FIG. 19C-19D). The co-culture system resulted in nearly complete consumption of the glucose and arabinose and consumption of 85.1% of the xylose in the DGS hydrolysates (FIG. 19C). 31.3% of the total proteins in the hydrolysates were also converted by the co-culture with the inoculation ratio of 1:1.5 (FIG. 19D).

The co-cultures involving the two *E. coli* strains with different inoculation ratios all produced higher quantities of fusel alcohols than the monoculture BLF2 and AY3 alone, which indicated that both of the strains were contributing to the substrate conversion and fusel alcohol production. Although *E. coli* AY3 could uptake amino acids as the sole carbon source for growth, AY3 also utilized glucose for growth when monomeric sugars were present (FIG. 19C). Only 16.3% of the protein fraction in the DGS hydrolysates was converted by AY3 monoculture when sugars and proteins were both present in the hydrolysates (FIG. 19D). In contrast, higher conversion rates of proteins were achieved by the co-cultures, which indicated that the competition of BLF2 strain for sugar as carbon source induced AY3 to utilize more proteins for growth and alcohol production.

Example 10: Bioconversion of the Algae Hydrolysates by *E. coli* Co-Cultures

We further investigated the applicability of this microbial co-culture for the bioconversion of alternative hydro-lysates that are rich in carbohydrates and proteins, a prominent example of which is microalgae. *Nannochloropsis* sp. hydrolysates produced from dilute acid and enzymatic pre-treatment were inoculated with the BLF2-AY3 co-cultures at variable inoculation ratios. The algae hydrolysates were different from the DGS hydrolysates in that the latter contained a total of ~23 g/L fermentable sugars and ~17 g/L proteins, whereas the algae hydrolysates had a much higher fraction of proteins (~38 g/L) but much smaller amount of sugar with a total carbohydrate of ~5 g/L.

Figure 20A:
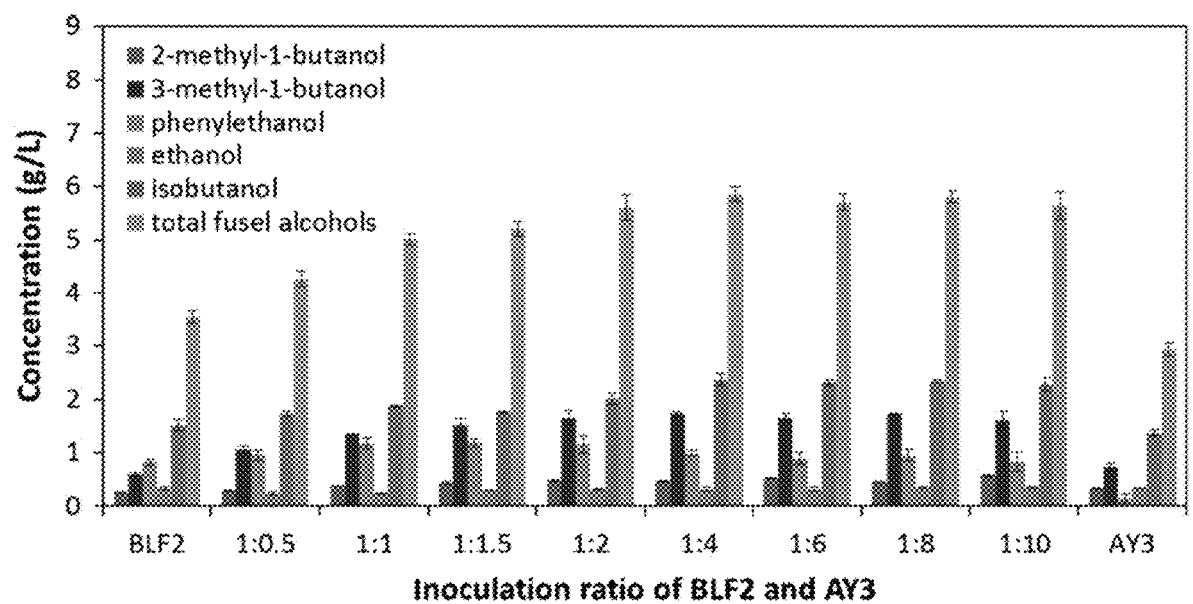
FIG. 20A-20D shows conversion of Nannochloropsis sp. algae hydrolysates by the co-culture of E. coli BLF2 and AY3 at different inoculation ratios. Provided are graphs showing (A) fusel alcohol production at 48 h and (B) its composition analysis, (C) the concentration of sugars in the hydrolysates before and after fermentation, in which the numbers showed the percentages of carbohydrate converted, and (D) the concentration of proteins in the hydrolysates before and after fermentation, in which the numbers provided above the bars indicate the percentages of protein converted. Abbreviations are as follows: Iso (isobutanol), Eth (ethanol), 2,1 (2-methyl-1-butanol), 3,1 (3-methyl-1-butanol), and Phe (phenylethanol).
Figure 20B:
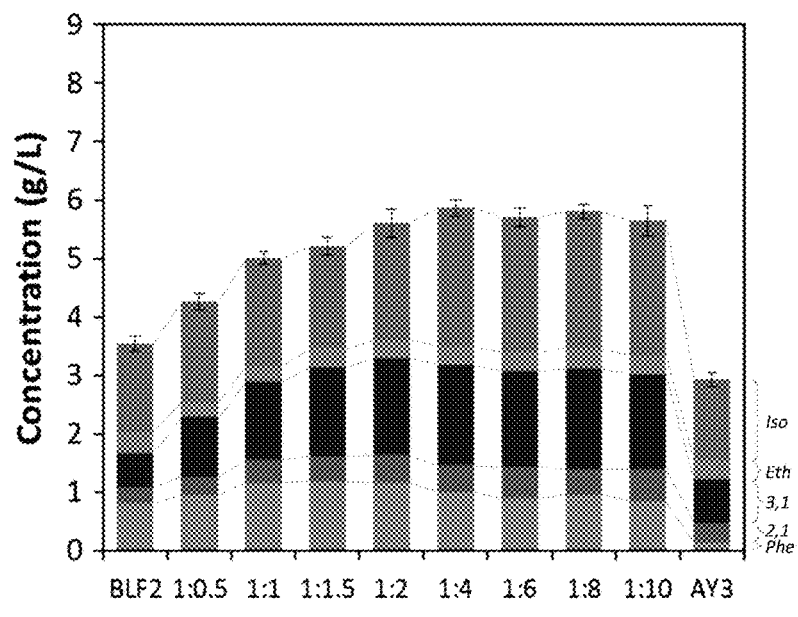
Figure 20C:
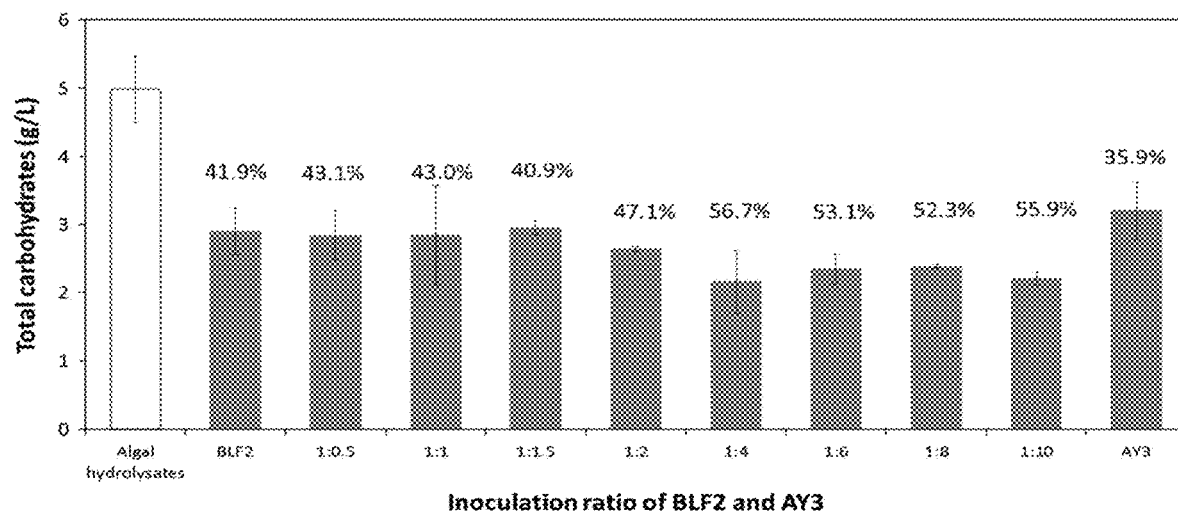

As shown in FIG. 20A, the co-culture with an inoculation ratio of 1:4, 1:6, 1:8 and up to 1:10 of BLF2 and AY3 produced higher amount of fusel alcohols. Furthermore, the 1:4 ratio led to the highest amount of mixed fusel alcohols, 5.9 g/L. The composition of the fusel alcohols products from algae hydrolysates included isobutanol (40.3% (w/w)) and mixed isopentanols (2-methyl-1-bu-tanol and 3-methyl-1-butanol (37.3% (w/w)), indicating significant enrichment of the C5 alcohols compared to the product spectrum produced from DGS, where isobutanol was the major product (63.1% (w/w)).

Figure 20D:
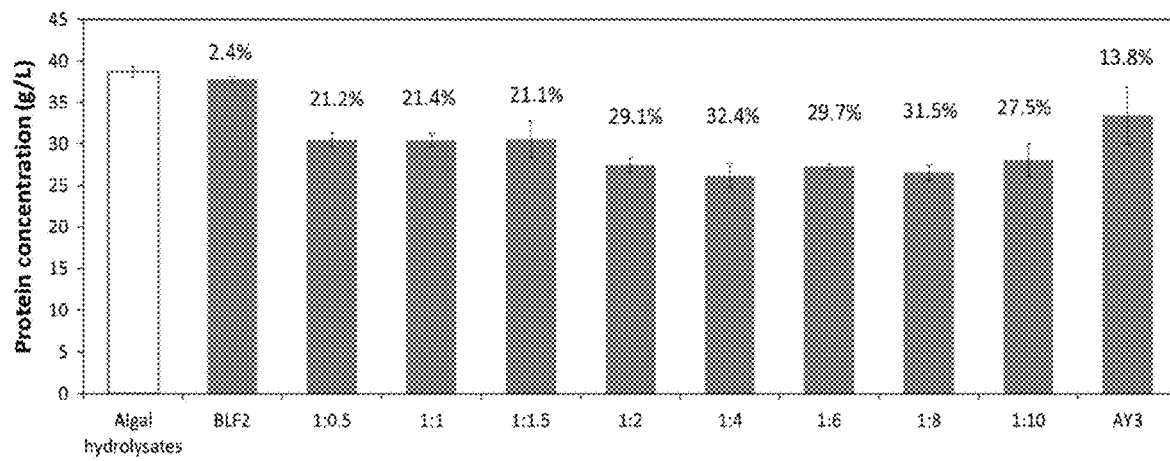
Figure 21A:
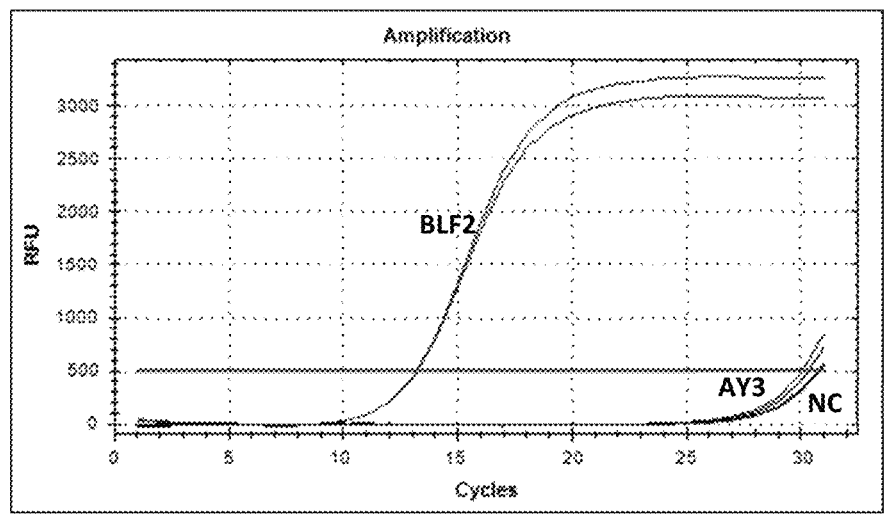
FIG. 21A-21D shows quantitative PCR (q-PCR) reactions for the amplification of BLF2 and AY3 genomic DNA and corresponding melt-curve analysis of the specificity of the reactions. Provided are graphs for (A) q-PCR reactions using primers specific to the araE gene of the BLF2 strain, (B) melting curve analysis of the q-PCR reactions in (A), in which the single peak indicates the absence of unspecific products, (C) q-PCR reactions using primers specific to malB gene of the AY3 strain, and (D) melting curve analysis of q-PCR reactions in (C). Shown are curves are the PCR reactions using BLF2 genomic DNA as templates (labeled "BLF2") and using AY3 genomic DNA as templates (labeled "AY3"), as well as negative control using deionized water as template (labeled "NC").
Figure 21B:
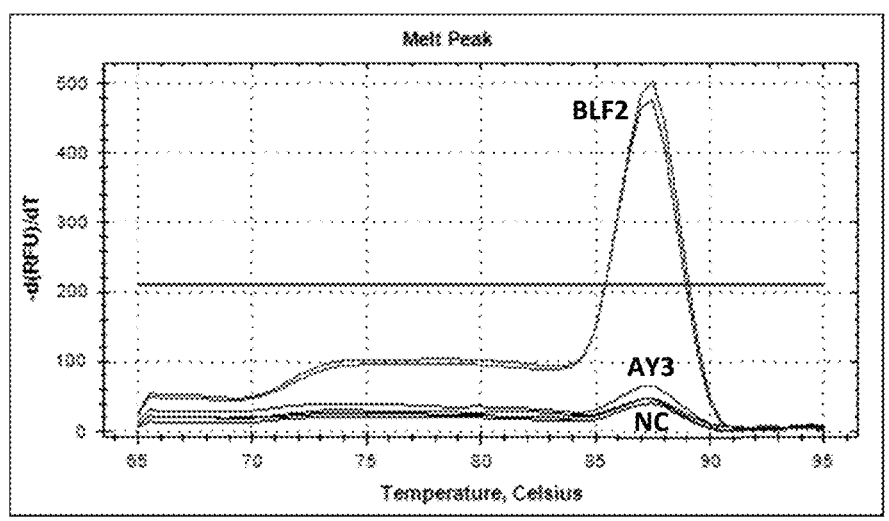
Figure 21C:
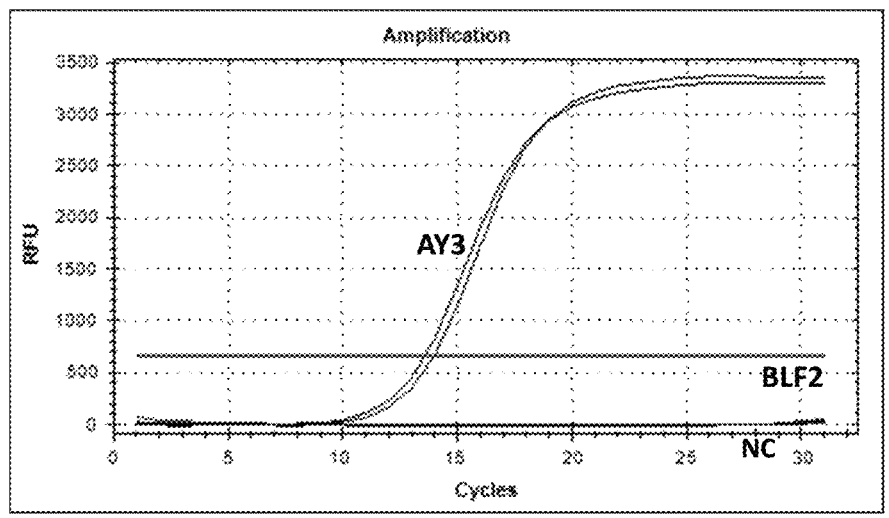
Figure 21D:
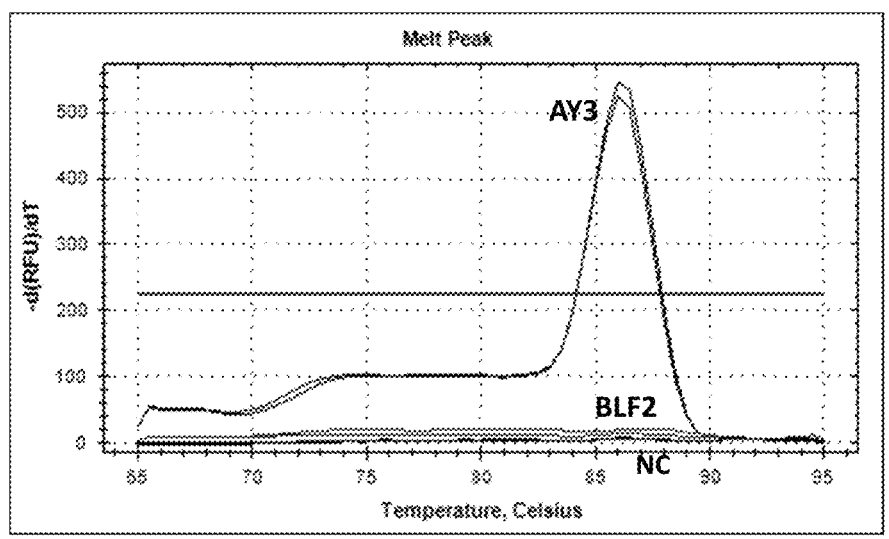
Figure 22A:
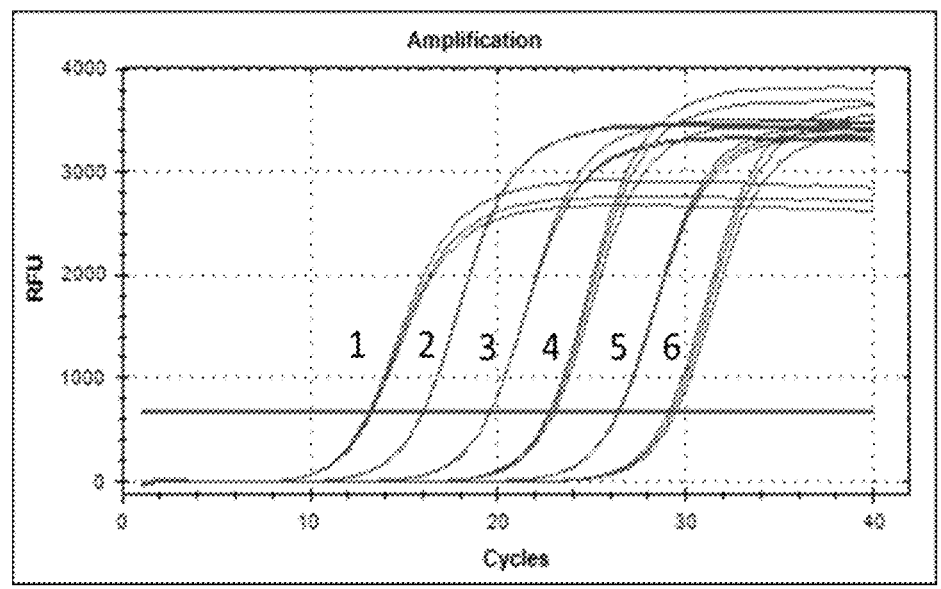
FIG. 22A-22D shows quantitative PCR (q-PCR) efficiency tests. Provided are graphs showing (A) q-PCR of 1:10 series dilution of the BLF2 genomic DNA samples, (B) the plot of $C_T$ for each 1:10 dilution as a function of the log of the starting quantity of BLF2 genomic DNA, in which the slope of line represents the q-PCR efficiency E of BLF2, (C) q-PCR of 1:10 series dilution of the AY32 genomic DNA samples, and (D) the plot of $C_T$ for each 1:10 dilution as a function of the log of the starting quantity of AY3 genomic DNA, in which the slope of line represents the q-PCR efficiency E of AY3.
Figure 22B:
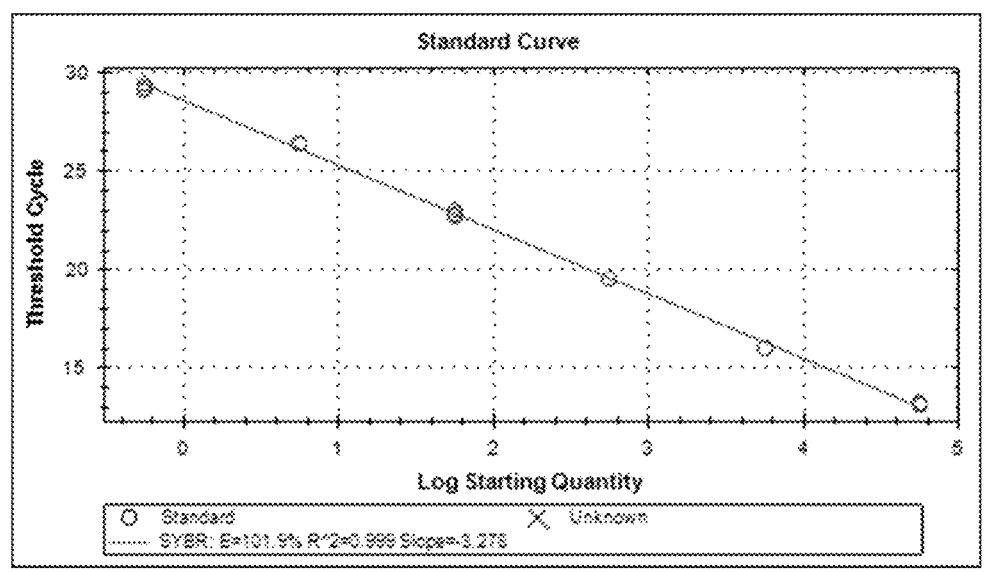
Figure 22C:
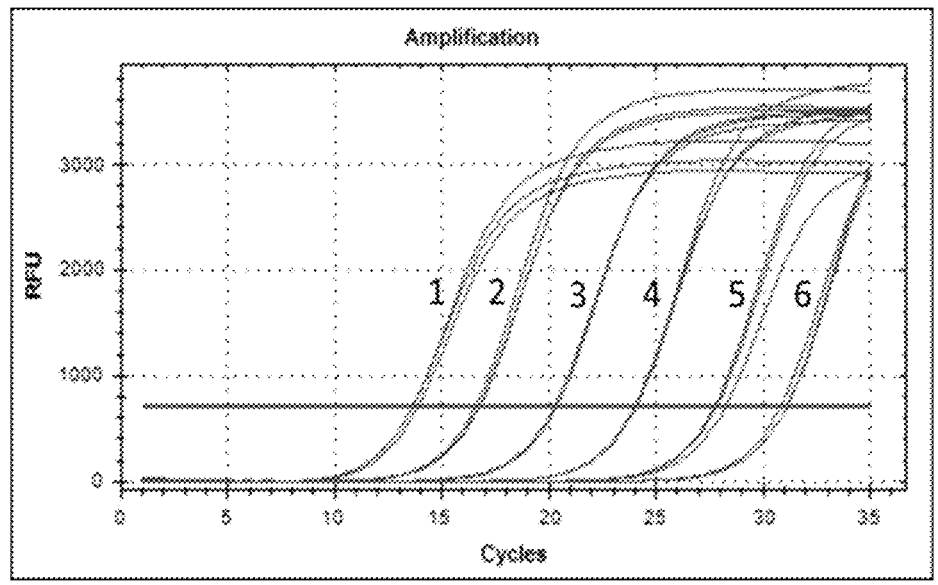
Figure 22D:
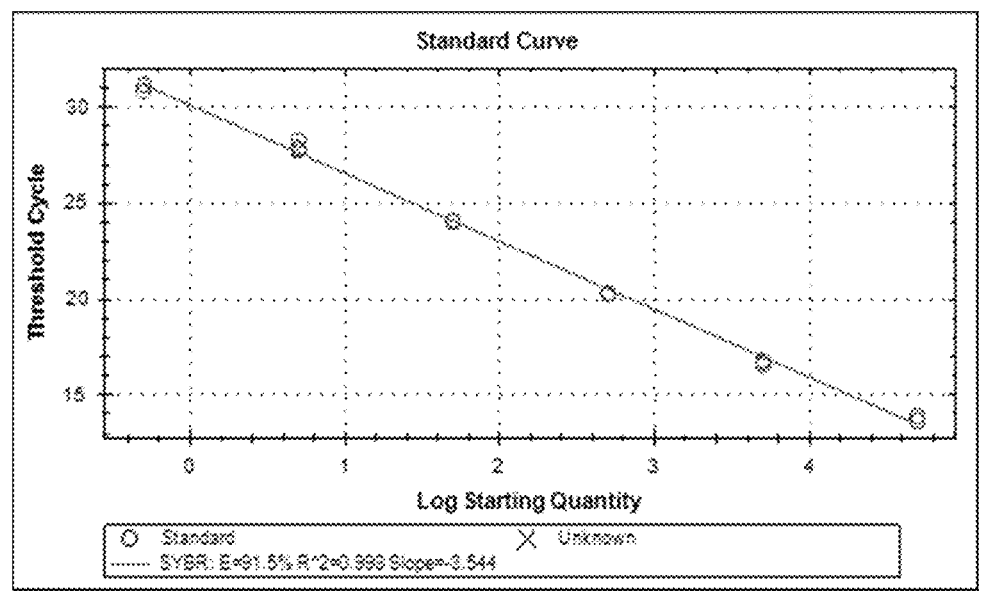

Since the alcohol mixture produced by AY3 monoculture had a higher fraction of isopentanol than that produced by BLF2 monoculture (FIGS. 19A-19B and FIGS. 20A-20B), this compositional change of the fuel products suggested that AY3 may have played a more significant role in the conversion of the algae hydrolysates in the co-culture than in DGS hydrolysates, which was also in agreement with the fact that algae hydrolysates had more proteins available for AY3 to utilize than in DGS hydrolysates. Up to 32.4% of the initial 38.7 g/L proteins in the algae hydrolysates were converted by the co-culture with an inoculation ratio of 1:4 (FIG. 20D).

Example 11: Dynamics of the Co-Culture by q-PCR Analysis

To differentiate BLF2 and AY3 strain in the co-culture and to monitor the cell number of each species during fermentation, specific primers targeting the unique genes in the chromosome of BLF2 and AY3 strain were designed. Although the *E. coli* strains have high nucleotide sequence homology and similar genome organization, BLF2 was engineered from wild-type B strain while AY3 was derived from the K-12 strain. *E. coli* B strain is deficient for malB gene encoding for the maltose high affinity receptor which is present in the K-12 strain (see, e.g., Studier F W et al., "Understanding the differences between genome sequences of *Escherichia coli* B strains REL606 and BL21(DE3) and comparison of the *E. coli* B and K-12 genomes," *J. Mol. Biol.* 2009; 394:653-80), while K-12 strain lacks the IID domain of the N-acetyl-galactosamine transporter (agaE) (see, e.g., Brinkkötter A et al., "Pathways for the utilization of N-acetyl-galactosamine and galactosamine in *Escherichia coli,*" *Mol. Microbiol.* 2000; 37:125-35). Therefore, the primers specific for malB and agaE were used to specifically target AY3 and BLF2 respectively. The specificity of the primers and validation of the q-PCR test was confirmed (FIG. 21A-21D). The parameters needed for calculating the cell numbers of BLF2 and AY3 in the co-culture as described in Example 5 herein were also determined (FIGS. 22A-22D and Table 3).

TABLE 3

Parameters for calculating the cell number of BLF2 and AY3 in the co-culture

| Target | E | $C_{T,R}$ | $CFU_R$ | $V_R$ |
|---|---|---|---|---|
| BLF2 | 1.019 | 14.79 | $1.09 \times 10^9$ | 2 |
| AY3 | 0.915 | 15.39 | $6.19 \times 10^8$ | 2 |

The cell numbers of BLF2 and AY3 in the co-culture at the end of fermentation were determined by the newly developed q-PCR based quantification method. As seen in Table 4, the cell number of AY3 grown in the DGS and algae hydrolysates was 3-tenfold lower than that of BLF2 alone, which indicates that AY3 grew more slowly than BLF2 strain. In the co-culture mixture, as the initial inoculation ratio of BLF2/AY3 decreased, the final BLF2/AY3 ratio in the co-culture at the end of fermentation also decreased in both of the hydrolysates. When more cells of BLF2 than AY3 were inoculated, for example at the 1:0.5 inoculation ratio, the final BLF2/AY3 ratio of 43.9 and 59.3 was observed for the DGS and algae hydrolysates, respectively (Table 4).

TABLE 4

Individual populations of BLF2 and AY3 in the co-culture at the end of fermentation of DGS or algae hydrolysates based on q-PCR analysis

| | DGS hydrolysate | | | Algae hydrolysates | | |
|---|---|---|---|---|---|---|
| Initial BLF2/AY3 inoculation ratio | Average cell number [cell/mL] in co-culture at 52 h | | Final BLF2/AY3 ratio in the co-culture at 52 h | Average cell number [cell/mL] in co-culture at 48 h | | Final BLF2/AY3 ratio in the co-culture at 48 h |
| | BLF2 | AY3 | | BLF2 | AY3 | |
| BLF2 alone | $3.2 \times 10^{10}$ | — | — | $2.0 \times 10^9$ | — | — |
| 1:0.5 | $1.8 \times 10^{10}$ | $4.1 \times 10^8$ | 43.9 | $3.5 \times 10^9$ | $5.9 \times 10^7$ | 59.3 |
| 1:1 | $2.7 \times 10^{10}$ | $6.9 \times 10^8$ | 39.1 | $2.8 \times 10^9$ | $8.8 \times 10^7$ | 31.8 |
| 1:1.5 | $8.2 \times 10^{10}$ | $5.6 \times 10^9$ | 1.5 | $1.9 \times 10^9$ | $9.3 \times 10^7$ | 20.4 |
| 1:2 | $1.9 \times 10^9$ | $1.6 \times 10^9$ | 1.2 | $1.5 \times 10^9$ | $2.5 \times 10^8$ | 6.0 |
| 1:4 | — | — | — | $1.5 \times 10^9$ | $4.0 \times 10^8$ | 3.8 |
| 1:6 | — | — | — | $9.6 \times 10^8$ | $2.8 \times 10^8$ | 3.4 |
| 1:8 | — | — | — | $1.5 \times 10^9$ | $4.6 \times 10^8$ | 3.3 |
| 1:10 | — | — | — | $1.2 \times 10^9$ | $6.5 \times 10^8$ | 1.8 |
| AY3 alone | — | $3.1 \times 10^9$ | — | — | $7.4 \times 10^8$ | — |

Only when more AY3 was initially inoculated, the difference of the cell numbers of the two species at the end of the fermentation was significantly reduced. When BLF2 and AY3 were inoculated at the ratio of 1:1.5 and 1:2, the final ratio of BLF2/AY3 reduced to 1.5 and 1.2, respectively (Table 4). Similarly, the difference of the cell numbers between the two species was reduced to less than fourfold at 48-h fermentation in the algae hydrolysates when AY3 was inoculated at least four times more cells than BLF2 in the co-culture (Table 4). The fusel alcohols produced by the co-culture at these inoculation ratios were higher than others, which suggests that a balanced population of the two strains during fermentation is important for the engineered co-culture to achieve higher fusel titers.

Figure 23A:
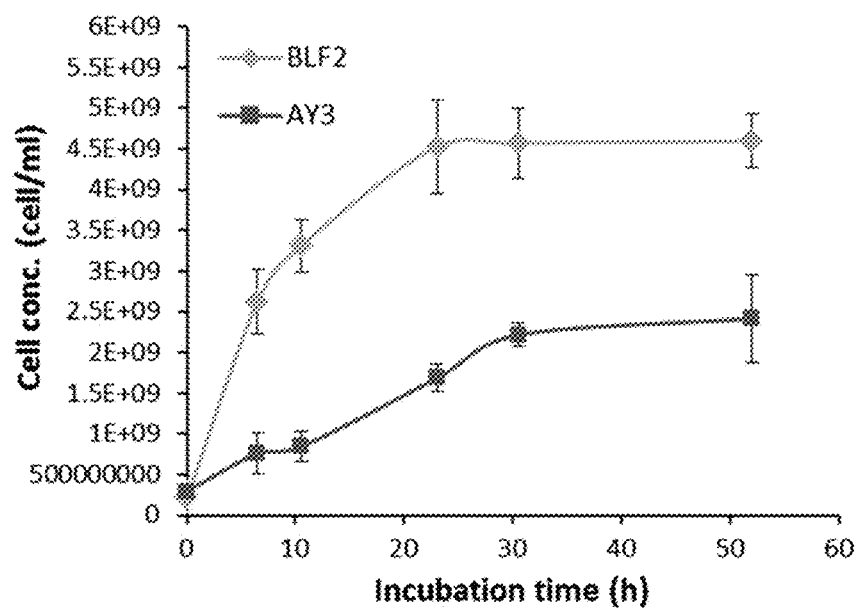
FIG. 23A-23B shows growth dynamics of individual populations in the co-culture during the fermentation of hydrolysates analyzed by the q-PCR quantification method. Provided are graphs showing (A) DGS hydrolysate with a BLF2/AY3 inoculation ratio of 1:1.5 and (B) algae hydrolysate with a BLF2/AY3 inoculation ratio of 1:4.
Figure 23B:
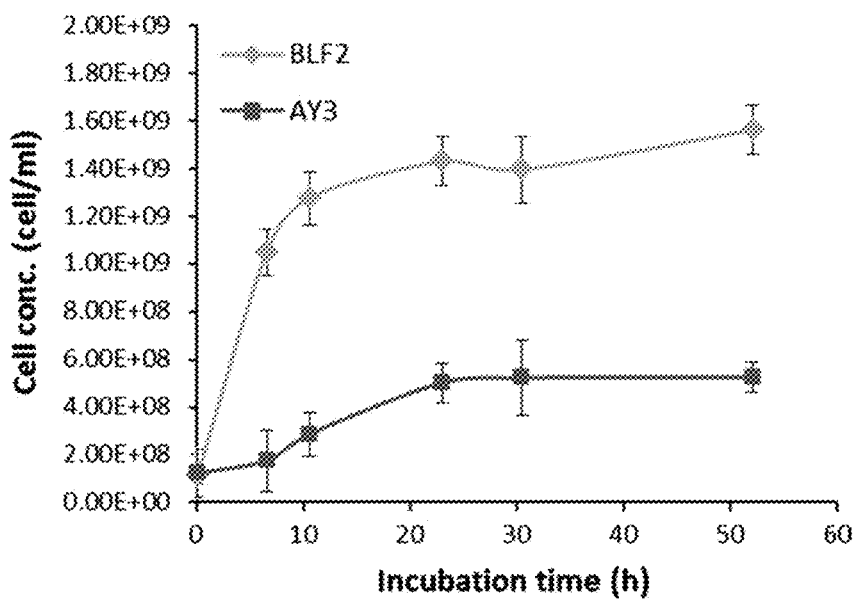

The q-PCR quantification method also provided the temporal profile of cell growth for the two E. coli strains in the co-culture during fermentation. Samples of different time points during fermentation of the DGS hydro-lysates with the initial BLF2/AY3 inoculation ratio of 1:1.5 and the algae hydrolysates with the inoculation ratio of 1:4 were collected respectively and the cell numbers were determined (FIG. 23A-23B). In both of the hydrolysates, the cell number of the two strains continuously increased until reaching plateau, which indicated that despite the growth rate difference between the two strains, the co-culturing didn't adversely affect the growth of each strain. Although BLF2 appeared as the dominant species in the co-culture, AY3 strain was not eliminated during the fermentation. In fact, the final cell numbers of AY3 in the co-cultures at proper inoculation ratios of BLF2/AY3 were no less than the cell number of AY3 monoculture in the hydrolysates (Table 4).

Example 12: Discussion Regarding Co-Culture Conversion

DGS, the major coproduct from the bioethanol industry, is produced in large and increasing quantities annually. Efficient valorization of DGS to support starch bioethanol process viability requires processes to convert both of the major DGS biochemical pools (e.g., proteins and carbohydrates) to value-added products. In this study, we developed a microbial factory to convert both the protein and carbohydrate fractions of DGS to advanced biofuels. These results should support improvement of the techno-economic feasibility and net energy return of the first-generation bioethanol process since up to ~30% more fuel products can be produced from the same amount of corn.

This integrated carbohydrate and protein conversion platform is versatile for the bioconversion of other carbohydrate and protein rich biomass, which was demonstrated using microalgae biomass. The mixed fusel alcohols that were produced contained primarily isobutanol and other higher carbon numbers alcohols, including 2-methyl-1-butanol, 3-methyl-1-butanol and 2-phenylethanol. It was previously shown that mixed alcohol forms (especially C 3-C5) provide increased energy densities and other improved physical properties (e.g. reduced water solubility and corrosivity) than ethanol which can provide increased combustion efficiencies, reduced emission profiles, and improved compatibility with the existing liquid fuels infrastructure (see, e.g., U.S. Pat. No. 7,559,961). Therefore, mixed fusel alcohols have promising potential applications as a fuel blendstock in gasoline, diesel, jet fuel, heating oil, or as a neat fuel of itself.

The microbial co-culture developed here, specifically the carbohydrate conversion strain and the protein conversion strain, allows the microbes to utilize multiple substrates and accomplish complex biosynthesis that is difficult to achieve by a single cell. Also it allows division of labor and reduction of the metabolic burden on each cell type. The isobutanol produced from glucose by the carbohydrate conversion strain E. coli BLF2 is higher than that which has been reported from a previous other study where the E. coli production strain included deletion of six genes involved in byproducts formation (see, e.g., Atsumi S et al., Appl. Microbiol. Biotechnol. 2010; 85:651-7), suggesting superior capacity of E. coli strain B as a host for isobutanol production. We envision that the isobutanol yield from E. coli BLF2 strain can be further increased by optimizing the process conditions and strain engineering, e.g., deleting the competing pathways for the byproducts and removing any bottlenecks from the pathway.

In terms of protein conversion, up to 30% of proteins from both the DGS and algae hydrolysates were converted by the co-culture. Without wishing to be limited by mechanism, the incomplete protein conversion in both hydrolysates could be due to several facts. Firstly, the pretreated hydrolysates were directly used as the fermentation broth which may lack of some of the trace nutrients as in synthetic medium such as LB broth. Additionally, potential fermentation inhibitors such as weak acids and furan derivatives (see, e.g., Palmqvist E et al., "Fermentation of lignocellulosic hydrolysates. II: inhibitors and mechanisms of inhibition," *Bioresour. Technol.* 2000; 74:25-33) present in the hydrolysates may have inhibitory effect on the *E. coli* strain. Secondly, the protein conversion strain AY3 can only utilize 13 individual amino acids as the sole carbon source (see, e.g., Huo Y X et al., *Nat. Biotechnol.* 2011; 29:346-51), which leads to the incomplete consumption of the proteins in the hydrolysates. Moreover, the carbohydrates present in the hydrolysates were also utilized as the carbon source for growth by AY3, which may reduce the consumption rate of proteins in the hydrolysates by the protein conversion strain AY3 compared with when only protein was available as the sole carbon source. This could be improved by using different inoculation strategies, i.e., inoculating AY3 following BLF2 in the co-culture when sugars in the hydrolysates are mostly consumed by the carbohydrate conversion strain BLF2 during fermentation.

Figure 4C:
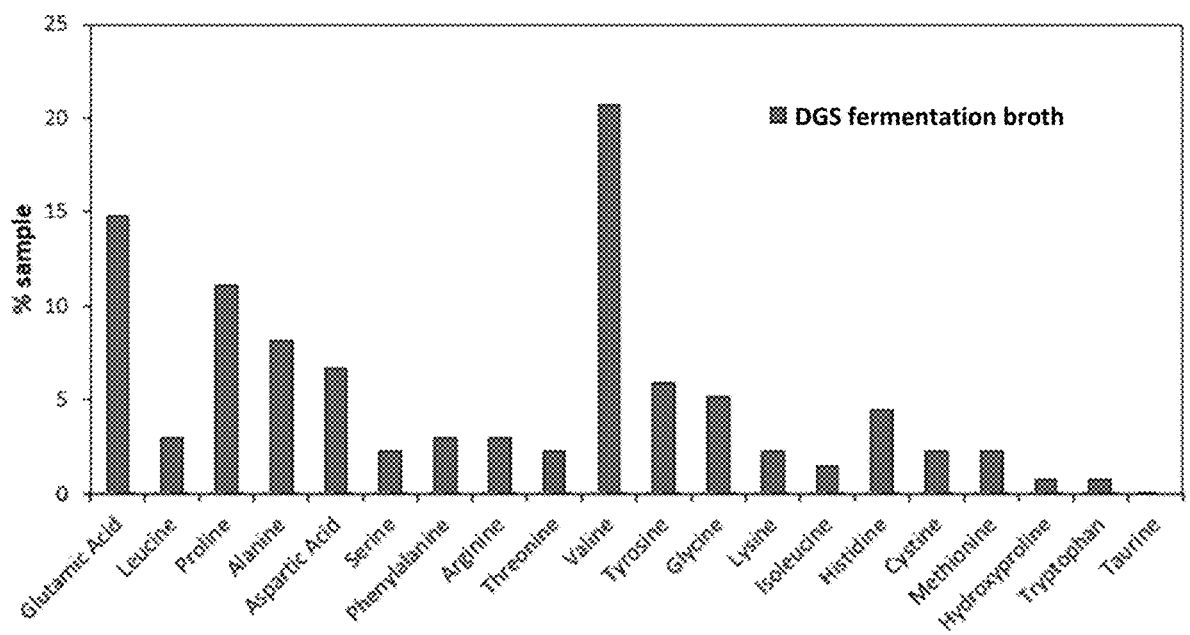

However, the fusel alcohol amino acid preference favors high abundance amino acids such as glutamate and alanine (see, e.g., *Nat. Biotechnol.* 2009; 27:753-9); therefore, isolation of the unutilized high value amino acids such as lysine, methionine, phenylalanine, valine, and/or proline may provide a path toward a secondary high value co-product stream to further facilitate the process economics. For example, as seen in FIG. 4C, amino acid analysis of the DGS fermentation broth provided various high value amino acids, such as valine and proline.

The q-PCR based cell quantification method developed here is a versatile tool for rapidly tracking the individual population in the mixed culture during fermentation. The protein conversion strain AY3 has much lower growth rate than the carbohydrate conversion strain BLF2, which is probably due to the fact that AY3 has more genetic modifications than BLF2, including deletion of several genomic genes. Previous studies have showed that multiple genomic deletions could cause decreases in the cell growth rate of *E. coli* (see, e.g., Kurokawa M et al., "Correlation between genome reduction and bacterial growth," DNA Res. 2016; 23:517-25). When co-culturing two strains whose growth rates differ substantially, it's likely that one species become the dominant population and therefore the population ratios often have to be optimized to obtain a stable culture so that one cell type does not eliminate the other (see, e.g., Goers L et al., "Co-culture systems and technologies: taking synthetic biology to the next level," *J. R. Soc. Interface* 2014; 11:20140065 (13 pp.)).

In the case of our co-culture, although BLF2 cells did grow faster than AY3, the co-culturing of the two species didn't eliminate the growth of AY3 (FIG. 23A-23B). This is probably due to the fact that BLF2 and AY3 don't compete for pentose sugar and proteins as carbon source for growth, although they can both utilize glucose. Therefore, their substrate specificity allows the two strains to establish a stable co-culture system.

Further-more, the co-cultures at certain initial BLF2/AY3 inoculation ratios produced higher amount of fusel alcohols from the hydrolysates than others (FIGS. 19A-19B and FIGS. 20A-20B); q-PCR analysis clearly indicated that the difference between the cell numbers of BLF2 and AY3 in these co-cultures was minimized. The population dynamics analysis of the co-culture in this study demonstrated that changing the initial inoculation ratio is a simple and effective way to tune the co-culture population and that an optimized co-culture population is vital to achieve higher production yield by the engineered *E. coli* consortium.

Overall, we demonstrated 'one-pot' bioconversion of the DGS hydrolysate into fusel alcohols using a microbial co-culture strategy incorporating two engineered *E. coli* strains. The carbohydrate conversion strain *E. coli* BLF2 was constructed from the wild type strain B and showed improved capability to produce fusel alcohols from hexose and pentose sugars compared to previous efforts. The co-culture with an inoculation ratio of 1:1.5 of *E. coli* BLF2 and AY3 achieved the highest total fuel titer of up to 10.3 g/L from DGS hydrolysates. Moreover, the integrated carbohydrate and protein conversion plat-form is also applicable for the bioconversion of other multi-substrate biomass such as algae hydrolysates. The detailed population dynamics study suggested that an optimized co-culture population ratio lead to more efficient 'one-pot' bioconversion of multiple substrates in the hydrolysates.

Example 13: Characterization of Biomass Residuum

Described herein are processes based on dilute acid hydrolysis and consortium bioconversion of high protein biomass for increasing the total fuel yield and co-generation of a concentrated high value amino acid coproduct. This technology provided the means to produce ~10 tons of fusel alcohols in addition to the ~30 tons of ethanol per 100 tons of corn, while simultaneously remineralizing the major N/P nutrients as struvite, and generation of a co-product enriched in high value amino acids. We have demonstrated the flexibility of the technology for other biomass sources and organic waste streams, including algae from wastewater treatment and mixed food waste.

The technology hinges on development of an engineered bio-orthogonal *E. coli* consortium biocatalyst for utilization of the lignocellulosic sugars and low value amino acids, and results in precipitation of the major N/P nutrients as struvite, and a residuum enriched in high value amino acids. In addition to increasing the fuel yield from the starch ethanol process, this process provides major nutrient recycling and provides a high amino acid content residuum that has promising applications beyond ruminate feed, including mariculture, non-ruminate feed, and human nutrition. In particular, following extraction of the fusel alcohol and lipids products from the treated biomass, the residuum was found to be ~65% amino acids on the dry weight basis, with significant enrichment in the following high value amino acids: valine, alanine, proline, glycine, methionine, cysteine, and histidine (FIG. 4C).

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:
1. A method of providing a biomass residuum, the method comprising:
pre-treating a biomass with one or more acids and/or enzymes, thereby providing one or more biocomponents comprising one or more carbohydrates, amino acids, proteins, and peptides;
fermenting the biocomponents with a first genetically engineered organism and a second genetically engineered organism, thereby providing a first fermentation product, wherein the first genetically engineered organism degrades the one or more carbohydrates and the second genetically engineered organism degrades the one or more amino acids, proteins, and peptides; and
separating the first fermentation product, thereby providing a mixed alcohol portion and the biomass residuum comprising of from about 50% total to about 85% total of amino acids on a dry weight basis;
wherein the first genetically engineered organisms comprises:
an exogenous acetolactate synthase or a nucleic acid encoding the exogenous acetolactate synthase, wherein the exogenous acetolactate synthase comprises a polypeptide sequence having at least 99% sequence identity to the amino acid sequence of any one of SEQ ID NOs: 50-53; and
an exogenous 2-ketoacid decarboxylase or a nucleic acid encoding the exogenous 2-ketoacid decarboxylase, wherein the exogenous 2-ketoacid decarboxylase comprises a polypeptide sequence having at least 99% sequence identity to the amino acid sequence of any one of SEQ ID NOs: 55-58; and
wherein the second genetically engineered organism comprises:
a modified alcohol dehydrogenase having increased reactivity with nicotinamide adenine dinucleotide (NADH), as compared to a wild-type alcohol dehydrogenase, or a nucleic acid encoding the modified alcohol dehydrogenase, wherein the modified alcohol dehydrogenase comprises a polypeptide sequence having at least 99% sequence identity to the amino acid sequence of any one of SEQ ID NOs: 1-5; and
a modified ketol-acid reductoisomerase having increased reactivity with NADH, as compared to a wild-type ketol-acid reductoisomerase, or a nucleic acid encoding the modified ketol-acid reductoisomerase, wherein the modified ketol-acid reductoisomerase comprises a polypeptide sequence having at least 99% sequence identity to the amino acid sequence of any one of SEQ ID NOs: 6-7.

2. The method of claim 1, wherein the biomass comprises a distillers' grain.

3. The method of claim 1, wherein the pre-treating step comprises pre-treating the biomass with an acid and with an enzyme.

4. The method of claim 1, wherein the biomass residuum comprises of from about 10% total to about 25% total of valine, about 10% total to about 20% total of glutamic acid, about 5% total to about 15% total of proline, about 5% total to about 15% total of alanine, about 5% total to about 15% total of aspartic acid, about 3% total to about 10% total of tyrosine, about 3% total to about 10% total of glycine, and about 3% total to about 10% total of histidine, or a salt thereof.

5. The method of claim 1, wherein the biomass residuum comprises about 20% total of valine, about 15% total of glutamic acid, about 10% total of proline, about 10% total of alanine, about 10% total of aspartic acid, about 35% total of tyrosine, about 5% total of glycine, and about 5% total of histidine, or a salt thereof.

6. The method of claim 1, wherein the separating step further comprises separating one or more lipids from the first fermentation product, thereby extracting the one or more lipids from the biomass residuum.

7. A method of providing a biomass residuum, the method comprising:
pre-treating a biomass with one or more acids and/or enzymes, thereby providing one or more biocomponents comprising one or more carbohydrates, amino acids, proteins, and peptides;
fermenting the one or more biocomponents with a first genetically engineered organism and a second genetically engineered organism, thereby providing a first fermentation product, wherein the first genetically engineered organism degrades the one or more carbohydrates and the second genetically engineered organism degrades the one or more amino acids, proteins, and peptides; and
separating one or more alcohols from the first fermentation product, thereby resulting in a separated fermentation portion; and
lyophilizing the separated fermentation portion, thereby providing the biomass residuum comprising from about 50% total to about 85% total of amino acids on a dry weight basis;
wherein the first genetically engineered organisms comprises:
an exogenous acetolactate synthase or a nucleic acid encoding the exogenous acetolactate synthase, wherein the exogenous acetolactate synthase comprises a polypeptide sequence having at least 99% sequence identity to the amino acid sequence of any one of SEQ ID NOs: 50-53; and
an exogenous 2-ketoacid decarboxylase or a nucleic acid encoding the exogenous 2-ketoacid decarboxylase, wherein the exogenous 2-ketoacid decarboxylase comprises a polypeptide sequence having at least 99% sequence identity to the amino acid sequence of any one of SEQ ID NOs: 55-58; and
wherein the second genetically engineered organism comprises:
a modified alcohol dehydrogenase having increased reactivity with nicotinamide adenine dinucleotide (NADH), as compared to a wild-type alcohol dehydrogenase, or a nucleic acid encoding the modified alcohol dehydrogenase, wherein the modified alcohol dehydrogenase comprises a polypeptide sequence having at least 99% sequence identity to the amino acid sequence of any one of SEQ ID NOs: 1-5; and
a modified ketol-acid reductoisomerase having increased reactivity with NADH, as compared to a wild-type ketol-acid reductoisomerase, or a nucleic acid encoding the modified ketol-acid reductoisomerase, wherein the modified ketol-acid reductoisomerase comprises a polypeptide sequence having at least 99% sequence identity to the amino acid sequence of any one of SEQ ID NOs: 6-7.

8. The method of claim 7, wherein the biomass comprises a distillers' grain.

9. The method of claim 7, wherein the pre-treating step comprises pre-treating the biomass with an acid and with an enzyme.

10. The method of claim 7, wherein the biomass residuum comprises from about 10% total to about 25% total of valine, about 10% total to about 20% total of glutamic acid, about 5% total to about 15% total of proline, about 5% total to about 15% total of alanine, about 5% total to about 15% total of aspartic acid, about 3% total to about 10% total of tyrosine, about 3% total to about 10% total of glycine, and about 3% total to about 10% total of histidine, or a salt thereof.

11. The method of claim 7, wherein the alcohol is selected from the group consisting of ethanol, propanol, butanol, and alkylated formed thereof.

12. The method of claim 7, wherein the one or more acids comprises hydrochloric acid or sulfuric acid.

13. The method of claim 7, wherein the one or more enzymes comprises one or more proteases.

14. The method of claim 1, wherein the exogenous acetolactate synthase comprises the amino acid sequence of any one of SEQ ID NOs: 50-53;
   wherein the exogenous 2-ketoacid decarboxylase comprises the amino acid sequence of any one of SEQ ID NOs: 55-58;
   wherein the modified alcohol dehydrogenase comprises the amino acid sequence of any one of SEQ ID NOs: 1-5;
   wherein the modified ketol-acid reductoisomerase comprises the amino acid sequence of any one of SEQ ID NOs: 6 or 7.

15. The method of claim 7, wherein the exogenous acetolactate synthase comprises the amino acid sequence of any one of SEQ ID NOs: 50-53;
   wherein the exogenous 2-ketoacid decarboxylase comprises the amino acid sequence of any one of SEQ ID NOs: 55-58;
   wherein the modified alcohol dehydrogenase comprises the amino acid sequence of any one of SEQ ID NOs: 1-5;
   wherein the modified ketol-acid reductoisomerase comprises the amino acid sequence of any one of SEQ ID NOs: 6 or 7.

16. The method of claim 1, wherein the fermenting the biocomponents is performed in *Escherichia*.

17. The method of claim 7, wherein the fermenting the biocomponents is performed in *Escherichia*.

18. The method of claim 1, wherein the fermenting the biocomponents is performed in *E. coli*.

19. The method of claim 7, wherein the fermenting the biocomponents is performed in *E. coli*.

20. The method of claim 6, wherein the biomass residuum comprises from about 50% total to about 85% total of amino acids on a dry weight basis following extraction of lipids and fusel alcohol.

* * * * *

SEQUENCE LISTING

<160> NUMBER OF SEQ ID NOS: 71

<210> SEQ ID NO 1
<211> LENGTH: 387
<212> TYPE: PRT
<213> ORGANISM: Escherichia coli

<400> SEQUENCE: 1

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

```
Gly Glu Asn His Asp Ile Thr Leu Asp Val Ser Arg Arg Ile Tyr Glu
        370                 375                 380

Ala Ala Arg
385

<210> SEQ ID NO 2
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(39)
<223> OTHER INFORMATION: Xaa at position 39 can be any useful amino acid
      substitution (e.g., Ile, Tyr, Val, Leu, Phe, or any other
      conservative amino acid substitution described in the
      specification)

<400> SEQUENCE: 2

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Xaa Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300
```

```
Leu Gln Tyr Ala Glu Arg Val Trp Asn Ile Thr Gly Ser Asp Asp
305                 310                 315                 320

Glu Arg Ile Asp Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
                340                 345                 350

Ile Pro Ala Leu Leu Lys Lys Leu Glu Glu His Gly Met Thr Gln Leu
                355                 360                 365

Gly Glu Asn His Asp Ile Thr Leu Asp Val Ser Arg Arg Ile Tyr Glu
370                 375                 380

Ala Ala Arg
385

<210> SEQ ID NO 3
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (40)..(40)
<223> OTHER INFORMATION: Xaa at position 40 can be any useful amino acid
      substitution (e.g., Pro, Arg, His, Lys, Trp, or any other
      conservative amino acid substitution described in the
      specification)

<400> SEQUENCE: 3

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
                20                  25                  30

Leu Ile Thr Tyr Gly Gly Gly Xaa Val Lys Lys Thr Gly Val Leu Asp
                35                  40                  45

Gln Val Leu Asp Ala Leu Lys Gly Met Asp Val Leu Glu Phe Gly Gly
                50                  55                  60

Ile Glu Pro Asn Pro Ala Tyr Glu Thr Leu Met Asn Ala Val Lys Leu
65              70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Asn Tyr Pro Glu
                100                 105                 110

Asn Ile Asp Pro Trp His Ile Leu Gln Thr Gly Gly Lys Glu Ile Lys
                115                 120                 125

Ser Ala Ile Pro Met Gly Cys Val Leu Thr Leu Pro Ala Thr Gly Ser
                130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
                180                 185                 190

Val Asp Ala Phe Val His Thr Val Glu Gln Tyr Val Thr Lys Pro Val
                195                 200                 205

Asp Ala Lys Ile Gln Asp Arg Phe Ala Glu Gly Ile Leu Leu Thr Leu
                210                 215                 220

Ile Glu Asp Gly Pro Lys Ala Leu Lys Glu Pro Glu Asn Tyr Asp Val
```

```
                       225                 230                 235                 240
        Arg Ala Asn Val Met Trp Ala Ala Thr Gln Ala Leu Asn Gly Leu Ile
                           245                 250                 255

Gly Ala Gly Val Pro Gln Asp Trp Ala Thr His Met Leu Gly His Glu
                           260                 265                 270

Leu Thr Ala Met His Gly Leu Asp His Ala Gln Thr Leu Ala Ile Val
                           275                 280                 285

Leu Pro Ala Leu Trp Asn Glu Lys Arg Asp Thr Lys Arg Ala Lys Leu
                           290                 295                 300

Leu Gln Tyr Ala Glu Arg Val Trp Asn Ile Thr Glu Gly Ser Asp Asp
        305                 310                 315                 320

Glu Arg Ile Asp Ala Ala Ile Ala Ala Thr Arg Asn Phe Phe Glu Gln
                           325                 330                 335

Leu Gly Val Pro Thr His Leu Ser Asp Tyr Gly Leu Asp Gly Ser Ser
                           340                 345                 350

Ile Pro Ala Leu Leu Lys Lys Leu Glu Glu His Gly Met Thr Gln Leu
                           355                 360                 365

Gly Glu Asn His Asp Ile Thr Leu Asp Val Ser Arg Arg Ile Tyr Glu
                           370                 375                 380

Ala Ala Arg
        385

<210> SEQ ID NO 4
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (39)..(40)
<223> OTHER INFORMATION: Xaa at position 39 and 40 can be any useful
      amino acid substitution (e.g., Ile at position 39 and Arg at
      position 40; Tyr at position 39 and His at position 40; as well as
      any other conservative amino acid substitution described in the

<400> SEQUENCE: 4

Met Asn Asn Phe Asn Leu His Thr Pro Thr Arg Ile Leu Phe Gly Lys
        1               5                   10                  15

Gly Ala Ile Ala Gly Leu Arg Glu Gln Ile Pro His Asp Ala Arg Val
                           20                  25                  30

Leu Ile Thr Tyr Gly Gly Xaa Xaa Val Lys Lys Thr Gly Val Leu Asp
                           35                  40                  45

Gln Val Leu Asp Ala Leu Lys Gly Met Asp Val Leu Glu Phe Gly Gly
                           50                  55                  60

Ile Glu Pro Asn Pro Ala Tyr Glu Thr Leu Met Asn Ala Val Lys Leu
        65                  70                  75                  80

Val Arg Glu Gln Lys Val Thr Phe Leu Leu Ala Val Gly Gly Gly Ser
                           85                  90                  95

Val Leu Asp Gly Thr Lys Phe Ile Ala Ala Ala Asn Tyr Pro Glu
                           100                 105                 110

Asn Ile Asp Pro Trp His Ile Leu Gln Thr Gly Gly Lys Glu Ile Lys
                           115                 120                 125

Ser Ala Ile Pro Met Gly Cys Val Leu Thr Leu Pro Ala Thr Gly Ser
                           130                 135                 140

Glu Ser Asn Ala Gly Ala Val Ile Ser Arg Lys Thr Thr Gly Asp Lys
        145                 150                 155                 160
```

-continued

```
Gln Ala Phe His Ser Ala His Val Gln Pro Val Phe Ala Val Leu Asp
            165                 170                 175

Pro Val Tyr Thr Tyr Thr Leu Pro Pro Arg Gln Val Ala Asn Gly Val
        180                 185                 190

Val Asp Ala Phe Val His Thr Val Glu Gln Tyr Val Thr Lys Pro Val
    195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 5
<211> LENGTH: 387
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (37)..(38)
<223> OTHER INFORMATION: Gly, Ile, Tyr, Val, Leu, Phe, or any other
      conservative amino acid substitution described in the
      specification
<220> FEATURE:
<221> NAME/KEY: MOD_RES
<222> LOCATION: (39)..(40)
<223> OTHER INFORMATION: Xaa at position 39 and 40 can be any useful
      amino acid substitution (e.g., Ile at position 39 and Arg at
      position 40; Tyr at position 39 and His at position 40; as well as
      any other conservative amino acid substitution described in the

<400> SEQUENCE: 5

Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Xaa Xaa Xaa Xaa Val Lys Lys Thr Gly Val Leu Asp
        35                  40                  45

Gln Val Leu Asp Ala Leu Lys Gly Met Asp Val Leu Glu Phe Gly Gly
    50                  55                  60
```

Ile Glu Pro Asn Pro Ala Tyr Glu Thr Leu Met Asn Ala Val Lys Leu
 65                  70                  75                  80

Val Arg Glu Gln Lys Val Thr Phe Leu Leu Ala Val Gly Gly Gly Ser
                 85                  90                  95

Val Leu Asp Gly Thr Lys Phe Ile Ala Ala Ala Asn Tyr Pro Glu
            100                 105                 110

Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
            130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
            195                 200                 205

Asp Ala Lys Ile Gln Asp Arg Phe Ala Glu Gly Ile Leu Leu Thr Leu
210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
            275                 280                 285

Leu Pro Ala Leu Trp Asn Glu Lys Arg Asp Thr Lys Arg Ala Lys Leu
            290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
            355                 360                 365

Gly Glu Asn His Asp Ile Thr Leu Asp Val Ser Arg Arg Ile Tyr Glu
370                 375                 380

Ala Ala Arg
385

<210> SEQ ID NO 6
<211> LENGTH: 491
<212> TYPE: PRT
<213> ORGANISM: Escherichia coli

<400> SEQUENCE: 6

Met Ala Asn Tyr Phe Asn Thr Leu Asn Leu Arg Gln Gln Leu Ala Gln
 1               5                  10                  15

Leu Gly Lys Cys Arg Phe Met Gly Arg Asp Glu Phe Ala Asp Gly Ala
             20                  25                  30

Ser Tyr Leu Gln Gly Lys Lys Val Val Ile Val Gly Cys Gly Ala Gln

```
            35                  40                  45
Gly Leu Asn Gln Gly Leu Asn Met Arg Asp Ser Gly Leu Asp Ile Ser
 50                  55                  60

Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460
```

-continued

```
Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 7
<211> LENGTH: 491
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (71)..(71)
<223> OTHER INFORMATION: Ser or Thr at position 71
<220> FEATURE:
<221> NAME/KEY: MOD_RES
<222> LOCATION: (76)..(76)
<223> OTHER INFORMATION: Asp or Glu at position 76
<220> FEATURE:
<221> NAME/KEY: MOD_RES
<222> LOCATION: (78)..(78)
<223> OTHER INFORMATION: Asp or Glu at position 78
<220> FEATURE:
<221> NAME/KEY: MOD_RES
<222> LOCATION: (110)..(110)
<223> OTHER INFORMATION: Val or Ala or Leu or Ile at position 110
<220> FEATURE:
<221> NAME/KEY: MOD_RES
<222> LOCATION: (146)..(146)
<223> OTHER INFORMATION: Gly or Ala at position 146
<220> FEATURE:
<221> NAME/KEY: MOD_RES
<222> LOCATION: (185)..(185)
<223> OTHER INFORMATION: Arg or Lys at position 185
<220> FEATURE:
<221> NAME/KEY: MOD_RES
<222> LOCATION: (433)..(433)
<223> OTHER INFORMATION: Glu or Asp at position 433

<400> SEQUENCE: 7

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
                20                  25                  30

Ser Tyr Leu Gln Gly Lys Lys Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Xaa Ile Ala Glu Lys Xaa Ala Xaa Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Xaa His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Xaa Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Xaa Glu Gly Met Ala Ile Ala Lys
```

```
                  180                 185                 190
Ala Trp Ala Ala Ala Thr Gly Gly His Arg Ala Gly Val Leu Glu Ser
            195                 200                 205

Ser Phe Val Ala Glu Val Lys Ser Asp Leu Met Gly Glu Gln Thr Ile
210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
            245                 250                 255

Gly Trp Glu Thr Ile Thr Glu Ala Leu Lys Gln Gly Gly Ile Thr Leu
        260                 265                 270

Met Met Asp Arg Leu Ser Asn Pro Ala Lys Leu Arg Ala Tyr Ala Leu
    275                 280                 285

Ser Glu Gln Leu Lys Glu Ile Met Ala Pro Leu Phe Gln Lys His Met
290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
            325                 330                 335

Thr Ala Phe Glu Thr Ala Pro Gln Tyr Glu Gly Lys Ile Gly Glu Gln
        340                 345                 350

Glu Tyr Phe Asp Lys Gly Val Leu Met Ile Ala Met Val Lys Ala Gly
    355                 360                 365

Val Glu Leu Ala Phe Glu Thr Met Val Asp Ser Gly Ile Ile Glu Glu
370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
            405                 410                 415

Ala Glu Tyr Gly Asn Tyr Leu Phe Ser Tyr Ala Cys Val Pro Leu Leu
        420                 425                 430

Xaa Pro Phe Met Ala Glu Leu Gln Pro Gly Asp Leu Gly Lys Ala Ile
    435                 440                 445

Pro Glu Gly Ala Val Asp Asn Gly Gln Leu Arg Asp Val Asn Glu Ala
450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
            485                 490

<210> SEQ ID NO 8

<400> SEQUENCE: 8

000

<210> SEQ ID NO 9

<400> SEQUENCE: 9

000

<210> SEQ ID NO 10
<211> LENGTH: 41
<212> TYPE: DNA
<213> ORGANISM: Artificial Sequence
<220> FEATURE:
```

<223> OTHER INFORMATION: Synthetic construct

<400> SEQUENCE: 10
ctcagcgaat tcatgaacaa ctttaatctg cacaccccaa c    41

<210> SEQ ID NO 11
<211> LENGTH: 35
<212> TYPE: DNA
<213> ORGANISM: Artificial Sequence
<220> FEATURE:
<223> OTHER INFORMATION: Synthetic construct

<400> SEQUENCE: 11
tgacctggat ccttagcggg cggcttcgta tatac    35

<210> SEQ ID NO 12
<211> LENGTH: 43
<212> TYPE: DNA
<213> ORGANISM: Artificial Sequence
<220> FEATURE:
<223> OTHER INFORMATION: Synthetic construct

<400> SEQUENCE: 12
ctcagcgaat tcatggctaa ctacttcaat acactgaatc tgc    43

<210> SEQ ID NO 13
<211> LENGTH: 37
<212> TYPE: DNA
<213> ORGANISM: Artificial Sequence
<220> FEATURE:
<223> OTHER INFORMATION: Synthetic construct

<400> SEQUENCE: 13
tgacctggat ccttaacccg caacagcaat acgtttc    37

<210> SEQ ID NO 14
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(27)
<223> OTHER INFORMATION: n can be any nucleic acid to create mutant
      library S40

<400> SEQUENCE: 14
gtattgatta cctacggcgg cggcnnngtg aaaaaaaccg gcgttctc    48

<210> SEQ ID NO 15
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(24)
<223> OTHER INFORMATION: n can be any nucleic acid to create mutant
      library S40

<400> SEQUENCE: 15
gagaacgccg gttttttttca cnnngccgcc gccgtaggta atcaatac    48

<210> SEQ ID NO 16
<211> LENGTH: 48

```
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(27)
<223> OTHER INFORMATION: n can be any nucleic acid to create mutant
      library G39S40

<400> SEQUENCE: 16
gtattgatta cctacggcgg cnnnnnngtg aaaaaaaccg gcgttctc                48

<210> SEQ ID NO 17
<211> LENGTH: 48
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (22)..(27)
<223> OTHER INFORMATION: n can be any nucleic acid to create mutant
      library G39S40

<400> SEQUENCE: 17
gagaacgccg gttttttca cnnnnnngcc gccgtaggta atcaatac                 48

<210> SEQ ID NO 18
<211> LENGTH: 45
<212> TYPE: DNA
<213> ORGANISM: Artificial Sequence
<220> FEATURE:
<223> OTHER INFORMATION: Synthetic construct

<400> SEQUENCE: 18
gtattgatta cctacggcgg cccggtgaaa aaaaccggcg ttctc                   45

<210> SEQ ID NO 19
<211> LENGTH: 45
<212> TYPE: DNA
<213> ORGANISM: Artificial Sequence
<220> FEATURE:
<223> OTHER INFORMATION: Synthetic construct

<400> SEQUENCE: 19
gagaacgccg gttttttca ccgggccgcc gtaggtaatc aatac                    45

<210> SEQ ID NO 20
<211> LENGTH: 45
<212> TYPE: DNA
<213> ORGANISM: Artificial Sequence
<220> FEATURE:
<223> OTHER INFORMATION: Synthetic construct

<400> SEQUENCE: 20
gtattgatta cctacggcgg ccgtgtgaaa aaaaccggcg ttctc                   45

<210> SEQ ID NO 21
<211> LENGTH: 45
<212> TYPE: DNA
<213> ORGANISM: Artificial Sequence
<220> FEATURE:
<223> OTHER INFORMATION: Synthetic construct

<400> SEQUENCE: 21
gagaacgccg gttttttca ccgtgccgcc gtaggtaatc aatac                    45
```

<210> SEQ ID NO 22
<211> LENGTH: 48
<212> TYPE: DNA
<213> ORGANISM: Artificial Sequence
<220> FEATURE:
<223> OTHER INFORMATION: Synthetic construct

<400> SEQUENCE: 22
gtattgatta cctacggcgg catccgtgtg aaaaaaaccg gcgttctc                48

<210> SEQ ID NO 23
<211> LENGTH: 48
<212> TYPE: DNA
<213> ORGANISM: Artificial Sequence
<220> FEATURE:
<223> OTHER INFORMATION: Synthetic construct

<400> SEQUENCE: 23
gagaacgccg gtttttttca cacggatgcc gccgtaggta atcaatac                48

<210> SEQ ID NO 24
<211> LENGTH: 48
<212> TYPE: DNA
<213> ORGANISM: Artificial Sequence
<220> FEATURE:
<223> OTHER INFORMATION: Synthetic construct

<400> SEQUENCE: 24
gtattgatta cctacggcgg ctatcatgtg aaaaaaaccg gcgttctc                48

<210> SEQ ID NO 25
<211> LENGTH: 48
<212> TYPE: DNA
<213> ORGANISM: Artificial Sequence
<220> FEATURE:
<223> OTHER INFORMATION: Synthetic construct

<400> SEQUENCE: 25
gagaacgccg gtttttttca catgatagcc gccgtaggta atcaatac                48

<210> SEQ ID NO 26
<211> LENGTH: 36
<212> TYPE: DNA
<213> ORGANISM: Artificial Sequence
<220> FEATURE:
<223> OTHER INFORMATION: Synthetic construct

<400> SEQUENCE: 26
cgtaaagaat cgattgccga gaaggatgcg gattgg                             36

<210> SEQ ID NO 27
<211> LENGTH: 36
<212> TYPE: DNA
<213> ORGANISM: Artificial Sequence
<220> FEATURE:
<223> OTHER INFORMATION: Synthetic construct

<400> SEQUENCE: 27
ccaatccgca tccttctcgg caatcgattc tttacg                             36

<210> SEQ ID NO 28
<211> LENGTH: 24
<212> TYPE: DNA
<213> ORGANISM: Artificial Sequence
<220> FEATURE:
<223> OTHER INFORMATION: Synthetic construct

```
<400> SEQUENCE: 28
cggacaaggc gcactctgat gtag                                              24

<210> SEQ ID NO 29
<211> LENGTH: 24
<212> TYPE: DNA
<213> ORGANISM: Artificial Sequence
<220> FEATURE:
<223> OTHER INFORMATION: Synthetic construct

<400> SEQUENCE: 29
ctacatcaga gtgcgccttg tccg                                              24

<210> SEQ ID NO 30
<211> LENGTH: 24
<212> TYPE: DNA
<213> ORGANISM: Artificial Sequence
<220> FEATURE:
<223> OTHER INFORMATION: Synthetic construct

<400> SEQUENCE: 30
cggacaaggt gcactctgat gtag                                              24

<210> SEQ ID NO 31
<211> LENGTH: 24
<212> TYPE: DNA
<213> ORGANISM: Artificial Sequence
<220> FEATURE:
<223> OTHER INFORMATION: Synthetic construct

<400> SEQUENCE: 31
ctacatcaga gtgcaccttg tccg                                              24

<210> SEQ ID NO 32
<211> LENGTH: 60
<212> TYPE: DNA
<213> ORGANISM: Artificial Sequence
<220> FEATURE:
<223> OTHER INFORMATION: Synthetic construct

<400> SEQUENCE: 32
gaaagctctc taggtcgacg aggaatcacc atggctaact acttcaatac actgaatctg       60

<210> SEQ ID NO 33
<211> LENGTH: 60
<212> TYPE: DNA
<213> ORGANISM: Artificial Sequence
<220> FEATURE:
<223> OTHER INFORMATION: Synthetic construct

<400> SEQUENCE: 33
gtacttaggc atggtatatc tccttccggg ttaacccgca acagcaatac gtttcatatc       60

<210> SEQ ID NO 34
<211> LENGTH: 60
<212> TYPE: DNA
<213> ORGANISM: Artificial Sequence
<220> FEATURE:
<223> OTHER INFORMATION: Synthetic construct

<400> SEQUENCE: 34
gatatgaaac gtattgctgt tgcgggttaa cccggaagga gatataccat gcctaagtac       60

<210> SEQ ID NO 35
```

<211> LENGTH: 60
<212> TYPE: DNA
<213> ORGANISM: Artificial Sequence
<220> FEATURE:
<223> OTHER INFORMATION: Synthetic construct

<400> SEQUENCE: 35
ggatttgtcc tactcaggag agcgttcacc gacaaacaac agataaaacg aaaggcccag    60

<210> SEQ ID NO 36
<211> LENGTH: 60
<212> TYPE: DNA
<213> ORGANISM: Artificial Sequence
<220> FEATURE:
<223> OTHER INFORMATION: Synthetic construct

<400> SEQUENCE: 36
ctgggccttt cgttttatct gttgtttgtc ggtgaacgct ctcctgagta ggacaaatcc    60

<210> SEQ ID NO 37
<211> LENGTH: 60
<212> TYPE: DNA
<213> ORGANISM: Artificial Sequence
<220> FEATURE:
<223> OTHER INFORMATION: Synthetic construct

<400> SEQUENCE: 37
cagattcagt gtattgaagt agttagccat ggtgattcct cgtcgaccta gagagctttc    60

<210> SEQ ID NO 38
<211> LENGTH: 50
<212> TYPE: DNA
<213> ORGANISM: Artificial Sequence
<220> FEATURE:
<223> OTHER INFORMATION: Synthetic construct

<400> SEQUENCE: 38
ggagaaaggt cacatgaaca actttaatct gcacacccca acccgcattc                50

<210> SEQ ID NO 39
<211> LENGTH: 48
<212> TYPE: DNA
<213> ORGANISM: Artificial Sequence
<220> FEATURE:
<223> OTHER INFORMATION: Synthetic construct

<400> SEQUENCE: 39
ctctagcacg cgtaccatgg gatccttagc gggcggcttc gtatatac                  48

<210> SEQ ID NO 40
<211> LENGTH: 48
<212> TYPE: DNA
<213> ORGANISM: Artificial Sequence
<220> FEATURE:
<223> OTHER INFORMATION: Synthetic construct

<400> SEQUENCE: 40
gtatatacga agccgcccgc taaggatccc atggtacgcg tgctagag                  48

<210> SEQ ID NO 41
<211> LENGTH: 60
<212> TYPE: DNA
<213> ORGANISM: Artificial Sequence
<220> FEATURE:
<223> OTHER INFORMATION: Synthetic construct

<400> SEQUENCE: 41

-continued catgataata atggtttctt agacgtcagg tggcactttt cggggaaatg tgcgcggaac    60

<210> SEQ ID NO 42
<211> LENGTH: 60
<212> TYPE: DNA
<213> ORGANISM: Artificial Sequence
<220> FEATURE:
<223> OTHER INFORMATION: Synthetic construct

<400> SEQUENCE: 42
gttccgcgca catttccccg aaaagtgcca cctgacgtct aagaaaccat tattatcatg    60

<210> SEQ ID NO 43
<211> LENGTH: 50
<212> TYPE: DNA
<213> ORGANISM: Artificial Sequence
<220> FEATURE:
<223> OTHER INFORMATION: Synthetic construct

<400> SEQUENCE: 43
gaatgcgggt tggggtgtgc agattaaagt tgttcatgtg acctttctcc    50

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 570
<212> TYPE: PRT
<213> ORGANISM: Bacillus subtilis

<400> SEQUENCE: 50

Met Thr Lys Ala Thr Lys Glu Gln Lys Ser Leu Val Lys Ser Arg Gly
1               5                   10                  15

```
Ala Glu Leu Val Val Asp Cys Leu Val Glu Gln Gly Val Thr His Val
            20                  25                  30

Phe Gly Ile Pro Gly Ala Lys Ile Asp Ala Val Phe Asp Ala Leu Gln
35                  40                  45

Asp Lys Gly Pro Glu Ile Ile Val Ala Arg His Glu Gln Asn Ala Ala
    50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
                100                 105                 110

Ile Arg Ala Asp Arg Leu Lys Arg Thr His Gln Ser Leu Asp Asn Ala
            115                 120                 125

Ala Leu Phe Gln Pro Ile Thr Lys Tyr Ser Val Glu Val Gln Asp Val
            130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Pro Lys Leu
                180                 185                 190

Gly Pro Ala Ala Asp Asp Ala Ile Ser Ala Ala Ile Ala Lys Ile Gln
            195                 200                 205

Thr Ala Lys Leu Pro Val Val Leu Val Gly Met Lys Gly Gly Arg Pro
            210                 215                 220

Glu Ala Ile Lys Ala Val Arg Lys Leu Leu Lys Lys Val Gln Leu Pro
225                 230                 235                 240

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
                260                 265                 270

Leu Leu Leu Glu Gln Ala Asp Val Val Leu Thr Ile Gly Tyr Asp Pro
                275                 280                 285

Ile Glu Tyr Asp Pro Lys Phe Trp Asn Val Asn Gly Asp Arg Thr Ile
290                 295                 300

Ile His Leu Asp Glu Ile Leu Ala Asp Ile Asp His Ala Tyr Gln Pro
305                 310                 315                 320

Glu Leu Glu Leu Ile Gly Asp Ile Pro Ser Thr Ile Asn His Ile Glu
                325                 330                 335

His Asp Ala Val Lys Val Asp Phe Ala Glu Arg Glu Gln Lys Ile Leu
            340                 345                 350

Ser Asp Leu Lys Gln Tyr Met His Glu Gly Glu Gln Val Pro Ala Asp
            355                 360                 365

Trp Lys Ser Asp Arg Val His Pro Leu Glu Ile Val Lys Glu Leu Arg
            370                 375                 380

Asn Ala Val Asp Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                405                 410                 415

Met Ile Ser Asn Gly Met Gln Thr Leu Gly Val Ala Leu Pro Trp Ala
                420                 425                 430
```

-continued

```
Ile Gly Ala Ser Leu Val Lys Pro Gly Glu Lys Val Val Ser Val Ser
            435                 440                 445

Gly Asp Gly Gly Phe Leu Phe Ser Ala Met Glu Leu Glu Thr Ala Val
450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
                500                 505                 510

Ala Thr Gly Leu Arg Val Glu Ser Pro Asp Gln Leu Ala Asp Val Leu
            515                 520                 525

Arg Gln Gly Met Asn Ala Glu Gly Pro Val Ile Ile Asp Val Pro Val
530                 535                 540

Asp Tyr Ser Asp Asn Met Asn Leu Ala Ser Asp Lys Leu Pro Lys Glu
545                 550                 555                 560

Phe Gly Glu Leu Met Lys Thr Lys Ala Leu
                565                 570

<210> SEQ ID NO 51
<211> LENGTH: 570
<212> TYPE: PRT
<213> ORGANISM: Bacillus subtilis

<400> SEQUENCE: 51

Met Thr Lys Ala Thr Lys Glu Gln Lys Ser Leu Val Lys Ser Arg Gly
1               5                   10                  15

Ala Glu Leu Val Val Asp Cys Leu Val Glu Gln Gly Val Thr His Val
                20                  25                  30

Phe Gly Ile Pro Gly Ala Lys Ile Asp Ala Val Phe Asp Ala Leu Gln
            35                  40                  45

Asp Lys Gly Pro Glu Ile Ile Val Ala Arg His Glu Gln Asn Ala Ala
        50                  55                  60

Phe Met Ala Gln Ala Val Gly Arg Leu Thr Gly Lys Pro Gly Val Val
65                  70                  75                  80

Leu Val Thr Ser Gly Pro Gly Ala Ser Asn Leu Ala Thr Gly Leu Leu
                85                  90                  95

Thr Ala Asn Thr Glu Gly Asp Pro Val Val Ala Leu Ala Gly Asn Val
            100                 105                 110

Ile Arg Ala Asp Arg Leu Lys Arg Thr His Gln Ser Leu Asp Asn Ala
        115                 120                 125

Ala Leu Phe Gln Pro Ile Thr Lys Tyr Ser Val Glu Val Gln Asp Val
    130                 135                 140

Lys Asn Ile Pro Glu Ala Val Thr Asn Ala Phe Arg Ile Ala Ser Ala
145                 150                 155                 160

Gly Gln Ala Gly Ala Ala Phe Val Ser Phe Pro Gln Asp Val Val Asn
                165                 170                 175

Glu Val Thr Asn Thr Lys Asn Val Arg Ala Val Ala Ala Pro Lys Leu
            180                 185                 190

Gly Pro Ala Ala Asp Asp Ala Ile Ser Ala Ala Ile Ala Lys Ile Gln
        195                 200                 205

Thr Ala Lys Leu Pro Val Val Leu Val Gly Met Lys Gly Gly Arg Pro
    210                 215                 220

Glu Ala Ile Lys Ala Val Arg Lys Leu Leu Lys Lys Val Gln Leu Pro
225                 230                 235                 240
```

Phe Val Glu Thr Tyr Gln Ala Ala Gly Thr Leu Ser Arg Asp Leu Glu
                245                 250                 255

Asp Gln Tyr Phe Gly Arg Ile Gly Leu Phe Arg Asn Gln Pro Gly Asp
            260                 265                 270

Leu Leu Leu Glu Gln Ala Asp Val Val Leu Thr Ile Gly Tyr Asp Pro
        275                 280                 285

Ile Glu Tyr Asp Pro Lys Phe Trp Asn Val Asn Gly Asp Arg Thr Ile
    290                 295                 300

Ile His Leu Asp Glu Ile Leu Ala Asp Ile Asp His Ala Tyr Gln Pro
305                 310                 315                 320

Glu Leu Glu Leu Ile Gly Asp Ile Pro Ser Thr Ile Asn His Ile Glu
                325                 330                 335

His Asp Ala Val Lys Val Asp Phe Ala Glu Arg Glu Gln Lys Ile Leu
            340                 345                 350

Ser Asp Leu Lys Gln Tyr Met His Glu Gly Glu Gln Val Pro Ala Asp
        355                 360                 365

Trp Lys Ser Asp Arg Val His Pro Leu Glu Ile Val Lys Glu Leu Arg
    370                 375                 380

Asn Ala Val Asp His Val Thr Val Thr Cys Asp Ile Gly Ser His
385                 390                 395                 400

Ala Ile Trp Met Ser Arg Tyr Phe Arg Ser Tyr Glu Pro Leu Thr Leu
                405                 410                 415

Met Ile Ser Asn Gly Met Gln Thr Leu Gly Val Ala Leu Pro Trp Ala
            420                 425                 430

Ile Gly Ala Ser Leu Val Lys Pro Gly Glu Lys Val Val Ser Val Ser
        435                 440                 445

Gly Asp Gly Gly Phe Leu Phe Ser Ala Met Glu Leu Glu Thr Ala Val
    450                 455                 460

Arg Leu Lys Ala Pro Ile Val His Ile Val Trp Asn Asp Ser Thr Tyr
465                 470                 475                 480

Asp Met Val Ala Phe Gln Gln Leu Lys Lys Tyr Asn Arg Thr Ser Ala
                485                 490                 495

Val Asp Phe Gly Asn Ile Asp Ile Val Lys Tyr Ala Glu Ser Phe Gly
            500                 505                 510

Ala Thr Gly Leu Arg Val Glu Ser Pro Asp Gln Leu Ala Asp Val Leu
        515                 520                 525

Arg Gln Gly Met Asn Ala Glu Gly Pro Val Ile Ile Asp Val Pro Val
    530                 535                 540

Asp Tyr Ser Asp Asn Met Asn Leu Ala Ser Asp Lys Leu Pro Lys Glu
545                 550                 555                 560

Phe Gly Glu Leu Met Lys Thr Lys Ala Leu
                565                 570

<210> SEQ ID NO 52
<211> LENGTH: 559
<212> TYPE: PRT
<213> ORGANISM: Klebsiella pneumoniae

<400> SEQUENCE: 52

Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser

```
                35                  40                  45
Ile Arg Ile Ile Pro Val Arg His Glu Ala Asn Ala Ala Phe Met Ala
 50                  55                  60

Ala Ala Val Gly Arg Ile Thr Gly Lys Ala Gly Val Ala Leu Val Thr
 65                  70                  75                  80

Ser Gly Pro Gly Cys Ser Asn Leu Ile Thr Gly Met Ala Thr Ala Asn
                 85                  90                  95

Ser Glu Gly Asp Pro Val Val Ala Leu Gly Gly Ala Val Lys Arg Ala
                100                 105                 110

Asp Lys Ala Lys Gln Val His Gln Ser Met Asp Thr Val Ala Met Phe
                115                 120                 125

Ser Pro Val Thr Lys Tyr Ala Ile Glu Val Thr Ala Pro Asp Ala Leu
                130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
                180                 185                 190

Pro Asp Asp Ala Ile Asp Gln Val Ala Lys Leu Ile Ala Gln Ala Lys
                195                 200                 205

Asn Pro Ile Phe Leu Leu Gly Leu Met Ala Ser Gln Pro Glu Asn Ser
210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
                260                 265                 270

Gln Leu Ala Asp Leu Val Ile Cys Ile Gly Tyr Ser Pro Val Glu Tyr
                275                 280                 285

Glu Pro Ala Met Trp Asn Ser Gly Asn Ala Thr Leu Val His Ile Asp
                290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
                340                 345                 350

Gln His Gln Arg Glu Leu Leu Asp Arg Arg Gly Ala Gln Leu Asn Gln
                355                 360                 365

Phe Ala Leu His Pro Leu Arg Ile Val Arg Ala Met Gln Asp Ile Val
                370                 375                 380

Asn Ser Asp Val Thr Leu Thr Val Asp Met Gly Ser Phe His Ile Trp
385                 390                 395                 400

Ile Ala Arg Tyr Leu Tyr Thr Phe Arg Ala Arg Gln Val Met Ile Ser
                405                 410                 415

Asn Gly Gln Gln Thr Met Gly Val Ala Leu Pro Trp Ala Ile Gly Ala
                420                 425                 430

Trp Leu Val Asn Pro Glu Arg Lys Val Val Ser Val Ser Gly Asp Gly
                435                 440                 445

Gly Phe Leu Gln Ser Ser Met Glu Leu Glu Thr Ala Val Arg Leu Lys
                450                 455                 460
```

```
Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu Arg Ala Ala
            515                 520                 525

Met Asp Val Asp Gly Pro Ala Val Ala Ile Pro Val Asp Tyr Arg
530                 535                 540

Asp Asn Pro Leu Leu Met Gly Gln Leu His Leu Ser Gln Ile Leu
545                 550                 555

<210> SEQ ID NO 53
<211> LENGTH: 554
<212> TYPE: PRT
<213> ORGANISM: Lactococcus lactis

<400> SEQUENCE: 53

Met Ser Glu Lys Gln Phe Gly Ala Asn Leu Val Val Asp Ser Leu Ile
1               5                   10                  15

Asn His Lys Val Lys Tyr Val Phe Gly Ile Pro Gly Ala Lys Ile Asp
                20                  25                  30

Arg Val Phe Asp Leu Leu Glu Asn Glu Gly Pro Gln Met Val Val
            35                  40                  45

Thr Arg His Glu Gln Gly Ala Ala Phe Met Ala Gln Ala Val Gly Arg
50                  55                  60

Leu Thr Gly Glu Pro Gly Val Val Val Thr Ser Gly Pro Gly Val
65                  70                  75                  80

Ser Asn Leu Ala Thr Pro Leu Leu Thr Ala Thr Ser Glu Gly Asp Ala
                85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys
        115                 120                 125

Tyr Ser Ala Glu Val Leu Asp Pro Asn Thr Leu Ser Glu Ser Ile Ala
130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
            180                 185                 190

Asn Tyr Leu Ala Gln Ala Ile Lys Asn Ala Val Leu Pro Val Ile Leu
        195                 200                 205

Val Gly Ala Gly Ala Ser Asp Ala Lys Val Ala Ser Ser Leu Arg Asn
210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
                245                 250                 255

Leu Phe Arg Asn Gln Pro Gly Asp Met Leu Leu Lys Arg Ser Asp Leu
            260                 265                 270

Val Ile Ala Val Gly Tyr Asp Pro Ile Glu Tyr Glu Ala Arg Asn Trp
```

Asn Ala Glu Ile Asp Ser Arg Ile Ile Val Ile Asp Asn Ala Ile Ala
      275                 280                 285
290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                    325                 330                 335

Pro Lys Gly Thr Lys Asp Tyr Leu Asp Gly Leu His Glu Val Ala Glu
                340                 345                 350

Gln His Glu Phe Asp Thr Glu Asn Thr Glu Glu Gly Arg Met His Pro
            355                 360                 365

Leu Asp Leu Val Ser Thr Phe Gln Glu Ile Val Lys Asp Asp Glu Thr
        370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                    405                 410                 415

Leu Gly Val Ala Leu Pro Trp Ala Ile Thr Ala Ala Leu Leu Arg Pro
                420                 425                 430

Gly Lys Lys Val Tyr Ser His Ser Gly Asp Gly Phe Leu Phe Thr
            435                 440                 445

Gly Gln Glu Leu Glu Thr Ala Val Arg Leu Asn Leu Pro Ile Val Gln
        450                 455                 460

Ile Ile Trp Asn Asp Gly His Tyr Asp Met Val Lys Phe Gln Glu Glu
465                 470                 475                 480

Met Lys Tyr Gly Arg Ser Ala Ala Val Asp Phe Gly Tyr Val Asp Tyr
                    485                 490                 495

Val Lys Tyr Ala Glu Ala Met Arg Ala Lys Gly Tyr Arg Ala His Ser
                500                 505                 510

Lys Glu Glu Leu Ala Glu Ile Leu Lys Ser Ile Pro Asp Thr Thr Gly
            515                 520                 525

Pro Val Val Ile Asp Val Pro Leu Asp Tyr Ser Asp Asn Ile Lys Leu
        530                 535                 540

Ala Glu Lys Leu Leu Pro Glu Glu Phe Tyr
545                 550

<210> SEQ ID NO 54
<211> LENGTH: 616
<212> TYPE: PRT
<213> ORGANISM: Escherichia coli

<400> SEQUENCE: 54

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

```
Arg Glu Leu Ile Ala Asp Ser Val Glu Tyr Met Val Asn Ala His Cys
                100                 105                 110

Ala Asp Ala Met Val Cys Ile Ser Asn Cys Asp Lys Ile Thr Pro Gly
            115                 120                 125

Met Leu Met Ala Ser Leu Arg Leu Asn Ile Pro Val Ile Phe Val Ser
        130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Ala Val Glu Ala
    450                 455                 460

Ile Leu Gly Gly Lys Val Val Ala Gly Asp Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
```

```
            515                 520                 525
Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
                580                 585                 590

Leu Arg Ala Tyr Ala Ser Leu Ala Thr Ser Ala Asp Lys Gly Ala Val
                595                 600                 605

Arg Asp Lys Ser Lys Leu Gly Gly
                610                 615

<210> SEQ ID NO 55
<211> LENGTH: 548
<212> TYPE: PRT
<213> ORGANISM: Lactococcus lactis

<400> SEQUENCE: 55

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
                20                  25                  30

Asp Gln Ile Ile Ser His Lys Asp Met Lys Trp Val Gly Asn Ala Asn
            35                  40                  45

Glu Leu Asn Ala Ser Tyr Met Ala Asp Gly Tyr Ala Arg Thr Lys Lys
        50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
                100                 105                 110

His Thr Leu Ala Asp Gly Asp Phe Lys His Phe Met Lys Met His Glu
            115                 120                 125

Pro Val Thr Ala Ala Arg Thr Leu Leu Thr Ala Glu Asn Ala Thr Val
        130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
                180                 185                 190

Glu Ile Leu Asn Lys Ile Gln Glu Ser Leu Lys Asn Ala Lys Lys Pro
            195                 200                 205

Ile Val Ile Thr Gly His Glu Ile Ile Ser Phe Gly Leu Glu Lys Thr
        210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
                260                 265                 270
```

Ala Asp Phe Ile Leu Met Leu Gly Val Lys Leu Thr Asp Ser Ser Thr
275                 280                 285

Gly Ala Phe Thr His His Leu Asn Glu Asn Lys Met Ile Ser Leu Asn
290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
                340                 345                 350

Leu Leu Ser Gln Asp Arg Leu Trp Gln Ala Val Glu Asn Leu Thr Gln
                355                 360                 365

Ser Asn Glu Thr Ile Val Ala Glu Gln Gly Thr Ser Phe Phe Gly Ala
370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ala Ile Arg Glu Lys Ile Asn
                435                 440                 445

Pro Ile Cys Phe Ile Ile Asn Asn Asp Gly Tyr Thr Val Glu Arg Glu
                450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Pro Asn Arg Met Tyr Trp Ile Glu Leu Ile Leu Ala Lys
                515                 520                 525

Glu Gly Ala Pro Lys Val Leu Lys Lys Met Gly Lys Leu Phe Ala Glu
530                 535                 540

Gln Asn Lys Ser
545

<210> SEQ ID NO 56
<211> LENGTH: 547
<212> TYPE: PRT
<213> ORGANISM: Lactococcus lactis

<400> SEQUENCE: 56

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
                20                  25                  30

Asp Gln Ile Ile Ser Arg Glu Asp Met Lys Trp Ile Gly Asn Ala Asn
                35                  40                  45

Glu Leu Asn Ala Ser Tyr Met Ala Asp Gly Tyr Ala Arg Thr Lys Lys
            50                  55                  60

Ala Ala Ala Phe Leu Thr Thr Phe Gly Val Gly Glu Leu Ser Ala Ile
65              70                  75                  80

Asn Gly Leu Ala Gly Ser Tyr Ala Glu Asn Leu Pro Val Val Glu Ile
                85                  90                  95

-continued

```
Val Gly Ser Pro Thr Ser Lys Val Gln Asn Asp Gly Lys Phe Val His
            100                 105                 110
His Thr Leu Ala Asp Gly Asp Phe Lys His Phe Met Lys Met His Glu
            115                 120                 125
Pro Val Thr Ala Ala Arg Thr Leu Leu Thr Ala Glu Asn Ala Thr Tyr
            130                 135                 140
Glu Ile Asp Arg Val Leu Ser Gln Leu Leu Lys Glu Arg Lys Pro Val
145                 150                 155                 160
Tyr Ile Asn Leu Pro Val Asp Val Ala Ala Ala Lys Ala Glu Lys Pro
                165                 170                 175
Ala Leu Ser Leu Glu Lys Glu Ser Ser Thr Thr Asn Thr Thr Glu Gln
            180                 185                 190
Val Ile Leu Ser Lys Ile Glu Glu Ser Leu Lys Asn Ala Gln Lys Pro
            195                 200                 205
Val Val Ile Ala Gly His Glu Val Ile Ser Phe Gly Leu Glu Lys Thr
            210                 215                 220
Val Thr Gln Phe Val Ser Glu Thr Lys Leu Pro Ile Thr Thr Leu Asn
225                 230                 235                 240
Phe Gly Lys Ser Ala Val Asp Glu Ser Leu Pro Ser Phe Leu Gly Ile
                245                 250                 255
Tyr Asn Gly Lys Leu Ser Glu Ile Ser Leu Lys Asn Phe Val Glu Ser
            260                 265                 270
Ala Asp Phe Ile Leu Met Leu Gly Val Lys Leu Thr Asp Ser Ser Thr
            275                 280                 285
Gly Ala Phe Thr His His Leu Asp Glu Asn Lys Met Ile Ser Leu Asn
            290                 295                 300
Ile Asp Glu Gly Ile Ile Phe Asn Lys Val Val Glu Asp Phe Asp Phe
305                 310                 315                 320
Arg Ala Val Val Ser Ser Leu Ser Glu Leu Lys Gly Ile Glu Tyr Glu
                325                 330                 335
Gly Gln Tyr Ile Asp Lys Gln Tyr Glu Glu Phe Ile Pro Ser Ser Ala
            340                 345                 350
Pro Leu Ser Gln Asp Arg Leu Trp Gln Ala Val Glu Ser Leu Thr Gln
            355                 360                 365
Ser Asn Glu Thr Ile Val Ala Glu Gln Gly Thr Ser Phe Phe Gly Ala
            370                 375                 380
Ser Thr Ile Phe Leu Lys Ser Asn Ser Arg Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ser Ile Arg Glu Lys Leu Asn
            435                 440                 445
Pro Ile Cys Phe Ile Ile Asn Asn Asp Gly Tyr Thr Val Glu Arg Glu
            450                 455                 460
Ile His Gly Pro Thr Gln Ser Tyr Asn Asp Ile Pro Met Trp Asn Tyr
465                 470                 475                 480
Ser Lys Leu Pro Glu Thr Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
```

```
Gln Ala Asp Val Asn Arg Met Tyr Trp Ile Glu Leu Val Leu Glu Lys
            515                 520                 525

Glu Asp Ala Pro Lys Leu Leu Lys Lys Met Gly Lys Leu Phe Ala Glu
530                 535                 540

Gln Asn Lys
545

<210> SEQ ID NO 57
<211> LENGTH: 550
<212> TYPE: PRT
<213> ORGANISM: Salmonella typhimurium

<400> SEQUENCE: 57

Met Gln Asn Pro Tyr Thr Val Ala Asp Tyr Leu Leu Asp Arg Leu Ala
1               5                   10                  15

Gly Cys Gly Ile Gly His Leu Phe Gly Val Pro Gly Asp Tyr Asn Leu
            20                  25                  30

Gln Phe Leu Asp His Val Ile Asp His Pro Thr Leu Arg Trp Val Gly
        35                  40                  45

Cys Ala Asn Glu Leu Asn Ala Ala Tyr Ala Ala Asp Gly Tyr Ala Arg
    50                  55                  60

Met Ser Gly Ala Gly Ala Leu Leu Thr Thr Phe Gly Val Gly Glu Leu
65                  70                  75                  80

Ser Ala Ile Asn Gly Ile Ala Gly Ser Tyr Ala Glu Tyr Val Pro Val
                85                  90                  95

Leu His Ile Val Gly Ala Pro Cys Ser Ala Ala Gln Gln Arg Gly Glu
            100                 105                 110

Leu Met His His Thr Leu Gly Asp Gly Asp Phe Arg His Phe Tyr Arg
        115                 120                 125

Met Ser Gln Ala Ile Ser Ala Ala Ser Ala Ile Leu Asp Glu Gln Asn
    130                 135                 140

Ala Cys Phe Glu Ile Asp Arg Val Leu Gly Glu Met Leu Ala Ala Arg
145                 150                 155                 160

Arg Pro Gly Tyr Ile Met Leu Pro Ala Asp Val Ala Lys Lys Thr Ala
                165                 170                 175

Ile Pro Pro Thr Gln Ala Leu Ala Leu Pro Val His Glu Ala Gln Ser
            180                 185                 190

Gly Val Glu Thr Ala Phe Arg Tyr His Ala Arg Gln Cys Leu Met Asn
        195                 200                 205

Ser Arg Arg Ile Ala Leu Leu Ala Asp Phe Leu Ala Gly Arg Phe Gly
    210                 215                 220

Leu Arg Pro Leu Leu Gln Arg Trp Met Ala Glu Thr Pro Ile Ala His
225                 230                 235                 240

Ala Thr Leu Leu Met Gly Lys Gly Leu Phe Asp Glu Gln His Pro Asn
                245                 250                 255

Phe Val Gly Thr Tyr Ser Ala Gly Ala Ser Ser Lys Glu Val Arg Gln
            260                 265                 270

Ala Ile Glu Asp Ala Asp Arg Val Ile Cys Val Gly Thr Arg Phe Val
        275                 280                 285

Asp Thr Leu Thr Ala Gly Phe Thr Gln Gln Leu Pro Ala Glu Arg Thr
    290                 295                 300

Leu Glu Ile Gln Pro Tyr Ala Ser Arg Ile Gly Glu Thr Trp Phe Asn
305                 310                 315                 320

Leu Pro Met Ala Gln Ala Val Ser Thr Leu Arg Glu Leu Cys Leu Glu
                325                 330                 335
```

-continued

Cys Ala Phe Ala Pro Pro Thr Arg Ser Ala Gly Gln Pro Val Arg
                340                 345                 350

Ile Asp Lys Gly Glu Leu Thr Gln Glu Ser Phe Trp Gln Thr Leu Gln
                355                 360                 365

Gln Tyr Leu Lys Pro Gly Asp Ile Ile Leu Val Asp Gln Gly Thr Ala
        370                 375                 380

Ala Phe Gly Ala Ala Leu Ser Leu Pro Asp Gly Ala Glu Val Val
385                 390                 395                 400

Leu Gln Pro Leu Trp Gly Ser Ile Gly Tyr Ser Leu Pro Ala Ala Phe
                405                 410                 415

Gly Ala Gln Thr Ala Cys Pro Asp Arg Arg Val Ile Leu Ile Ile Gly
                420                 425                 430

Asp Gly Ala Ala Gln Leu Thr Ile Gln Glu Met Gly Ser Met Leu Arg
                435                 440                 445

Asp Gly Gln Ala Pro Val Ile Leu Leu Leu Asn Asn Asp Gly Tyr Thr
        450                 455                 460

Val Glu Arg Ala Ile His Gly Ala Ala Gln Arg Tyr Asn Asp Ile Ala
465                 470                 475                 480

Ser Trp Asn Trp Thr Gln Ile Pro Pro Ala Leu Asn Ala Ala Gln Gln
                485                 490                 495

Ala Glu Cys Trp Arg Val Thr Gln Ala Ile Gln Leu Ala Glu Val Leu
                500                 505                 510

Glu Arg Leu Ala Arg Pro Gln Arg Leu Ser Phe Ile Glu Val Met Leu
                515                 520                 525

Pro Lys Ala Asp Leu Pro Glu Leu Leu Arg Thr Val Thr Arg Ala Leu
        530                 535                 540

Glu Ala Arg Asn Gly Gly
545                 550

<210> SEQ ID NO 58
<211> LENGTH: 554
<212> TYPE: PRT
<213> ORGANISM: Clostridium acetobutylicum

<400> SEQUENCE: 58

Met Lys Ser Glu Tyr Thr Ile Gly Arg Tyr Leu Leu Asp Arg Leu Ser
1               5                   10                  15

Glu Leu Gly Ile Arg His Ile Phe Gly Val Pro Gly Asp Tyr Asn Leu
                20                  25                  30

Ser Phe Leu Asp Tyr Ile Met Glu Tyr Lys Gly Ile Asp Trp Val Gly
        35                  40                  45

Asn Cys Asn Glu Leu Asn Ala Gly Tyr Ala Ala Asp Gly Tyr Ala Arg
    50                  55                  60

Ile Asn Gly Ile Gly Ala Ile Leu Thr Thr Phe Gly Val Gly Glu Leu
65                  70                  75                  80

Ser Ala Ile Asn Ala Ile Ala Gly Ala Tyr Ala Glu Gln Val Pro Val
                85                  90                  95

Val Lys Ile Thr Gly Ile Pro Thr Ala Lys Val Arg Asp Asn Gly Leu
                100                 105                 110

Tyr Val His His Thr Leu Gly Asp Gly Arg Phe Asp His Phe Glu
            115                 120                 125

Met Phe Arg Glu Val Thr Val Ala Glu Ala Leu Leu Ser Glu Glu Asn
        130                 135                 140

Ala Ala Gln Glu Ile Asp Arg Val Leu Ile Ser Cys Trp Arg Gln Lys

```
            145                 150                 155                 160
Arg Pro Val Leu Ile Asn Leu Pro Ile Asp Val Tyr Asp Lys Pro Ile
                165                 170                 175
Asn Lys Pro Leu Lys Pro Leu Leu Asp Tyr Thr Ile Ser Ser Asn Lys
                180                 185                 190
Glu Ala Ala Cys Glu Phe Val Thr Glu Ile Val Pro Ile Ile Asn Arg
                195                 200                 205
Ala Lys Lys Pro Val Ile Leu Ala Asp Tyr Gly Val Tyr Arg Tyr Gln
    210                 215                 220
Val Gln His Val Leu Lys Asn Leu Ala Glu Lys Thr Gly Phe Pro Val
225                 230                 235                 240
Ala Thr Leu Ser Met Gly Lys Gly Val Phe Asn Glu Ala His Pro Gln
                245                 250                 255
Phe Ile Gly Val Tyr Asn Gly Asp Val Ser Ser Pro Tyr Leu Arg Gln
                260                 265                 270
Arg Val Asp Glu Ala Asp Cys Ile Ile Ser Val Gly Val Lys Leu Thr
            275                 280                 285
Asp Ser Thr Thr Gly Gly Phe Ser His Gly Phe Ser Lys Arg Asn Val
        290                 295                 300
Ile His Ile Asp Pro Phe Ser Ile Lys Ala Lys Gly Lys Lys Tyr Ala
305                 310                 315                 320
Pro Ile Thr Met Lys Asp Ala Leu Thr Glu Leu Thr Ser Lys Ile Glu
                325                 330                 335
His Arg Asn Phe Glu Asp Leu Asp Ile Lys Pro Tyr Lys Ser Asp Asn
                340                 345                 350
Gln Lys Tyr Phe Ala Lys Glu Lys Pro Ile Thr Gln Lys Arg Phe Phe
            355                 360                 365
Glu Arg Ile Ala His Phe Ile Lys Glu Lys Asp Val Leu Leu Ala Glu
        370                 375                 380
Gly Gly Thr Cys Phe Phe Gly Ala Ser Thr Ile Gln Leu Pro Lys Asp
385                 390                 395                 400
Ala Thr Phe Ile Gly Gln Pro Leu Trp Gly Ser Ile Gly Tyr Thr Leu
                405                 410                 415
Pro Ala Leu Leu Gly Ser Gln Leu Ala Asp Gln Lys Arg Arg Asn Ile
                420                 425                 430
Leu Leu Ile Gly Asp Gly Ala Phe Gln Met Thr Ala Gln Glu Ile Ser
            435                 440                 445
Thr Met Leu Arg Leu Gln Ile Lys Pro Ile Ile Phe Leu Ile Asn Asn
450                 455                 460
Asp Gly Tyr Thr Ile Glu Arg Ala Ile His Gly Arg Glu Gln Val Tyr
465                 470                 475                 480
Asn Asn Ile Gln Met Trp Arg Tyr His Asn Val Pro Lys Val Leu Gly
                485                 490                 495
Pro Lys Glu Cys Ser Leu Thr Phe Lys Val Gln Ser Glu Thr Glu Leu
            500                 505                 510
Glu Lys Ala Leu Leu Val Ala Asp Lys Asp Cys Glu His Leu Ile Phe
        515                 520                 525
Ile Glu Val Val Met Asp Arg Tyr Asp Lys Pro Glu Pro Leu Glu Arg
            530                 535                 540
Leu Ser Lys Arg Phe Ala Asn Gln Asn Asn
545                 550

<210> SEQ ID NO 59
```

-continued

<400> SEQUENCE: 59

000

<210> SEQ ID NO 60
<211> LENGTH: 71
<212> TYPE: DNA
<213> ORGANISM: Artificial Sequence
<220> FEATURE:
<223> OTHER INFORMATION: Synthetic construct (primer)

<400> SEQUENCE: 60
ggatggcgat actctgccat ccgtaatttt tactccactt cctgccagtt tgtgtaggct    60
ggagctgctt c                                                         71

<210> SEQ ID NO 61
<211> LENGTH: 74
<212> TYPE: DNA
<213> ORGANISM: Artificial Sequence
<220> FEATURE:
<223> OTHER INFORMATION: Synthetic construct (primer)

<400> SEQUENCE: 61
cgctattcta gtttgtgata tttttcgcc accacaagga gtggaaaatg tgacatggga    60
attagccatg gtcc                                                      74

<210> SEQ ID NO 62
<211> LENGTH: 26
<212> TYPE: DNA
<213> ORGANISM: Artificial Sequence
<220> FEATURE:
<223> OTHER INFORMATION: Synthetic construct (primer)

<400> SEQUENCE: 62
gtaaaaaata tgttccgcgc aggtcc                                         26

<210> SEQ ID NO 63
<211> LENGTH: 47
<212> TYPE: DNA
<213> ORGANISM: Artificial Sequence
<220> FEATURE:
<223> OTHER INFORMATION: Synthetic construct (primer)

<400> SEQUENCE: 63
tttatttgat gcctctagca cgcgtacgcg tttaaccccc cagtttc                  47

<210> SEQ ID NO 64
<211> LENGTH: 27
<212> TYPE: DNA
<213> ORGANISM: Artificial Sequence
<220> FEATURE:
<223> OTHER INFORMATION: Synthetic construct (primer)

<400> SEQUENCE: 64
acgcgtgcta gaggcatcaa ataaaac                                        27

<210> SEQ ID NO 65
<211> LENGTH: 25
<212> TYPE: DNA
<213> ORGANISM: Artificial Sequence
<220> FEATURE:
<223> OTHER INFORMATION: Synthetic construct (primer)

<400> SEQUENCE: 65

```
agtgagcgag gaagcggaat atatc                                         25

<210> SEQ ID NO 66
<211> LENGTH: 24
<212> TYPE: DNA
<213> ORGANISM: Artificial Sequence
<220> FEATURE:
<223> OTHER INFORMATION: Synthetic construct (primer)

<400> SEQUENCE: 66
gcaaaaaagc ggttagctcc ttcg                                          24

<210> SEQ ID NO 67
<211> LENGTH: 59
<212> TYPE: DNA
<213> ORGANISM: Artificial Sequence
<220> FEATURE:
<223> OTHER INFORMATION: Synthetic construct (primer)

<400> SEQUENCE: 67
ctcctactgt atacatggta tatctccttg tcgacaatga attcggtcag tgcgtcctg    59

<210> SEQ ID NO 68
<211> LENGTH: 21
<212> TYPE: DNA
<213> ORGANISM: Artificial Sequence
<220> FEATURE:
<223> OTHER INFORMATION: Synthetic construct (primer)

<400> SEQUENCE: 68
gctttaatga gtggaatcgc c                                             21

<210> SEQ ID NO 69
<211> LENGTH: 21
<212> TYPE: DNA
<213> ORGANISM: Artificial Sequence
<220> FEATURE:
<223> OTHER INFORMATION: Synthetic construct (primer)

<400> SEQUENCE: 69
gatgcaatgt tctggctaac g                                             21

<210> SEQ ID NO 70
<211> LENGTH: 21
<212> TYPE: DNA
<213> ORGANISM: Artificial Sequence
<220> FEATURE:
<223> OTHER INFORMATION: Synthetic construct (primer)

<400> SEQUENCE: 70
gtggaaagag ggcgataaga g                                             21

<210> SEQ ID NO 71
<211> LENGTH: 20
<212> TYPE: DNA
<213> ORGANISM: Artificial Sequence
<220> FEATURE:
<223> OTHER INFORMATION: Synthetic construct (primer)

<400> SEQUENCE: 71
tcatgacgtt ggtagaagcg                                               20
```